United States Patent [19]

Ohno et al.

[11] 4,301,164

[45] Nov. 17, 1981

[54] 5,6,7-TRINOR-4,8-INTER-M-PHENYLENE PGI$_2$ DERIVATIVES

[75] Inventors: Kiyotaka Ohno, Fujisawa; Hisao Nishiyama, Toyohashi; Shintaro Nishio, Ebina, all of Japan

[73] Assignee: Toray Industries, Inc., Tokyo, Japan

[21] Appl. No.: 183,745

[22] Filed: Sep. 3, 1980

[30] Foreign Application Priority Data

Sep. 3, 1979 [JP] Japan ............................... 54-111709

[51] Int. Cl.$^3$ .................. A61K 31/557; A61K 31/34; C07D 307/93

[52] U.S. Cl. .................................... 424/263; 424/285; 424/275; 424/283; 260/345.7 P; 260/345.8 P; 260/345.9 P; 260/346.71; 542/429; 542/430; 546/269; 549/60

[58] Field of Search ................. 260/345.7 P, 345.8 P, 260/345.9 P, 346.71; 542/429, 430; 546/269; 549/60; 424/263, 275, 283, 285

[56] References Cited

PUBLICATIONS

Moncada et al., Nature, 263, 633 (1976).

*Primary Examiner*—Henry R. Jiles
*Assistant Examiner*—Bernard Dentz
*Attorney, Agent, or Firm*—Scully, Scott, Murphy & Presser

[57] ABSTRACT

Pharmaceutically useful compounds are 5,6,7-trinor-4,8-inter-m-phenylene PGI$_2$ derivatives such as 5,6,7-trinor-4,8-inter-m-phenylene-16,17,18,19,20-pentanor-15-phenyl PGI$_2$.

33 Claims, No Drawings

5,6,7-TRINOR-4,8-INTER-M-PHENYLENE PGI$_2$ DERIVATIVES

BACKGROUND OF THE INVENTION

This invention relates to prostaglandin I$_2$ derivatives.

Prostaglandin I$_2$ (PGI$_2$, prostacyclin) is a compound discovered in 1976 by J. R. Vane et al., which has called attention as a substance exerting potent platelet aggregation-inhibiting and aorta-contracting activities after having been biosynthesized from archidonic acid via an endo-peroxide (PGH$_2$) at the aortic wall [CdEN, Dec. 20, 1976, p. 17; S. Moncada, R. Gryglewski, S. Bunting and J. R. Vane, Nature, 263, 633 (1976)].

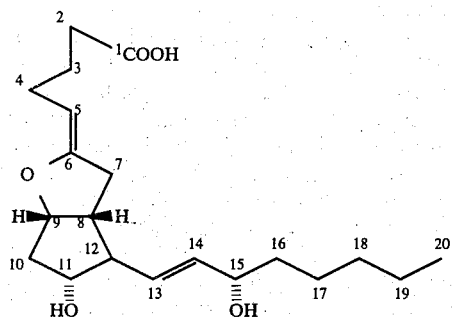

PGI$_2$

However, PGI$_2$ which has an exo-enol structure is extremely unstable even in neutral aqueous solution and is readily subjected to conversion to 6-oxo PGF$_1$ which has almost no physiological activities. Such instability of PGI$_2$ is a big obstacle to its use as a drug. PGI$_2$ is also metabolized quickly in the body and its physiological actions are not durable.

It is an object of this invention to overcome the disadvantages inherent in PGI$_2$.

Another object of this invention is to provide novel PGI$_2$ derivatives which are stable and possess platelet aggregation-inhibiting, hypotensive anti-ulcer and other activities.

Other objects and advantages of this invention will be apparent from the descriptions hereinbelow.

SUMMARY OF THE INVENTION

The above-mentioned objects of the invention are achieved by a compound of the formula

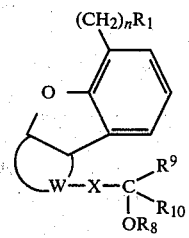

wherein R$_1$ is (a) carboxyl group, (b) its salt, (c) its ester, (d) its amide or (e) —CH$_2$OH, n is an integer from 1 to 3, W is (a) 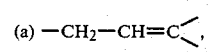

(b) 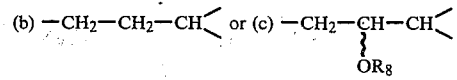

wherein R$_8$ is hydrogen, acyl of 1 to 12 carbon atoms, aroyl, tetrahydropyranyl, tetrahydrofuranyl or 1-ethoxyethyl, X is (a) —CH$_2$CH$_2$— or (b) 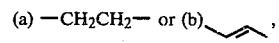, R$_9$ is (a) hydrogen or (b) alkyl of 1 to 4 carbon atoms,
R$_{10}$ is (a) straight alkyl of 4 to 12 carbon atoms, (b) 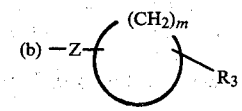

wherein Z is a valence bond or alkylene of 1 to 5 carbon atoms, m is an integer of from 5 to 12, R$_3$ is hydrogen or alkyl of 1 to 5 carbon atoms, or (c) —Z-Ar$_2$ wherein Z is as defined above, Ar$_2$ is phenyl, α-naphthyl, β-naphthyl or phenyl substituted by at least one chloro, bromo, fluoro, trifluoromethyl, alkyl of 1 to 4 carbon atoms, nitro, methoxy, phenyl or phenoxy.

DETAILED DESCRIPTION OF THE INVENTION

R$_1$ in the above-given general formula (I) is (a) carboxyl group, (b) its salt, (c) its ester, (d) its amide or (e) —CH$_2$OH, among which the groups (a)–(c) may be represented by —COOR$_2$ and the group (d) by 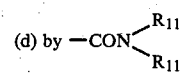.

As R$_2$ in —COOR$_2$ is illustratively mentioned the following:
(a) hydrogen or a pharmaceutical acceptable cation
(b) straight alkyl of 1 to 12 carbon atoms or branched alkyl of 3 to 12 carbon atoms,
(c)

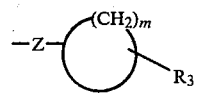

wherein Z is a valence bond or alkylene of 1 to 5 carbon atoms, m is an integer of 5 to 12 and R$_3$ is alkyl of 1 to 5 carbon atoms,
(d) —(CH$_2$CH$_2$O)$_l$CH$_3$ wherein l is an integer of 1 to 5,
(e) —Z-Ar$_1$ wherein Z is as defined above, Ar$_1$ is phenyl, α-naphthyl, β-naphthyl, 2-pyridyl, 3-pyridyl, 4-pyridyl, α-furyl, β-furyl, α-thienyl, β-thienyl or phenyl substituted by at least one chloro, bromo, fluoro, trifluoromethyl, alkyl of 1 to 4 carbon atoms, nitro, methoxy, phenyl, phenoxy,

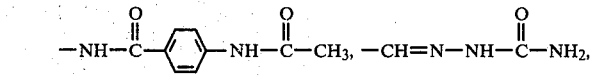

-continued $$-NH-\overset{O}{\underset{\|}{C}}-\underset{}{\bigcirc}, \; -NH-\overset{O}{\underset{\|}{C}}-CH_3 \; \text{or} \; -NH-\overset{O}{\underset{\|}{C}}-NH_2,$$

(f) $-C_lH_{2l}COOR_3$ wherein $R_3$ and $l$ are as defined above, (g) $-C_lH_{2l}N(R_3)_2$ wherein $R_3$ and $l$ are as defined above, (h)

$$-\underset{R_4}{\overset{}{\underset{|}{CH}}}-\overset{O}{\underset{\|}{C}}-R_5$$

wherein $R_4$ is hydrogen or benzoyl, $R_5$ is phenyl, p-bromophenyl, p-biphenyl, p-nitrophenyl, p-benzamidophenyl or 2-naphthyl, (i) $-ClH_2l-B$, wherein $l$ is as defined above, B is $$\diagdown_{R_3}\diagup, \; \diagdown\diagup_{R_3}, \; \diagdown\diagup\overset{R_3}{\underset{R_3}{\diagdown}}$$

or $-C\equiv C-R_6$ wherein $R_3$ is as defined above, $R_6$ is alkyl of 1 to 30 carbon atoms or aralykl of 7 to 30 carbon atoms, or (j)

$$-\underset{|}{\overset{CH_2-OR_7}{\underset{CH_2-OR_7}{CH}}}$$

wherein $R_7$ is alkyl of 1 to 30 carbon atoms or acyl of 1 to 30 carbon atoms.

As $R_{11}$ in $$-CON\diagdown_{R_{11}}^{R_{11}}$$

is illustratively mentioned the following: hydrogen, alkyl of 1 to 10 carbon atoms, cycloalkyl of 3 to 12 carbon atoms, phenyl, phenyl substituted by at least one chloro, bromo, fluoro, trifluoromethyl, alkyl of 1 to 4 carbon atoms, nitro, methoxy, phenyl, phenoxy, $$-NH-\overset{O}{\underset{\|}{C}}-\underset{}{\bigcirc}-NH-\overset{O}{\underset{\|}{C}}-CH_3, \; -CH=N-NH-\overset{O}{\underset{\|}{C}}-NH_2,$$

$$-NH-\overset{O}{\underset{\|}{C}}-\underset{}{\bigcirc}, \; -NH-\overset{O}{\underset{\|}{C}}-CH_3 \; \text{or} \; -NH-\overset{O}{\underset{\|}{C}}-NH_2,$$

aralkyl of 7 to 12 carbon atoms or $-SO_2R_{12}$ wherein $R_{12}$ has the same definition as $R_{11}$ excepting $-SO_2R_{12}$, both of $R_{11}$ may be same or different with the proviso that both of $R_{11}$ are not $-SO_2R_{12}$ simultaneously. More specifically, the cations wherein $R_2$ is a pharmaceutically acceptable cation include amine cations and quaternary ammonium cations. Particularly preferred metallic cations are those derived from alkali metals, for example, lithium, sodium and potassium and alkaline earth metals, for example, magnesium and calcium. In addition, these cations from other metals such as, for example, aluminum, zinc and iron are within the scope of this invention.

Pharmaceutically acceptable amine cations are those derived from primary, secondary or tertiary amines. Examples of the suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and similar aliphatic, alicyclic and heterocyclic amines containing up to about 18 carbon atoms, for example, 1-methylpiperidine, 4-ethylmorpholine, triisopropylpyrolidine, 2-methylpyrolidine, 4-dimethylpiperadine, 2-methylpiperidine and the like. Further examples are those amines containing water-soluble or hydrophilic groups such as, for example, mono-, di- and triethanolamines, ethyldiethylamine, N-butylethanolamine, 2-amino-1-butanol, 2-amino-2-ethyl-1,3-propanediol, tris(hydroxymethyl)aminomethane, N-phenylethanolamine, N-(p-tert-amylphenyl)diethanolamine, galactamine, N-methylglutamine, N-methylglucosamine, ephedrine phenylephrine, epinephrine, procaine and the like. Basic amino acids, specifically lysine, arginine and the like may also be mentioned.

As examples of $R_2$ which is straight-chain alkyl groups containing 1-12 carbon atoms may be mentioned methyl, ethyl, propyl, butyl, pentyl, hexyl, heptyl, octyl, dodecyl and the like. As examples of the branched alkyl groups containing 3-12 carbon atoms may be mentioned isopropyl, sec-butyl, t-butyl, 2-methylpentyl, 6-methylheptyl and the like.

Examples of $R_2$ and $R_{10}$ either or both of which are represented $$-Z-\underset{}{\bigcirc}\overset{(CH_2)_m}{\underset{R_3}{\diagdown}}$$

include cyclopentyl, cyclohexyl, cycloheptyl, cyclooctyl, cyclododecyl, cyclopentylmethyl, cyclohexylmethyl, cycloheptylmethyl, cyclododecylmethyl, cyclopentylethyl, cyclohexylethyl, cycloheptylethyl, cyclopentylpropyl, cyclohexylpropyl, cyclopentylbutyl, cyclohexylbutyl, cyclohexylpentyl, 2-methyl cyclopentyl, 3-methyl cyclopentyl, 2-methyl cyclohexyl, 3-methyl cyclohexyl, 4-methyl cyclohexyl, 2-methyl cycloheptyl, 3-methyl cycloheptyl, 4-methyl cycloheptyl, 4-methyl cyclooctyl, 2-ethyl cyclopentyl, 3-ethyl cyclopentyl, 2-ethyl cyclohexyl, 3-ethyl cyclohexyl, 4-ethyl cyclohexyl, 2-ethyl cycloheptyl, 2-ethyl cyclooctyl, 3-ethyl cyclooctyl, 2-methyl cyclopentylmethyl, 3-methyl cyclopentylmethyl, 2-methyl cyclohexylmethyl, 3-methyl cyclohexylmethyl, 4-methyl cyclohexylmethyl, 2-methyl cycloheptylmethyl, 3-methyl cycloheptylmethyl, 2-methyl cyclooctylmethyl, 2-(2-methyl cyclopentyl)ethyl, 2-(3-methyl cyclopentyl)ethyl, 2-(2-methyl cyclohexyl)ethyl, 2-(3-methyl cyclohexyl)ethyl, 2-(4-methyl cyclohexyl)ethyl, 2-(2-methyl cycloheptyl) ethyl, 2-(2-methyl cyclooctyl)ethyl, 3-(2-methyl cyclopentyl)propyl, 3-(3-methyl cyclopentyl)propyl, 3-(2-methyl cyclohexyl)propyl, 3-(3-methyl cyclohexyl)propyl, 3-(4-methyl cyclohexyl)propyl, 5-(2-methyl cyclopentyl)pentyl, 2-ethyl cyclopentylmethyl, 3-ethyl cyclopentylmethyl, 2-ethyl cyclohexylmethyl, 3-ethyl cyclohexylmethyl, 4-ethyl cyclohexylmethyl, 2-ethyl cycloheptylmethyl, 3-methyl cycloheptylmethyl, 2-ethyl cyclooctylmethyl, 2-(2-ethyl cyclopentyl)ethyl, 2-(3-ethyl cyclopentyl)ethyl, 2-(4-ethyl cyclohexyl)ethyl, 2-(2-ethyl cycloheptyl)ethyl, 2-(2-ethyl cyclooctyl)ethyl, 3-(2-ethyl cyclopentyl)propyl, 3-(3-ethyl cyclopentyl)propyl, 3-(2-ethyl cyclohexyl)propyl, 3-(3-ethyl cyclohexyl)propyl, 3-(4-ethyl cyclohexyl)propyl, 5-(2-ethyl cyclopentyl)pentyl, 5-(2-ethyl cyclopentyl)pentyl and the like.

Examples of $R_2$ which is —$(CH_2CH_2O)_iCH_3$ include 2-methoxyethyl, 2-(2-methoxyethoxy)ethyl, 2-[2-(methoxyethoxy)ethoxy]ethyl and the like.

Examples of $R_2$ which is —$C_iH_{2i}COOR_3$ include carbomethoxymethyl, (1-carbomethoxy)ethyl, carboethoxymethyl, carbopropoxymethyl, carbobutoxymethyl, (3-carbomethoxy)propyl, (3-carboethoxy)propyl, (3-carbopropoxy)propyl, (3-carbobutoxy)propyl and the like. $R_3$ is hydrogen, methyl, ethyl, propyl, butyl or pentyl.

As examples of $R_2$ which is

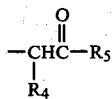

may be mentioned phenacyl, p-bromo phenacyl, p-phenyl phenacyl, p-nitro phenacyl, p-benzoylamino phenacyl, β-naphthoylmethyl, dibenzoylmethyl and the like. As examples of $R_2$ which is —$C_iH_{2i}B$-$R_3$ may be mentioned

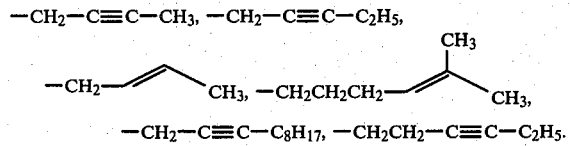

As specific examples of $R_2$ which is

may be mentioned 1,3-dimethoy-2-propyl, 1,3-diethoxy-2-propyl, 1-methoxy-3-stearoyloxy-2-propyl, 1,3-diacetoxy-2-propyl and the like.

As specific examples of $Ar_1$ which is substituted phenyl may be mentioned p-chloro phenyl, p-bromo phenyl, p-fluoro phenyl, m-chloro phenyl, m-fluoro phenyl, 3,4-dichloro phenyl, p-(trifluoromethyl) phenyl, p-tolyl, 3,4-dimethyl phenyl, p-anisyl, 3,4-dimethoxy phenyl, 4-phenoxy phenyl, p-benzoylamino phenyl, p-acetamino phenyl, p-carbamoylamino phenyl, p-nitro phenyl and the like.

As specific examples of —Z-$Ar_2$ may be mentioned phenyl, p-chloro phenyl, p-bromo phenyl, p-fluoro phenyl, 3,4-dichloro phenyl, m-fluoro phenyl, m-trifluoromethyl phenyl, p-trifluoromethyl phenyl, p-nitro phenyl, p-anisyl, 3,4-dimethoxy phenyl, p-tolyl, m-tolyl, o-tolyl, p-ethyl phenyl, p-propyl phenyl, p-butyl phenyl, 3,4-dimethyl phenyl, 2,4-dimethyl phenyl, 3-chloro-4-methyl phenyl, 3-fluoro-4-methyl phenyl, 4-biphenyl, p-phenoxy phenyl, p-phenoxy-3-chlorophenyl, benzyl, p-chloro benzyl, m-chloro benzyl, p-methoxy benzyl, o-methoxy benzyl, p-methyl benzyl, p-ethyl benzyl, p-propyl benzyl, p-nitro benzyl, 3,4-dichlro benzyl, α-methyl benzyl, α,α'-dimethyl benzyl, phenethyl, p-chloro phenethyl, p-bromo phenethyl, p-fluoro phenethyl, m-chloro phenethyl, m-fluoro phenethyl, o-chloro phenethyl, p-methyl phenethyl, p-methoxy phenethyl, 3,4-dimethoxy phenethyl, p-ethyl phenethyl, α-methyl phenethyl, β-methyl phenethyl, α,α'-dimethyl phenethyl, β,β'-dimethyl phenethyl, 3-phenyl propyl, 3-(p-chloro phenyl)propyl, 3-(p-fluoro phenyl)propyl, 3-(p-bromo phenyl)propyl, 3-(m-chloro phenyl)propyl, 3-(3,4-dichloro phenyl) propyl, 3-(p-tolyl)propyl, 3-(p-ethyl phenyl)propyl, 4-phenyl butyl, 4-(p-chloro phenyl)butyl, 4-(3,4-dichloro phenyl)butyl, 4-(p-tolyl) butyl, 5-phenyl pentyl and the like.

Examples of the alkyl containing 1-10 carbon atoms which is represented by $R_{11}$ or $R_{12}$ includes methyl, ethyl, propyl, butyl, octyl, decyl and the like. As examples of the cycloalkyl containing 3-12 carbon atoms which represents $R_{11}$ or $R_{12}$ may be mentioned cyclopropyl, cyclopentyl, cyclohexyl, cyclooctyl, cyclodecyl and the like. Examples of the substituted phenyl which is represented by $R_{11}$ or $R_{12}$ are the same as illustrated for $Ar_2$ which represents substituted phenyl. As specific examples of the aralkyl containing 7-12 carbon atoms which is represented by $R_{11}$ or $R_{12}$ may be mentioned benzyl, phenetyl, 3-phenylpropyl, p-methyl benzyl, p-ethyl benzyl, p-propyl benzyl, 3,4-dimethyl benzyl and the like.

Specific examples of $R_8$ which represents acyl containing 1-12 carbon atoms include acetyl, propionyl, butyroyl, octanoyl, dedecanoyl and the like. As specific examples of $R_8$ which represents aroyl containing 6-12 carbon atoms may be mentioned benzoyl, phenyl acetyl, 3-phenyl propionyl, p-phenyl benzoyl, α-naphthoyl, β-naphthoyl and the like.

As specific examples of $R_7$ which represents straight-chain alkyl containing 1-30 carbon atoms may be mentioned methyl, ethyl, propyl, butyl, pentyl, hexyl, octyl, hexadecanyl, octaicosanyl and the like.

Examples of $R_{10}$ which represents straight-chain alkyl containing 4-12 carbon atoms include n-butyl, n-amyl, n-hexyl, n-heptyl, n-octyl, n-decyl, n-dodecyl and the like.

The compounds of the invention represented by the aforementioned general formula (I) are $PGI_2$ derivatives of a novel structure in which the exo-enol ether moiety characteristic of $PGI_2$ is transformed into an inter-m-phenylene moiety.

These novel compounds of the aforementioned general formula (I) produced according to this invention are characterized by much improved stabilities as compared with $PGI_2$. In fact, the compounds of the general formula (I) are highly stable in aqueous solution and are very durable in in vivo physiological action. Moreover, these general formula (I) compounds have advantages for pharmaceutical application in that their physiological activities are selective from those of $PGI_2$ which are in too many directions.

The compounds of the general formula (I) produced by the invention are named according to the nomenclature for prostaglandins and prostacyclin analogs proposed by N. A. Nelson et al. [N. A. Nelson, J. Med. Che., 17, 911 (1974) and R. A. Johnson, D. R. Morton and N. A. Nelson, Prostaglandins, 15, 737 (1978)]. The basic compounds in which the exo-enol moiety of $PGI_2$ is transformed into an inter-m-phenylene are represented by the following formula which is numbered as shown in the figure and named 5,6,7-trinor-4,8-inter-m-phenylene PGI$_2$.

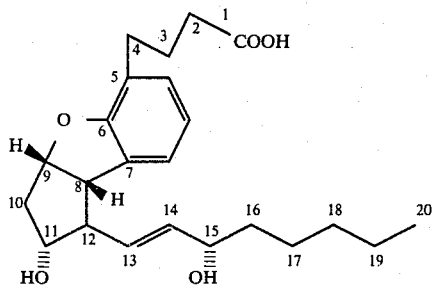

According to the nomenclature, the compound of the below-given formula covered by this invention is named 5,6,7-trinor-4,8-inter-m-phenylene-16,17,18,19,20-pentanor-15-cyclohexyl PGI$_2$.

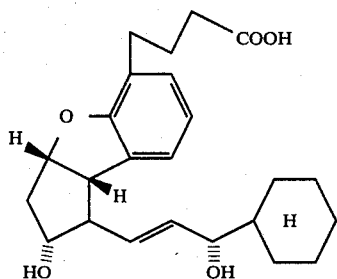

Illustrative compounds of the aforementioned general formula (I) named according to the above-cited nomenclature are listed below.

The compounds wherein R$_1$ is COOR$_2$ in which R$_2$ is hydrogen, n is 3, W is

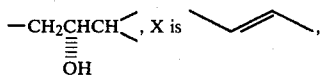

R$_9$ is hydrogen and R$_{10}$ is

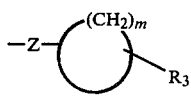

are illustrated by but not limited to:
5,6,7-trinor-4,8-inter-m-phenylene-16,17,18,19,20-pentanor-15-cyclopentyl PGI$_2$,
5,6,7-trinor-4,8-inter-m-phenylene-16,17,18,19,20-pentanor-15-(2-methyl cyclopentyl) PGI$_2$,
5,6,7-trinor-4,8-inter-m-phenylene-16,17,18,19,20-pentanor-15-(3-methyl cyclopentyl) PGI$_2$,
5,6,7-trinor-4,8-inter-m-phenylene-16,17,18,19,20-pentanor-15-(3-ethyl cyclopentyl) PGI$_2$,
5,6,7-trinor-4,8-inter-m-phenylene-17,18,19,20-tetranor-16-cyclopentyl PGI$_2$,
5,6,7-trinor-4,8-inter-m-phenylene-17,18,19,20-tetranor-16-(3-methyl cyclopentyl) PGI$_2$,
5,6,7-trinor-4,8-inter-m-phenylene-17,18,19,20-tetranor-16-(3-ethyl cyclopentyl) PGI$_2$,
5,6,7-trinor-4,8-inter-m-phenylene-17,18,19,20-tetranor-16-(3-n-propyl cyclopentyl) PGI$_2$,
5,6,7-trinor-4,8-inter-m-phenylene-16,17,18,19,20-pentanor-15-cyclohexyl PGI$_2$,
5,6,7-trinor-4,8-inter-m-phenylene-16,17,18,19,20-pentanor-15-(2-methyl cyclohexyl) PGI$_2$,
5,6,7-trinor-4,8-inter-m-phenylene-16,17,18,19,20-pentanor-15-(3-methyl cyclohexyl) PGI$_2$,
5,6,7-trinor-4,8-inter-m-phenylene-16,17,18,19,20-pentanor-15-(4-methyl cyclohexyl) PGI$_2$,
5,6,7-trinor-4,8-inter-m-phenylene-17,18,19,20-tetranor-16-cyclohexyl PGI$_2$,
5,6,7-trinor-4,8-inter-m-phenylene-17,18,19,20-tetranor-16-(3-methyl cyclohexyl) PGI$_2$,
5,6,7-trinor-4,8-inter-m-phenylene-17,18,19,20-tetranor-16-(4-methyl cyclohexyl) PGI$_2$,
5,6,7-trinor-4,8-inter-m-phenylene-17,18,19,20-tetranor-16-(4-ethyl cyclohexyl) PGI$_2$,
5,6,7-trinor-4,8-inter-m-phenylene-16,17,18,19,20-pentanor-15-cycloheptyl PGI$_2$,
5,6,7-trinor-4,8-inter-m-phenylene-16,17,18,19,20-pentanor-15-cyclooctyl PGI$_2$,
5,6,7-trinor-4,8-inter-m-phenylene-16,17,18,19,20-pentanor-15-cyclododecyl PGI$_2$ and the like.

The compounds wherein R$_1$ is COOR$_2$ in which R$_2$ is hydrogen, n-is 3, W is

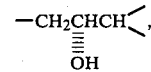

X is —CH$_2$CH$_2$—, R$_9$ is hydrogen and R$_{10}$ is

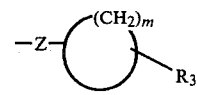

or —Z—Ar$_2$ are illustrated by but not limited to:
5,6,7-trinor-4,8-inter-m-phenylene-13,14-dihydro-16,17,18,19,20-pentanor-15-cyclopentyl PGI$_2$,
5,6,7-trinor-4,8-inter-m-phenylene-13,14-dihydro-17,18,19,20-tetranor-16-cyclopentyl PGI$_2$,
5,6,7-trinor-4,8-inter-m-phenylene-13,14-dihydro-16,17,18,19,20-pentanor-15-phenyl PGI$_2$
5,6,7-trinor-4,8-inter-m-phenylene-13,14-dihydro-16,17,18,19,20-pentanor-15-p-tolyl PGI$_2$,
5,6,7-trinor-4,8-inter-m-phenylene-13,14-dihydro-16,17,18,19,20-pentanor-15-cyclohexyl PGI$_2$,
5,6,7-trinor-4,8-inter-m-phenylene-13,14-dihydro-17,18,19,20-tetranor-16-cyclohexyl PGI$_2$,
5,6,7-trinor-4,8-inter-m-phenylene-13,14-dihydro-17,18,19,20-tetranor-16-(4-methyl cyclohexyl) PGI$_2$ and the like.

The compounds wherein R$_1$ is COOR$_2$ in which R$_2$ is hydrogen, n is 3, W is

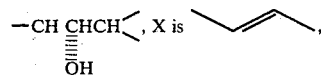

R$_9$ is hydrogen and R$_{10}$ is —Z—Ar$_2$ in which Z is a valence bond are illustrated by but not limited to:
5,6,7-trinor-4,8-inter-m-phenylene-16,17,18,19,20-pentanor-15-phenyl PGI$_2$,
5,6,7-trinor-4,8-inter-m-phenylene-16,17,18,19,20-pentanor-15-(p-tolyl) PGI$_2$, 5,6,7-trinor-4,8-inter-m-phenylene-16,17,18,19,20-pentanor-15-(m-tolyl) PGI₂,
5,6,7-trinor-4,8-inter-m-phenylene-16,17,18,19,20-pentanor-15-(m-trifluoromethyl phenyl) PGI₂,
5,6,7-trinor-4,8-inter-m-phenylene-16,17,18,19,20-pentanor-15-(3,4-dimethoxy phenyl) PGI₂,
5,6,7-trinor-4,8-inter-m-phenylene-16,17,18,19,20-pentanor-15-(3,4-dichloro phenyl) PGI₂,
5,6,7-trinor-4,8-inter-m-phenylene-16,17,18,19,20-pentanor-15-(p-ethyl phenyl) PGI₂,
5,6,7-trinor-4,8-inter-m-phenylene-16,17,18,19,20-pentanor-15-(m-ethyl phenyl) PGI₂,
5,6,7-trinor-4,8-9nter-m-phenylene-16,17,18,19,20-pentanor-15-(p-chloro phenyl) PGI₂,
5,6,7-trinor-4,8-inter-m-phenylene-16,17,18,19,20-pentanor-15-(m-bromo phenyl) PGI₂,
5,6,7-trinor-4,8-inter-m-phenylene-16,17,18,19,20-pentanor-15-(p-bromo phenyl) PGI₂,
5,6,7-trinor-4,8-inter-m-phenylene-16,17,18,19,20-pentanor-15-(m-fluoro phenyl) PGI₂,
5,6,7-trinor-4,8-inter-m-phenylene-16,17,18,19,20-pentanor-15-(p-fluoro phenyl) PGI₂,
5,6,7-trinor-4,8-inter-m-phenylene-16,17,18,19,20-pentanor-15-(o-methoxy phenyl) PGI₂,
5,6,7-trinor-4,8-inter-m-phenylene-16,17,18,19,20-pentanor-15-(m-methoxy phenyl) PGI₂,
5,6,7-trinor-4,8-inter-m-phenylene-16,17,18,19,20-pentanor-15-(p-methoxy phenyl) PGI₂,
5,6,7-trinor-4.8-inter-m-phenylene-16,17,18,19,20-pentanor-15-(p-biphenyl) PGI₂,
5,6,7-trinor-4,8-inter-m-phenylene-16,17,18,19,20-pentanor-15-(p-phenoxy phenyl) PGI₂,
5,6,7-trinor-4,8-inter-m-phenylene-16,17,18,19,20-pentanor-15-(α-naphthyl) PGI₂,
5,6,7-trinor-4,8-inter-m-phenylene-16,17,18,19,20-pentanor-15-(β-naphthyl) PGI₂ and the like.

The compounds wherein $R_1$ is $COOR_2$ in which $R_2$ is hydrogen, n is 3, W is

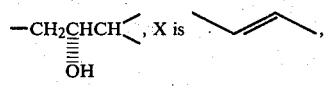

$R_9$ is hydrogen and $R_{10}$ is —Z-Ar in which Z represents —CH₂—, —CH₂CH₂— or —CH₂CH₂CH₂— are illustrated by but not limited to:
5,6,7-trinor-4,8-inter-m-phenylene-17,18,19,20-tetranor-16-phenyl PGI₂,
5,6,7-trinor-4,8-inter-m-phenylene-17,18,19,20-tetranor-16-(p-tolyl) PGI₂,
5,6,7-trinor-4,8-inter-m-phenylene-17,18,19,20-tetranor-16-(m-tolyl) PGI₂,
5,6,7-trinor-4,8-inter-m-phenylene-17,18,19,20-tetranor-16-(p-ethyl phenyl) PGI₂,
5,6,7-trinor-4,8-inter-m-phenylene-17,18,19,20-tetranor-16-(m-ethyl phenyl) PGI₂,
5,6,7-trinor-4,8-inter-m-phenylene-17,18,19,20-tetranor-16-(m-chloro phenyl) PGI₂,
5,6,7-trinor-4,8-inter-m-phenylene-17,18,19,20-tetranor-16-(p-chloro phenyl) PGI₂,
5,6,7-trinor-4,8-inter-m-phenylene-17,18,19,20-tetranor-16-(m-bromo phenyl) PGI₂,
5,6,7-trinor-4,8-inter-m-phenylene-17,18,19,20-tetranor-16-(p-bromo phenyl) PGI₂,
5,6,7-trinor-4,8-inter-m-phenylene-17,18,19,20-tetranor-16-(p-fluoro phenyl) PGI₂,
5,6,7-trinor-4,8-inter-m-phenylene-17,18,19,20-tetranor-16-(m-methoxy phenyl) PGI₂,
5,6,7-trinor-4,8-inter-m-phenylene-17,18,19,20-tetranor-16-(p-methoxy phenyl) PGI₂,
5,6,7-trinor-4,8-inter-m-phenylene-17,18,19,20-tetranor-16-(o-methoxy phenyl) PGI₂,
5,6,7-trinor-4,8-inter-m-phenylene-17,18,19,20-tetranor-16-(p-phenyl phenyl) PGI₂,
5,6,7-trinor-4,8-inter-m-phenylene-17,18,19,20-tetranor-16-(p-phenoxy phenyl) PGI₂,
5,6,7-trinor-4,8-inter-m-phenylene-17,18,19,20-tetranor-16-(α-naphthyl) PGI₂,
5,6,7-trinor-4,8-inter-m-phenylene-17,18,19,20-tetranor-16-(β-naphthyl) PGI₂,
5,6,7-trinor-4,8-inter-m-phenylene-18,19,20-trinor-17-phenyl PGI₂,
5,6,7-trinor-4,8-inter-m-phenylene-18,19,20-trinor-17-(p-tolyl) PGI₂,
5,6,7-trinor-4,8-inter-m-phenylene-18,19,20-trinor-17-(m-tolyl) PGI₂,
5,6,7-trinor-4,8-inter-m-phenylene-18,19,20-trinor-17-(p-ethyl phenyl) PGI₂,
5,6,7-trinor-4,8-inter-m-phenylene-18,19,20-trinor-17-(m-ethyl phenyl) PGI₂,
5,6,7-trinor-4,8-inter-m-phenylene-18,19,20-trinor-17-(p-chloro phenyl) PGI₂,
5,6,7-trinor-4,8-inter-m-phenylene-18,19,20-trinor-17-(m-chloro phenyl) PGI₂,
5,6,7-trinor-4,8-inter-m-phenylene-18,19,20-trinor-17-(p-bromo phenyl) PGI₂,
5,6,7-trinor-4,8-inter-m-phenylene-18,19,20-trinor-17-(m-bromo phenyl) PGI₂,
5,6,7-trinor-4,8-inter-m-phenylene-18,19,20-trinor-17-(m-fluoro phenyl) PGI₂,
5,6,7-trinor-4,8-inter-m-phenylene-18,19,20-trinor-17-(p-fluoro phenyl) PGI₂,
5,6,7-trinor-4,8-inter-m-phenylene-18,19,20-trinor-17-(p-methoxy phenyl) PGI₂,
5,6,7-trinor-4,8-inter-m-phenylene-18,19,20-trinor-17-(m-methoxy phenyl) PGI₂,
5,6,7-trinor-4,8-inter-m-phenylene-18,19,20-trinor-17-(o-methoxy phenyl) PGI₂,
5,6,7-trinor-4,8-inter-m-phenylene-18,19,20-trinor-17-(p-phenyl phenyl) PGI₂,
5,6,7-trinor-4,8-inter-m-phenylene-18,19,20-trinor-17-(p-phenoxy phenyl) PGI₂,
5,6,7-trinor-4,8-inter-m-phenylene-18,19,20-trinor-17-(α-naphthyl) PGI₂,
5,6,7-trinor-4,8-inter-m-phenylene-18,19,20-trinor-17-(β-naphthyl) PGI₂,
5,6,7-trinor-4,8-inter-m-phenylene-19,20-dinor-18-phenyl PGI₂,
5,6,7-trinor-4,8-inter-m-phenylene-19,20-dinor-18-(p-tolyl) PGI₂,
5,6,7-trinor-4,8-inter-m-phenylene-19,20-dinor-18-(p-chloro phenyl) PGI₂,
5,6,7-trinor-4,8-inter-m-phenylene-19,20-dinor-18-(m-chloro phenyl) PGI₂,
5,6,7-trinor-4,8-inter-m-phenylene-19,20-dinor-18-(p-ethyl phenyl) PGI₂,
5,6,7-trinor-4,8-inter-m-phenylene-19,20-dinor-18-(m-ethyl phenyl) PGI₂,
5,6,7-trinor-4,8-inter-m-phenylene-19,20-dinor-18-(p-bromo phenyl) PGI₂,
5,6,7-trinor-4,8-inter-m-phenylene-19,20-dinor-18-(m-bromo phenyl) PGI₂,
5,6,7-trinor-4,8-inter-m-phenylene-19,20-dinor-18-(p-fluoro phenyl) PGI₂, 5,6,7-trinor-4,8-inter-m-phenylene-19,20-dinor-18-(m-fluoro phenyl) PGI₂,
5,6,7-trinor-4,8-inter-m-phenylene-19,20-dinor-18-(o-methoxy phenyl) PGI₂,
5,6,7-trinor-4,8-inter-m-phenylene-19,20-dinor-18-(m-methoxy phenyl) PGI₂,
5,6,7-trinor-4,8-inter-m-phenylene-19,20-dinor-18-(p-methoxy phenyl) PGI₂,
5,6,7-trinor-4,8-inter-m-phenylene-19,20-dinor-18-(p-biphenyl) PGI₂,
5,6,7-trinor-4,8-inter-m-phenylene-19,20-dinor-18-(p-phenoxy phenyl) PGI₂,
5,6,7-trinor-4,8-inter-m-phenylene-19,20-dinor-18-(α-naphthyl) PGI₂,
5,6,7-trinor-4,8-inter-m-phenylene-19,20-dinor-18-(β-naphthyl) PGI₂ and the like.

The compounds wherein R₁ is COOR₂ in which R₂ is hydrogen, n is 3, W is

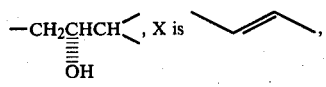

R₉ is methyl and R₁₀ is

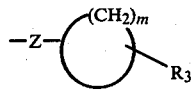

or —Z—Ar₂ are illustrated by but not limited to:
5,6,7-trinor-4,8-inter-m-phenylene-16,17,18,19,20-pentanor-15-cyclopentyl-15-methyl PGI₂,
5,6,7-trinor-4,8-inter-m-phenylene-16,17,18,19,20-pentanor-15-cyclohexyl-15-methyl PGI₂,
5,6,7-trinor-4,8-inter-m-phenylene-17,18,19,20-tetranor-16-cyclopentyl-15-methyl PGI₂,
5,6,7-trinor-4,8-inter-m-phenylene-17,18,19,20-tetranor-16-cyclohexyl-15-methyl PGI₂,
5,6,7-trinor-4,8-inter-m-phenylene-16,17,18,19,20-pentanor-15-methyl-15-phenyl PGI₂,
5,6,7-trinor-4,8-inter-m-phenylene-16,17,18,19,20-pentanor-15-methyl-15-(p-tolyl) PGI₂,
5,6,7-trinor-4,8-inter-m-phenylene-16,17,18,19,20-pentanor-15-(p-chloro phenyl)-15-methyl PGI₂,
5,6,7-trinor-4,8-inter-m-phenylene-16,17,18,19,20-pentanor-15-(p-bromo phenyl)-15-methyl PGI₂,
5,6,7-trinor-4,8-inter-m-phenylene-17,18,19,20-tetranor-15-methyl-16-phenyl PGI₂,
5,6,7-trinor-4,8-inter-m-phenylene-18,19,20-trinor-15-methyl-17-phenyl PGI₂,
5,6,7-trinor-4,8-inter-m-phenylene-16,17,18,19,20-pentanor-15-(p-fluoro phenyl) PGI₂,
5,6,7-trinor-4,8-inter-m-phenylene-16,17,18,19,20-pentanor-15-(p-methoxy phenyl)-15-methyl PGI₂,
5,6,7-trinor-4,8-inter-m-phenylene-16,17,18,19,20-pentanor-15-methyl-15-(α-naphthyl) PGI₂ and the like.

The compounds wherein n is 3, W is

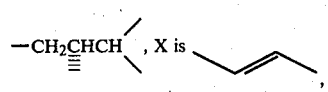

R₉ is hydrogen, R₁₀ is cyclohexyl and R₁ is COOR₂ in which R₂ represents straight or branched-chain alkyl containing 1–12 carbon atoms,

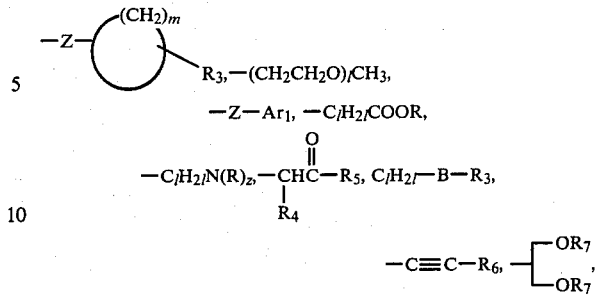

etc. are illustrated by but not limited to:
5,6,7-trinor-4,8-inter-m-phenylene-16,17,18,19,20-pentanor-15-cyclohexyl PGI₂ methyl ester; the following esters of 5,6,7-trinor-4,8-inter-m-phenylene-16,17,18,19,20-pentanor-15-cyclohexyl PGI₂, namely, ethyl ester, n-propyl ester, iso-propyl ester, sec-butyl ester, cyclopentyl ester, cyclohexyl ester, cyclopentylmethyl ester, cyclohexylmethyl ester, 2-methoxy ethyl ester, 2-(2-methoxy ethyl) ethyl ester, 2-[2-(2-methoxy ethoxy] ethyl ester, phenyl ester, benzyl ester, α-naphthyl ester, β-naphthyl ester, 2-pyridyl ester, 3-pyridyl ester, α-furyl ester, α-thienyl ester, p-chloro phenyl ester, p-bromo phenyl ester, p-trifluoromethyl phenyl ester, p-tolyl ester, p-methoxy phenyl ester, p-biphenyl ester, p-phenoxy phenyl ester, p-benzamide phenyl ester, p-acetamide phenyl ester, methoxycarbonylmethyl ester, ethoxycarbonylmethyl ester, 2-(methoxycarbonyl) ethyl ester, 2-(ethoxycarbonyl)ethyl ester, 2-(diethylamino) ethyl ester, phenacyl ester, p-bromo phenacyl ester, propargyl ester, di(methoxyethyl) methyl ester, di(ethoxyethyl) ethyl ester; 5,6,7-trinor-4,8-inter-m-phenylene-16,17,18,19,20-pentanor-15-phenyl PGI₂ methyl ester; the following esters of 5,6,7-trinor-4,8-inter-m-phenylene-16,17,18,19,20-pentanor-15-phenyl PGI₂, namely, ethyl ester, n-propyl ester, iso-propyl ester, sec-butyl ester, cyclopentyl ester, cyclohexyl ester, cyclopentylmethyl ester, cyclohexylmethyl ester, 2-methoxy ethyl ester, 2-(2-methoxyethoxy) ethyl ester, 2-[2-(2-methoxyethoxy) ethoxy] ethyl ester, phenyl ester, benzyl ester, α-naphthyl ester, β-naphthyl ester, 2-pyridyl ester, 3-pyridyl ester, α-furyl ester, α-thienyl ester, p-chloro phenyl ester, p-bromo phenyl ester, p-trifluoromethyl phenyl ester, p-tolyl ester, p-methoxy phenyl ester, p-biphenyl ester, p-phenoxy phenyl ester, p-benzamide phenyl ester, p-acetamide phenyl ester, methoxycarbonylmethyl ester, ethoxycarbonylmethyl ester, 2-(methoxycarbonyl) ethyl ester, 2-(ethoxycarbonyl) ethyl ester, 2-(diethylamino) ethyl ester, phenacyl ester, p-bromo phenacyl ester, propynyl ester, di(methoxymethyl) methyl ester, di(ethoxymethyl) methyl ester and the like. The compounds wherein n is 3, W is

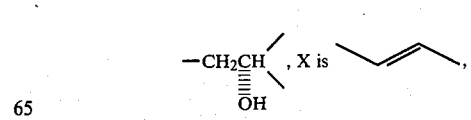

R₉ is hydrogen, R₁₀ is cyclohexyl or phenyl and R₁ is CH₂OH or

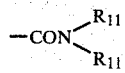

are illustrated by but not limited to:
5,6,7-trinor-4,8-inter-m-phenylene-16,17,18,19,20-pentanor-15-cyclohexyl-2-decarboxy-2-hydroxymethyl PGI$_2$, 5,6,7-trinor-4,8-inter-m-phenylene-16,17,18,19,20-pentanor-15-phenyl-2-decarboxy-2-hydroxymethyl PGI$_2$, 5,6,7-trinor-4,8-inter-m-phenylene-16,17,18,19,20-pentanor-15-phenyl PGI$_2$ amide; the following amide derivatives of 5,6,7-trinor-4,8-inter-m-phenylene-16,17,18,19,20-pentanor-15-phenyl PGI$_2$, namely, N-methyl amide, N-ethyl amide, N,N-dimethyl amide, N,N-diethyl amide, N-iso-propyl amide, N-n-butyl amide, N-phenyl amide, N,N-diphenyl amide, N-benzyl amide, N-methyl, N-phenyl amide, N-methyl, N-benzyl amide, N-phenetyl amide, N-(p-toluenesulfonyl) amide, N-butanesulfonyl amide, N-methanesulfonyl amide, N-ethanesulfonyl amide, N-propanesulfonyl amide, 5,6,7-trinor-4,8-inter-m-phenylene-16,17,18,19,20-pentanor-15-cyclohexyl PGI$_2$ N-methyl amide; the following amide derivatives of 5,6,7-trinor-4,8-inter-m-phenylene-16,17,18,19,20-pentanor-15-cyclohexyl PGI$_2$, namely, N-ethyl amide, N,N-dimethyl amide, N,N-diethyl amide, N-iso-propyl amide, N-n-butyl amide, N-phenyl amide, N,N-diphenyl amide, N-benzyl amide, N-methyl, N-phenyl amide, N-methyl, N-benzyl amide, N-phenetyl amide, N-benzenesulfonyl amide, N-(p-toluenesulfonyl) amide, N-methanesulfonyl amide, N-ethanesulfonyl amide, N-propanesulfonyl amide, N-butanesulfonyl amide, N-cyclohexylsulfonyl amide, benzylsulfonyl amide and the like.

The compounds of the aforementioned general formula (I) include d and l isomers and mixtures of the d and l isomers. As described below, the optically active d or l compounds can be produced by the same routes as those shown for the production of dl isomer using as the starting material an optically active compound.

The processes by which the compounds of the above-mentioned general formula (I) according to the present invention are produced are shown in Charts to K. More particularly, the compounds (VII) wherein R$_1$ is COOR$_2$ in which R$_2$ is hydrogen, W is

and R$_9$ is hydrogen except for those wherein Ar$_2$ is phenyl substituted with electron-donating groups (methyl, ethyl or methoxy) for the R$_{10}$ representing —Z—Ar$_2$ in which Z represents a valence bond can be produced by the route shown in Chart A.

CHART A (CH$_2$)$_n$CH$_2$OTHP (II)

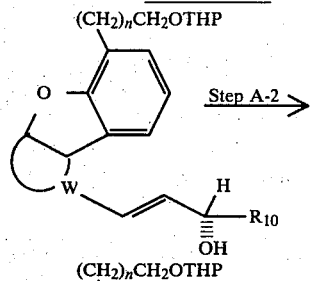

-continued
CHART A (CH$_2$)$_n$CH$_2$OTHP (III)

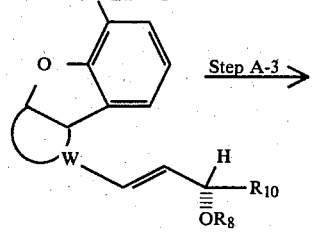

(CH$_2$)$_n$CH$_2$OTHP (IV)

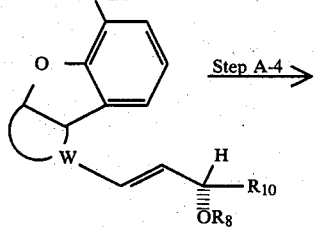

(CH$_2$)$_n$CHOH (V)

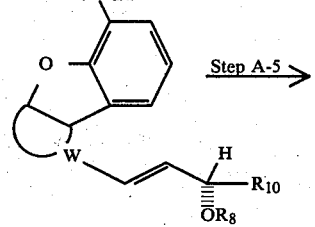

(CH$_2$)$_n$COOH (VI)

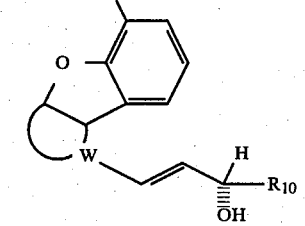

(CH$_2$)$_n$COOH (VII)

The compounds wherein R$_1$ is COOR$_2$ in which R$_2$ is hydrogen, X is

and R$_9$ is hydrogen but, more specifically, R$_{10}$ represents —Z—Ar$_2$ in which Z represents a valence bond and Ar$_2$ is phenyl substituted with electron-donating groups and W is

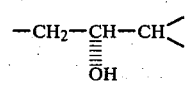

can be prepared by the route shown in Chart B.

The compounds wherein $R_1$ is $COOR_2$ in which $R_2$ is hydrogen, X is

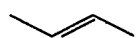

and $R_{10}$ represents —Z—$Ar_2$ in which Z represents a valence bond and $Ar_2$ represents phenyl substituted with electron-donating groups and W is

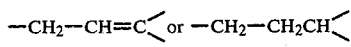

can also be produced by the route of Chart B, for which the steps B-2 and B-7 may be omitted.

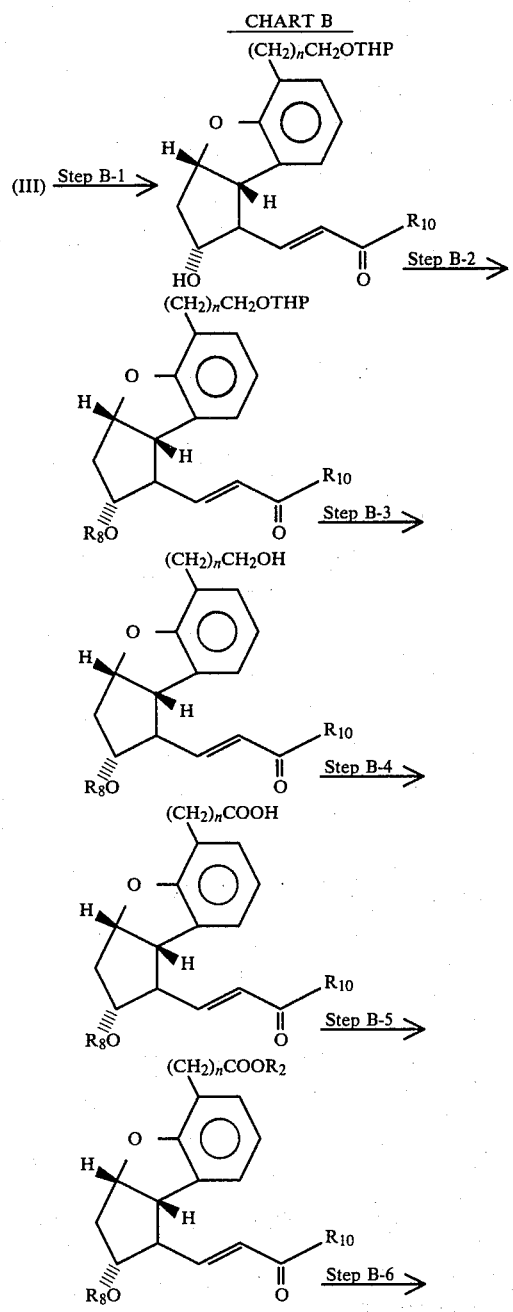

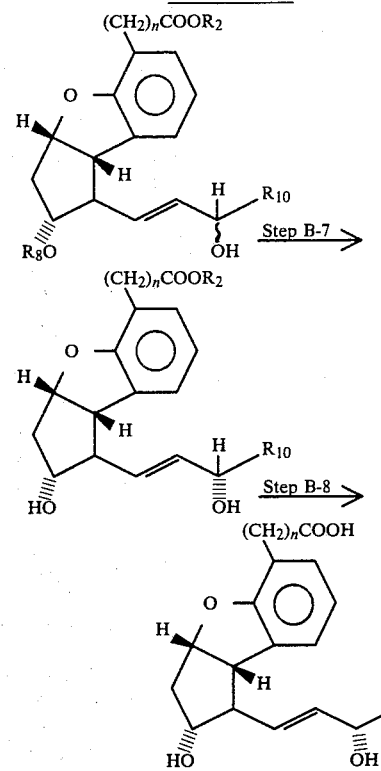

The compounds (XVII) wherein $R_1$ is $COOR_2$ in which $R_2$ is an ester radical instead of hydrogen and pharmaceutically acceptable cations are produced by the esterification step shown in Chart C.

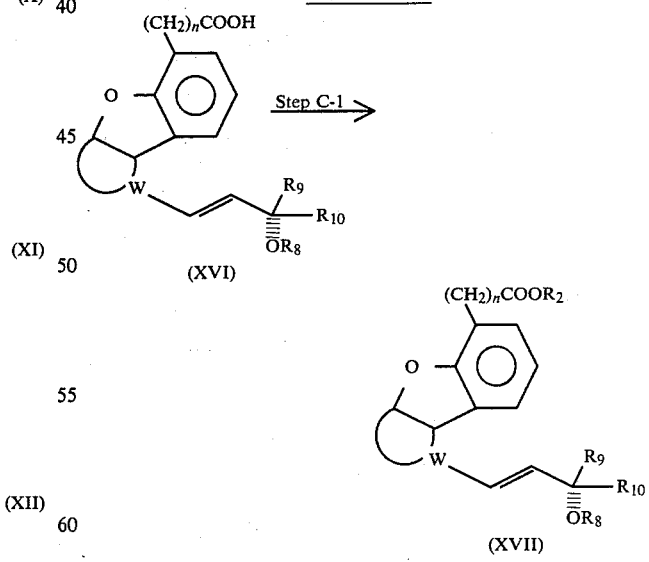

The compounds wherein $R_1$ is

are produced by the step shown in Chart D provided that $R_{11}$ is other than $-SO_2R_{12}$.

CHART D

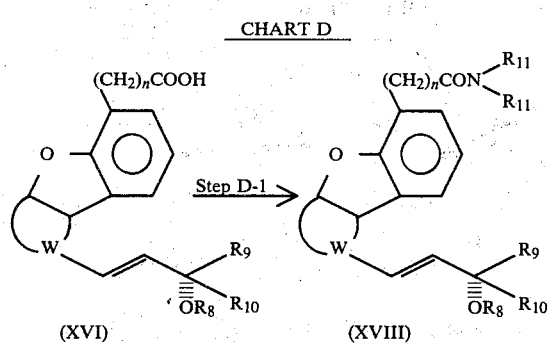

(XVI)           (XVIII)

The compounds (XIX) wherein $R_1$ is $CH_2OH$, X is

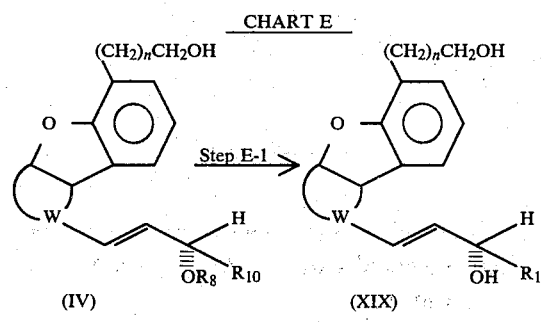

and $R_9$ is hydrogen (provided that $R_8$ other than hydrogen) are produced by the step shown in Chart E.

CHART E (IV)           (XIX)

The compounds wherein X is $-CH_2-CH_2-$ are produced by the step shown in Chart F except for those compounds wherein $R_{10}$ represents $-Z-Ar_2$ in which (i) Z represents a valence bond and (ii) $Ar_2$ is a halogen-substituted phenyl group.

CHART F

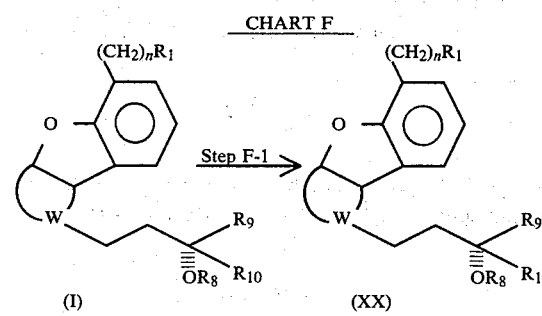

(I)           (XX)

The compounds wherein X is $-CH_2-CH_2-$, $R_1$ is COOH, $R_9$ is hydrogen and $R_{10}$ is $-Z-Ar_2$ in which Z represents a valence bond or $Ar_2$ is a halogen-substituted phenyl group are produced particularly by the steps shown in Chart G. The step shown in Chart G, however, may be generally applied regardless of the nature of $R_{10}$, in the case where $R_{10}$ does not contain any halogen atoms, olefinic double bonds or triple bonds.

CHART G

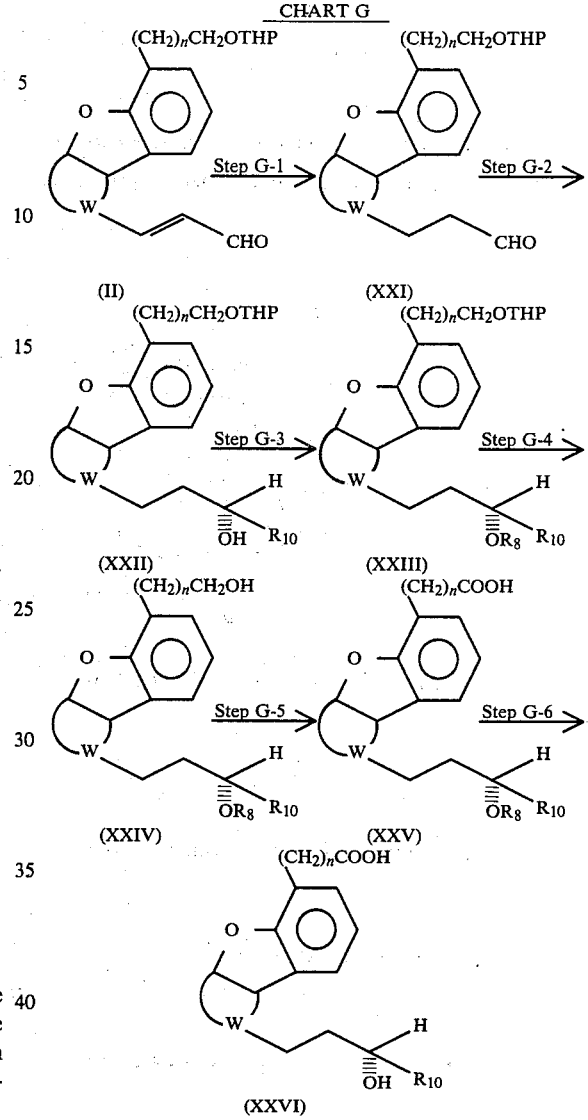

The compounds wherein X is $-CH_2-CH_2-$, $R_1$ is $CH_2OH$, $R_9$ is hydrogen and $R_{10}$ is $-Z-Ar_2$ in which Z represents a valence bond or $Ar_2$ is a halogen-substituted phenyl group are obtained by the step G-4 of Chart G when $R_8$ is other than hydrogen (the compounds XXIV).

The compounds wherein $R_8$ is hydrogen are produced by the step shown in Chart H.

CHART H

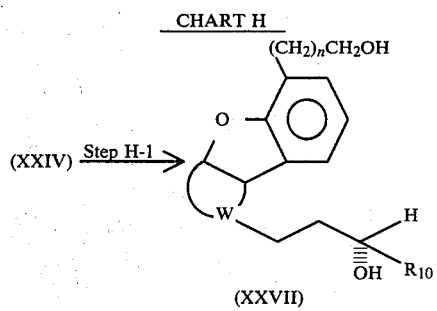

(XXVII)

The compounds wherein X is $-CH_2-CH_2-$, $R_1$ is

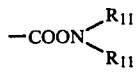

and $R_9$ is hydrogen are produced by the step shown in Chart I except for those in which $R_{11}$ is other than $-SO_2R_{12}$.

CHART I

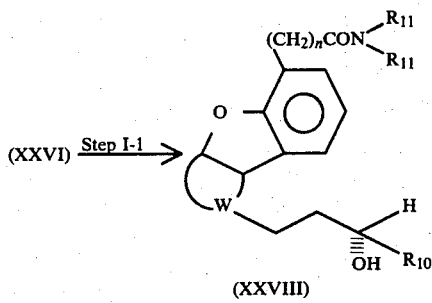

The compounds wherein $R_1$ is $-COOR_2$, X is

$R_9$ is alkyl containing 1-4 carbon atoms and W is

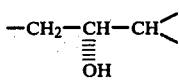

can be produced by the steps shown in Chart J.

CHART J

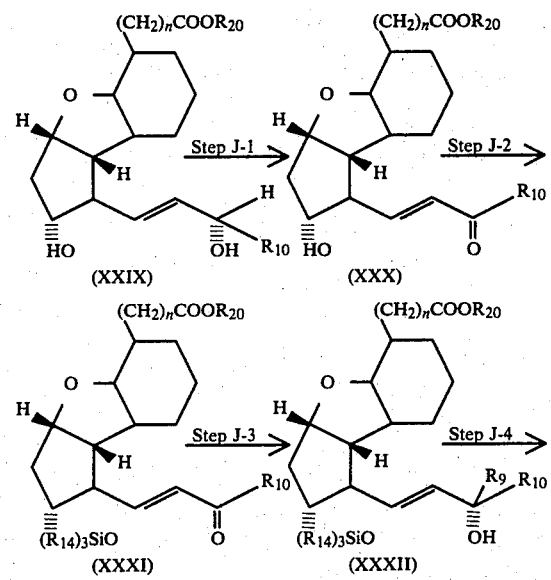

-continued
CHART J

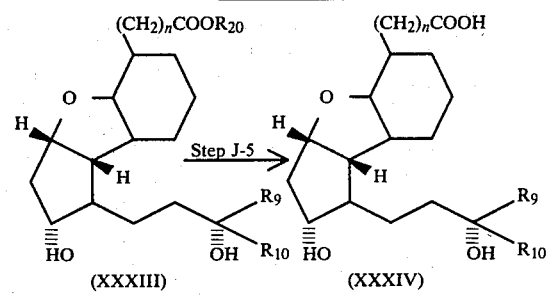

For the compounds wherein $R_1$ is $COOR_2$, X is

$R_9$ is alkyl containing 1-4 carbon atoms and W is

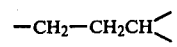

or

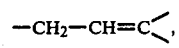

a process analogous to the one shown in Chart J may be employed with the starting compound XXIX in which W is converted to

In the preparation of these compounds the steps J-2 and J-4 are necessarily omitted.

The compounds wherein $R_1$ is $-CH_2OH$, X is

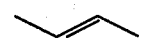

and $R_9$ is alkyl containing 1-4 carbon atoms are produced according the steps shown in Chart K.

CHART K

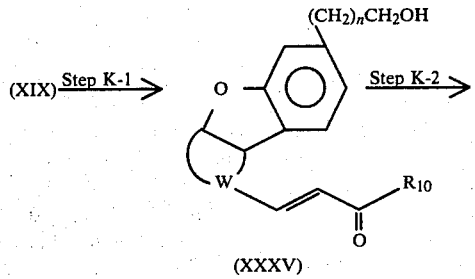

-continued
CHART K

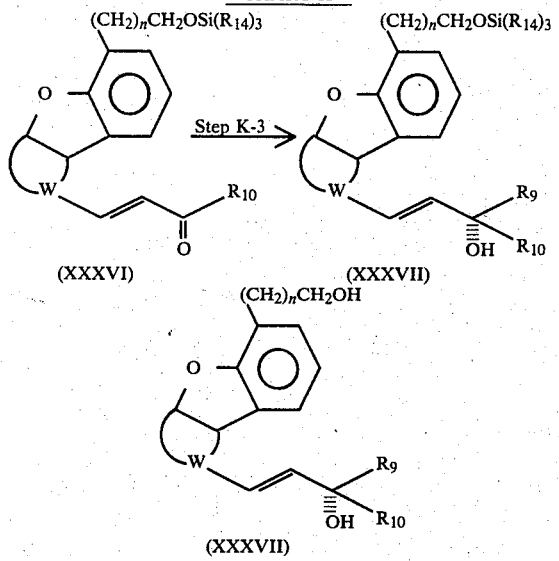

The compounds wherein $R_1$ is

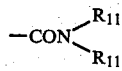

in which one of the $R_{11}$ is $-SO_2R_{12}$ can be produced by the step shown in Chart L.

CHART L

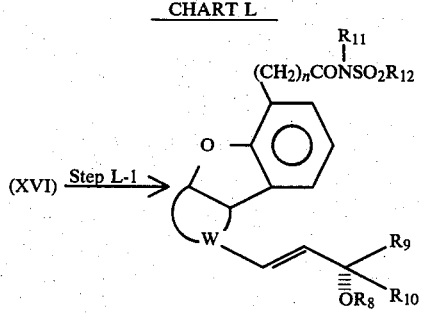

Each step of the processes for the preparation of the compounds according to this invention as outlined above will be described in more details below.

The step A-1 involves alkylation of II with an alkyllithium or an alkylmagnesium halide. As the alkylating agent are mentioned for example, cyclopentyl magnesium bromide, 3-methyl cyclopentyl magnesium bromide, 3-ethyl cyclopentyl magnesium bromide, cyclopentylmethyl magnesium bromide, 3-methyl cyclopentylmethyl magnesium bromide, 3-ethyl cyclopentylmethyl magnesium bromide, 3-n-propyl cyclopentylmethyl magnesium bromide, cyclohexyl magnesium bromide, 2-methyl cyclohexyl magnesium bromide, 2-methyl cyclohexyl magnesium bromide, 3-methyl cyclohexyl magnesium bromide, 4-methyl cyclohexyl magnesium bromide, 4-ethyl cyclohexyl magnesium bromide, cyclohexylmethyl magnesium bromide, 3-methyl cyclohexylmethyl magnesium bromide, 4-methyl cyclohexylmethyl magnesium bromide, cyclopentyl magnesium bromide, cyclooctyl magnesium bromide, cyclododecyl magnesium bromide, phenyl lithium, p-tolyl lithium, m-tolyl lithium, m-chlorophenyl magnesium bromide, p-chlorophenyl magnesium bromide, m-bromophenyl magnesium bromide, p-bromophenyl magnesium bromide, m-fluorophenyl magnesium bromide, p-fluorophenyl magnesium bromide, 3,4-dimethoxyphenyl magnesium bromide, o-methoxyphenyl magnesium bromide, m-methoxyphenyl magnesium bromide, p-biphenyl magnesium bromide, p-phenoxyphenyl magnesium bromide, α-naphthyl magnesium bromide, β-naphthyl magnesium bromide, p-trifluoromethyl phenyl magnesium bromide and the like. However, it is not limited to such compounds.

The alcohol thus obtained which is a mixture of the 15α and 15β isomers is purified to separate the desired 15α isomer (III). The 15β isomer is converted according to the step B-1 by a selective oxidation method of allyl alcohols (for example, by the use as the oxidizing agent manganese dioxide, chloral-carbon tetrachloride or aluminum tri-t-butoxide-acetone) to the 15-keto compound (VIII) or 15-keto compounds with a more general W moiety than in VIII, followed by conversion to a 15α plus 15β mixture by means of a reducing agent such as zinc borohydride, sodium borohydride or $CeCl_3$-sodium borohydride. The 15β isomer thus formed is again subjected to oxidation and reduction steps. Use as the reducing agent of diisobutylaluminum 2,6-di-tert-butyl-4-methylphenoxide [S, Iguchi et al., J. Org. Chem., 44, 1363 (1979)] or binaphthyl aluminum hydride [R. Noyori et al., J. Am. Che. Soc., 101, 3129 (1979)] will result in selective formation of the 15α compound.

The step A-2 is a process for protecting hydroxyl group of the alcohol III by an acyl or aroyl group. The acylation or aroylation is effected with an acid anhydride or halide in the presence of an appropriate base. Illustrative of the agent are acetic, propionic, butyric and benzoic anhydrides, acetyl, propionyl, butyoyl, benzoyl, p-bromo benzoyl, p-phenyl benzoyl, p-nitro benzoyl and p-methoxy benzoyl chlorides and the like. The base includes pyridine, 2-methyl pyridine, 2,6-dimethyl pyridine, 3-methyl pyridine, 4-methyl pyridine, triethylamine, tripropylamine, tri-t-butylamine, N,N-dimethyl benzylamine, N,N-dimethyl phenylamine, 1,5-diazabicyclo[5.4.0]undecene, 1,4-diazabicyclo[4.3.0]nonene, sodium acetate, sodium propionate, sodium butyrate and the like. The reagents, however, are not limited to those mentioned above.

The step A-3 represents catalytic removal of tetrahydropyranyl group with an acid catalyst to liberate hydroxyl group. The catalytic reaction may be carried out after adding an appropriate amount of an acid such as hydrochloric, hydrobromic, sulfuric, acetic, p-toluenesulfonic, or phosphoric acid or p-toluenesulfonic acid pyridinium salt to an appropriate solvent. The acid catalysts, however, are not limited to those mentioned above. The solvent mainly employed is an aqueous solvent such as acetonitrile-water, THF-acetic acid-water, or acetic acid-water, or methanol or ethanol. After completion of the reaction, the acid is neutralized or removed by distillation under reduced pressure, and the crude product is purified by column chromatography.

The step A-4 is a process for oxidizing the alcohol V in which an oxidizing agent conventionally applied for the oxidation of alcohols is employed. Specifically mentioned as the oxidizing agent are chromium trioxide-pyridine, chromium trioxide-acetic acid, bichromatesulfuric acid-dimethylformamide, t-butyl chromate, dimethylsulfoxide-dichlorohexylcarbodiimide, pyridinium dichromatedimethylformamide, pyridinium chloro chromate and the like. The oxidizing agent, however, is not limited to those mentioned above. Preferred solvents are aqueous pyridine for chromium trioxide and dimethylformamide for pyridinium dichromate. Usually, use of pyridinium chromate in dimethylformamide produces good results. The reaction temperature may be in the range from −40° C. to 100° C. and is preferably from 0° to 50° C. to give a preferred reaction rate.

The step A-5 represents removal of the acyl or aroyl group by hydrolysis. Alkalies conventionally used for the hydrolysis of esters such as, for example, sodium hydroxide, potassium hydroxide, sodium methoxide, sodium ethoxide, sodium carbonate and potassium carbonate are preferably employed. After completion of the reaction, the reaction mixture is acidified to a pH from 6 to 1, preferably from 2 to 4.0.

The desired product can be isolated by extraction with an organic solvent from the acid solution.

Preparation of the starting material II used in the step A of the process shown in Chart A is illustrated below in Chart A'.

CHART A'

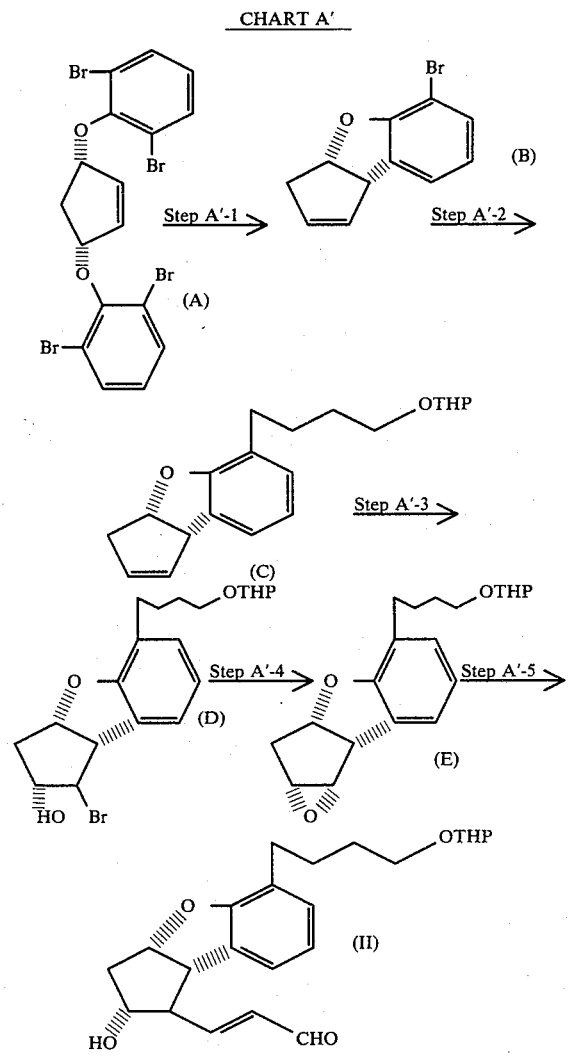

The starting material used in the step A'-1 3,5-bia(2,6-dibromophenoxy)cyclopentene-1 (A) is obtained by an ether synthesis from known compounds 3,5-cis-dibromocyclopentene-1 [W. G. Young et al., J. Am. Chem. Soc., 78, 4338 (1956)] and 2,6-dibromophenol [D. E. Peasons et al., J. Org. Che., 32, 2358 (1967)]. Usually, it is obtained by contacting potassium salt of 2,6-dibromophenol with 3,5-cis-dibromocyclopentene in an inert solvent. The product bis(2,6-dibromo phenoxy) cyclopentene is precipitated in solid form during the reaction due its low solubility. As the inert solvent is employed an ether solvent such as tetrahydrofuran, dimethoxyethane or diethyl ether, a hydrocarbon such as benzene, toluene or xylenes, dimethylformamide, dimethylsulfoxide or the like. In order to increase the reaction rate an interphasic transfer catalyst such as a Crown ether or an quaternary ammonium halide is added thereby ensuring better proceeding of the reaction.

The step A'-1 is a cyclization step of A by treating it with n-butyllithium with stirring at a temperature below 0° C. for a period of 2-3 hours to obtain 3a,8b-dihydro-3H-5-bromocyclopenta[b]benzofuran (B). In place of the n-butyllithium may be used n-propyllithium, n-amyllithium, isopropyllithium, sec-butyllithium, t-butyllithium or the like.

The step A'-2 involves formation of a carbon-carbon bond by the treatment with n-butyllithium at −78° C. followed by addition of 4-iodobutylterahydropyranyl ether. In place of the m-butyllithium may be employed alkyllithiums such as propyllithium, amyllithium, isopropyllithium and t-butyllithium, or aryllithium such as phenyllithium and the like.

Both the steps A'-1 and A'-2 are conducted under argon or nitrogen in an anhydrous ether solvent such as, for example, diethyl ether, tetrahydrofuran, 1,2-dimethoxyethane or the like.

The step A'-3 is a stereo- and geometrospecific addition reaction of a bromohydrin to the double bond. The bromohydrin is formed in N-bromosuccinimide-dimethylsulfoxide-water, which is then reacted with C. The reaction mainly produces the desired compound stereo- and geometrospecifically advantageous for the object. The isomer is purified usually by conventional column chromatography. The purification and separation procedures may be omitted because separation is very easy for the two (syn and anti) epoxides produced in the next step.

The step A'-4 represents the conversion of bromohydrine into the epoxide. The compound D dissolved in an alcohol solvent is subjected to dehydrobromination with an alkali such as potassium carbonate or sodium carbonate to form the syn-epoxide (E).

The step A'-5 involves ring opening and alkylation of the epoxide with 1,3-bis(methylthio)allyl anion and subsequent desulfurization with a mercury or copper chloride. Reaction of E with 1,3-bis(methylthio)allyl anion [E. J. Corey, B. W. Erickson and R. Noyori, J. Am. Che. Soc., 93, 1724 (1971)] at −78° C. gives rise to ring opening of the epoxide and introduction of bis(methylthio)allyl group. A mixture of the geometric isomers as it is desulfurized by addition of a mercury chloride and potassium carbonate followed by heating to 40° C. Thus, there is introduced an αβ-unsaturated aldehyde.

The step B-1 represents selective oxidation of an allyl alcohol which is achieved usually by the use of active manganese dioxide in methylene chloride. The reaction is carried out at a temperature from −40° to 40° C., usually from 0° to 40° C.

The step B-2 involves acylation or aroylation of an alcohol, which is carried out in the same way as in the step A-2.

In the step B-3, the tetrahydropyranyl group is subjected to solvolysis with an acid catalyst to liberate a hydroxyl group. The reaction is carried out in the same way as in the step A-3.

The step B-4 involves oxidation of an alcohol, which is carried out in the same way as in the step A-4.

The step B-5 involves conversion of a carboxylic acid to a corresponding ester to which conventional esterification technique can be applied. Usually, the reaction is effected by reacting a tertiary amine salt or silver salt of the carboxylic acid with an active halide (for example, benzyl bromide or chloride) or reacting a tertiary amine salt of the carboxylic acid with a chlorocarbonate ester to form in situ a mixed acid anhydride, adding a large excess of an alcohol $R_2OH$ and then heating at a temperature from 20° to 100° C.

The step B-6 is a reduction step of the $\alpha,\beta$-unsaturated ketone in which the double bond is simultaneously reduced by the use of $Zn(BH_4)_2$ conventionally employed for the object. This is especially so with the compounds wherein $R_{10}$ is $-Z-Ar_2$ in which Z represents a valence bond and $Ar_2$ is phenyl or substituted phenyl groups. For such compounds, selective reduction of the keto group is applicable by adding sodium borohydride ($NaBH_4$) to a mixture of the $\alpha,\beta$-unsaturated ketone with an equimolar amount of cerium trichloride.

The step B-7 is a methanolysis step which can effectively be conducted by adding to a solution of the compound in dry methanol a catalytic amount of a base such as sodium methoxide, potassium methoxide or anhydrous potassium carbonate. The reaction is carried out at a temperature from −15° to 60° C., usually from 10° to 50° C. with good results.

The step B-8 is a hydrolysis step of the methyl ester, which is carried out in the same way as in the step A-5.

The step C-1 is an esterification step for converting a carboxylic acid to a corresponding carboxylate ester, which can be carried out in the same way as in the step B-5. Unlike the step B-5 the conversion to a corresponding ester of this step may also be effected by the action of a diazoalkane. As the diazoalkane may be mentioned diazomethane, diazoethane, diazopropane, diazodecane and the like. The diazoalkanes, however, are not limited to those mentioned above. As the active halide which is applied to a silver or tertiary amine salt formed from the carboxylic acid may be mentioned benzyl chloride, benzyl bromide, p-bromobenzyl bromide, p-methoxybenzyl bromide, p-phenylbenzyl bromide, p-methylbenzyl bromide, phenacyl bromide, p-bromophenacyl bromide, p-nitrophenacyl bromide, α-benzoylphenacyl bromide and the like. The reaction solvent employed is usually an aprotic polar solvent such as dimethylformamide or acetonitrile. In producing the ester by a mixed acid anhydride method a carboxylic acid of the general formula (XVI) is usually reacted with a tertiary amine to form a quaternary salt, followed by addition of ethyl chlorocarbonate at a low temperature to generate in situ a mixed acid anhydride and subsequent addition of an excess of an alcohol or phenol, and the mixture is warmed. Specific examples of the alcohol or phenol include but are not limited to methanol, ethanol, propanol, butanol, octanol, decanol, isopropanol, 2-ethylhexanol, benzyl alcohol, p-bromobenzyl alcohol, phenetyl alcohol, cyclopentyl alcohol, cyclopentylmethyl alcohol, cyclohexanol, cyclohexylmethyl alcohol, 2-methoxyethanol, 2-(2-methoxyethoxy)ethanol, methyl glycolate, ethyl glycolate, methyl lactate, methyl α-hydroxybutyrate, 2-butyn-1-ol, 2-pentyn-1-ol, 1,3-di(O)-methylglycerin, 1,3-diacetylglycerin, phenol, p-bromo phenol, p-fluoro phenol, m-chloro phenol, m-fluro phenol, 3,4-dichloro phenol, p-(trifluoromethyl) phenol, p-methyl phenol, 3,4-dimethyl phenol, p-methoxy phenol, 4-phenoxy phenol, p-benzoylamino phenol and the like.

The step D-1 represents conversion of a carboxylic acid to a corresponding amide. Usually, a carboxylic acid of the general formula (XVI) is reacted with a tertiary amine to form a quaternary ammonium salt of the carboxylic acid followed by reaction with ethyl chlorocarbonate, p-toluenesulfonyl chloride or the like to form a mixed acid anhydride. Warming with an amine

produces the desired product. The amine is illustrated by but not limited to N-methyl amine, N-ethyl amine, N-butyl amine, N-decyl amine, N,N-dimethyl amine, N,N-diethyl amine, aniline, p-bromo aniline, cyclohexyl amine, cyclopentyl amine, N-benzyl amine, p-bromobenzyl amine, p-chlorobenzyl amine, phenethyl amine and the like.

The step E-1 represents hydrolysis of the protective group to liberate a hydroxyl group, which can be carried out in the same way as in the step A-5.

The step F-1 is a reduction step of a double bond. As the reduction catalyst are used palladium-carbon, palladium-barium sulfate, metallic palladium, Raney nickel and the like. The reduction catalysts, however, are not limited to those mentioned above. The reaction is carried out under a pressure of hydrogen from atmospheric pressure to 300 kg/cm². Usually, a satisfactory reaction rate is obtained under atmospheric pressure. As the solvent are employed alcohols such as ethanol and methanol and esters such as ethyl acetate with good results. Such solvents as benzene, toluene, tetrahydrofuran, dioxane and the like may also be employed.

The step G-1 is a step for reducing the double bond of an α,β-unsaturated aldehyde to give a saturated aldehyde. It is carried out in the same way as in the step F-1, but the hydrogen pressure should be such that the aldehyde will not be reduced. The alcohol produced by partial reduction can easily be separated by column chromatography technique. The step G-2 is a step for alkylating or arylating the compound (XXI) with a lithium or Grignard compound, which is carried out in the same way as in the step A-1. The step G-3 is conducted in the same way as in the step A-2 except that the compound (III) used therein is replaced by the compound (XXII). The step G-4 is conducted in the same way as in the step A-3 except that the compound (IV) used therein is replaced by the compound (XXIII). The step G-5 is conducted in the same way as in the step A-4 except that the compound (V) used therein is replaced by the compound (XXIV). The step G-6 is conducted in the same way as in the step A-5 by replacing the starting compound (VI) used therein by the compound (XXV).

The step H-1 is a step for removing the alcohol-protecting group by alkaline hydrolysis, which is carried out in the same way as in the step A-5 by replacing the compound (VI) used therein by the compound (XXIV).

The step I-1 represents conversion of a carboxylic acid to a corresponding amide, which can be carried out in the same way as in the step D-1 by replacing the starting material (XVI) used therein by the compound (XXVI).

The step J-1 is a step for selectively oxidizing an allyl alcohol to convert to an α,β-unsaturated ketone, which is carried out in the same way as in the step B-1. The step J-2 is a step for trialkylsilylating the hydroxyl group. $R_{14}$ in the general formula (XXXI) represents straight or branched chain alkyl containing 1–10 carbon atoms, which specifically includes but not limited to methyl, ethyl, propyl, butyl, octyl, isopropyl, t-butyl, 2-ethylhexyl and the like. For the silylation of the hydroxyl group the general methods described, for example, in "Protective Groups in Organic Chemistry", ed. by J. F. W. McOmie, pp. 103–104, Plenum Press (London and New York), 1973 and references given therein, can be applicable. Usually, trimethylsilylation or t-butyldimethylsilylation is employed most conveniently. The trimethylsilylation may be effected by treating with trimethylchlorosilane in the presence of a tertiary amine such as pyridine or triethylamine or with a mixture of hexamethyldisilazane and trimethylchlorosilane. For the t-butyldimethylsilylation, it is usually preferable to employ t-butyldimethylsilyl chloride in the presence of imidazole as the base. In general, other trialkylsilylation may also be effected by the reaction of a corresponding trialkylsilyl chloride in the presence of a base such as triethylamine. The step J-3 is accomplished by the reaction with a Grignard reagent such as $R_9MgCl$, $R_9MgBr$ or $R_9Mg\,I$ wherein $R_9$ is as defined above in ether or tetrahydrofuran. The Grignard reagent is used in an amount in the range from 0.8 to 1.5 molar equivalents on the basis of the compound (XXXI). The product (XXXII) is usually used without isolation as the starting material for the step J-4. The step J-4 is a step for removing the hydroxyl-protecting trialkylsilyl group which is usually accomplished by warming a solution dissolved in an aqueous acid solvent. As examples of the aqueous acid solvent are mentioned acetic acid-water, acetic acid-tetrahydrofuran-water, acetic acid-ethanol water, ethanol-0.91 N hydrochloric acid and the like. The reaction is usually effected by allowing to stand in 10:1 ethanol/water mixture with a drop of acetic acid added at a temperature from 0° to 50° C. for a period from 0.5 to 5 hours. Alternatively, the compound (XXXII) may be reacted with a tetraalkylammonium fluoride. Usually, use of tetrabutylammonium fluoride produces satisfactory results.

The step K-1 is carried out in the same way as in the step J-1 by replacing the compound (XXIX) used therein by the compound (XIX). The step K-2 can be conducted in the same way as in the step J-2. The step K-3 can be conducted in the same way as in the step J-3 by replacing the compound (XXXI) used therein by the compound (XXXVI). The step K-4 can be conducted in the same way as in the step J-4.

The step L-1 is accomplished by converting the compound (XVI) to a mixed acid anhydride followed by reaction with a lithium sulfonamide reagent

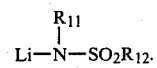

Conversion of the compound (XVI) to the mixed acid anhydride can be done by the use of the same method as described for the step D-1.

The steps shown in Charts A-L are carried out in the same manner with any of the d, l and dl compounds. For the production of the d or l isomers, the steps according to Charts A-L may be carried out using a corresponding optically active compound as the starting material. The optically active starting material may be obtained first by preparing an optically active compound according to the procedures as described below in Reference Examples 1–3 and then by preparing 3a,8b-cis-dihydro-3H-5-(4-tetrahydropyranyloxybutyl)-1,2-syn-epoxy-cyclopenta[b]-benzofuran according to the procedures as described in Reference Examples 4–10 which is in turn converted by the step A'-5 shown in Chart A' to the starting material (II).

The compounds of the general formula (I) obtained according to the present invention have potent platelet-aggregation inhibiting and hypotensive activities. The compounds are also highly active in protecting the gastric mucosa cells as well as in inhibiting gastric secretion.

More particularly, the compounds 1, 11 and 96 of the invention show platelet aggregation-inhibiting activities approximately as potent as those of prostaglandin $E_1$. Human or rabbit (anesthesized) blood was treated with a 1/10 volume of 3.8% aqueous solution of sodium citrate to prevent coagulation. The blood was centrifuged at 200×g for 10 minutes to separate platelet-rich plasma. The plasma was subjected to aggregation by the treatment with arachidonic acid, adenosine diphosphate (ADP) and collagen according to Born's method (Nature, 1962, 194, 927). Inhibition of the aggregation was determined by the measurement by an aggrometer following pre-treatment with a compound of the invention.

The compounds 1, 11 and 96 of the invention have hypotensive activities approximately equivalent to the activity of prostaglandin $E_1$ at a dose of the former twice as much. The activities of the former are more durable. The drug in solution was infused intravenously into pentobarbital-anesthesized rats via the catheter kept therein followed by measurement of carotid aortic pressure.

As for the gastric mucosa-protecting action, injury on the gastric mucosa in rats caused by ethanol according to the method of Robert et al. (Gastroenterology, 1979, 77, 433) was greatly inhibited by oral administration of the compounds 1, 11 and 96 of the invention at doses of 10–30 mg/kg bodyweight, as low as 0.3–1 times the dose of prostaglandin $E_2$.

The gastric juice secretion-inhibitory action was tested according Shay's method (Gastroenterology 1954, 26, 906). Subcutaneous injection of the compounds 1, 11 and 96 of the invention strongly reduced the amount of gastric juice at doses of 0.3–1 mg/kg bodyweight, as low as 0.1–0.3 times the dose of prostaglandin $E_2$.

The compounds of the invention did not cause diarrhea in rats at a higher subcutaneous dose of 3 mg/kg bodyweight unlike prostaglandins $E_1$ and $E_2$.

50%-lethal doses of these compounds in mice by intraperitoneal or intravenous administration are 100–200 mg/kg bodyweight, thus indicating a large difference from the pharmacologically active dose.

One of the pharmaceutical applications of the compounds of this invention expected is as an anti-ulceric drug. For the purpose of treating gastric ulcer, for example, the compound is administered orally, subcutaneously, intramuscularly or intrarectally at doses of 0.01–100 mg per person once to three times a day.

Moreover, application as, an anti-thrombosic or hypotensive agent is expected. For example, the compound is given, for example, intravenously at doses of 0.001–100 mg/g/min for the purpose of treating Berger's disease, orally at doses of 0.01–50 mg per person once to three times a day when used as an anti-thrombosic agent, or orally at doses of 0.01–50 mg per person once to three times a day when used as a hypotensive agent.

The compounds of the invention may orally be administered in solid form containing excipients such as starch, lactose, sucrose, a certain clay and flavor-covering agent. They may also be given parentherally in the form of a sterile solution which may contain sodium chloride, glucose or the like in an amount sufficient to make it isotonic.

The compounds of the invention which are stable inherently by their chemical structures are encountered with no difficulties in preparing pharmaceutical formulations and find wide uses by a variety of routes of administration such as oral preparations, injections and suppositories.

The invention will be described in more details by way of examples of the process for preparing the compounds of the inventions. In the examples, the following abbreviations are used:

TLC: Thin layer chromatography (silica gel thin layer plate Art 5715 manufactured by Merck was used unless otherwise indicated)
I R: Infrared absorption spectrum
NMR: Nulcear magnetic resonance
MS or Mass: Mass spectrum
(Measurements were done by a Hitachi Spectrophotometer Type 215 for IR, by a Varian-XL-100 for NMR and by a Hitachi RMU-7M for MS.

Unless otherwise indicated, drying was performed over anhydrous magnesium sulfate, and concentration by a rotary evaporator.

REFERENCE EXAMPLE 1

Preparation of 3a,8b-cis-dihydro-3H-5-carbomethoxy-cyclopenta[b]benzofuran

To a stirred solution of 3 g of 3a,8b-cis-dihydro-3H-5-bromo-cyclopenta[b]benzofuran in 60 ml of dry THF at $-78°$ C. was added dropwise under argon 10.2 ml of n-butyllithium (1.5 N). Stirring was continued at $-78°$ C. for 35 minutes. The temperature was gradually increased to $-10°$ C. while introducing carbon dioxide generated from dry ice. Stirring was continued at $-10°$ C. for additional one hour. To the reaction mixture was added solid ammonium chloride followed by stirring at room temperature for 5 minutes. Then, the THF was removed under reduced pressure, and to the residue was added benzene. The benzene solution was washed once with saturated aqueous solution of sodium hydrogen carbonate and twice with water. The combined aqueous layers were acified with 2N hydrochloric acid to pH 2 and extracted three times with ethyl acetate. The combined ethyl acetate layers were washed with water and saturated aqueous sodium chloride, dried and concentrated to give 2.1 g of 3a,8b-cis-3H-5-carboxy-cyclopenta[b]benzofuran.

A suspension of the benzofuran in ethyl acetate was treated with ethereal diazomethane. Concentration yielded 2.2 g of crude oily product. The oil was purified by column chromatography [silica gel; ethyl acetate:cyclohexane (1:3)] to give 1.9 g of 3a,8b-cis-dihydro-3H-5-carbomethoxy-cyclopenta[b]benzofuran (yield 75%).

IR (liquid film) $\nu cm^{-1}$: 1720, 1605.

MNR $\delta(CDCl_3)$: 2.90 (2H, m), 3.89 (3H, s) 4.18 (1H, dd, J=8.0 Hz, 0.3 Hz) 5.60 (1H, dt, J=8.0 Hz, 4,0 Hz) 5.75 (2H, m), 6.84 (1H, t, J=8.0 Hz) 7.24 (1H, dd, J=8.0 Hz, 1.2 Hz) 7.70 (1H, dd, J=8.0 Hz, 1.2 Hz).

Mass (m/e): 216 (M+).

REFERENCE EXAMPLE 2

Preparation of 3a,8b-cis-dihydro-3H-5-carboxymenthyloxy-cyclopenta[b]benzofuran

To a suspension of 300 mg of 3a,8b-cis-dihydro-3H-5-carboxycyclopenta[b]benzofuran in 5 ml of dry benzene was 0.8 ml of oxyalyl chloride. The mixture was stirred at 60° C. for 1 hour. The reaction mixture was concentrated to dryness and flushed with argon. The residue was dissolved in 5 ml of pyridine, to the solution was added 600 mg of l-menthol and the solution was stirred at 60° C. for 1.5 hours the mixture was evaporated to dryness. To the residue was added ethyl acetate and the resulting mixture was washed with saturated aqueous solution of sodium hydrogen carbonate, water and saturated aqueous sodium chloride and concentrated. The oily material thus obtained was purified by column chromatography [silica gel; ethyl acetate:cyclohexane (1:9)] to give 470 mg of 3a,8b-cis-dihydro-3H-5-carbomenthyloxy-cyclopenta[b]benzofuran (yield 90%).

IR $\nu cm^{-1}$: 1705, 1605, 1260, 1285, 1140 1060, 1040, 1015.

REFERENCE EXAMPLE 3

Resolution of 3a,8b-cis-dihydro-3H-5-carbomenthyloxy-cyclopenta[b]benzofuran

Three hundred milligrams of the 3a,8b-cis-dihydro-3H-5-carbomenthyloxy-cyclopenta[b]benzofuran was separated by column chromatography [silica gel; ethyl acetate:cyclohexane (0.5:9.5)] into 73.7 mg of a less polar portion and 86.3 mg of a polar portion. Analytical data of the less polar portion:

IR $\nu cm^{-1}$: 1705, 1605, 1260, 1285, 1140 1060, 1040, 1015.

NMR $\delta(CDCl_3)$: 0.78 (3H, d, J=8.0 Hz) 0.90 (6H, d, J=7.0 Hz) 2.90 (1H, m), 4.40 (1H, d, J=8.0 Hz) 4.92 (1H, dt, J=11.0 Hz, 4.0 Hz) 4.70 (3H, m) 6.84 (1H, t, J=8.0 Hz) 7.34 (1H, dd, J=8.0 Hz, 1.2 Hz) 7.74 (1H, dd, J=8.0 Hz, 1.2 Hz).

Mass (m/e): 340 (M+).

$[=]_D^{MeOH} = -116$.

Analytical data of the polar portion:

IR $\nu cm^{-1}$: 1705, 1603, 1260, 1285, 1138, 1058, 1040, 1015.

NMR $\delta(CDCl_3)$: 0.80 (3H, d, J=6.5 Hz) 0.94 (6H, d, J=7.0 Hz) 2.92 (1H, m) 4.38 (1H, d, J=8.0 Hz) 4.90 (1H, dt, J=10.0 Hz, 4,0 Hz) 5.70 (3H, m) 6.84 (1H, t, J=8.0 Hz) 7.34 (1H, dd, J=8.0 Hz, 1.2 Hz) 7.70 (1H, dd, J=8.0 Hz, 1.2 Hz).
  Mass (m/e): 340 (M+).
  $[\alpha]_D^{MeOH} = +11.5$.

REFERENCE EXAMPLE 4

Preparation of
3a,8b-cis-dihydro-3H-5-carboxy-cyclopenta[b]benzofuran (optically active isomer)

To a solution of 63 mg of the compound with $[\alpha]_D^{MeOH} = -116$ which had been obtained in Reference Example 3 dissolved in 2 ml of methanol was added 1 ml of 3 N sodium hydroxide. The mixture was stirred at 60° C. for 14 hours. The reaction mixture was concentrated, and to the residue was added ether:benzene (2:1), followed by three extractions with water. The combined aqueous layers were acidified with 6 N hydrochloric acid to pH 2 and extracted three times with ethyl acetate. The combined ethyl acetate layers were washed with water, saturated aqueous sodium chloride, dried and concentrated to obtain 34.6 mg of an optically active carboxylic acid. m.p. 147°-148° C.
  IR $\nu cm^{-1}$ (KBr): 3600-2400, 1690, 1605.
  Mass (m/e): 202 (M+).
  $[\alpha]_D^{MeOH} = -104$.

From 76 mg of the compound with $[\alpha]_D^{MeOH} = +11.5$ under similar conditions there was obtained 42 mg of an optically active carboxylic acid. m.p. 148°-150° C.
  IR $\nu cm^{-1}$ (KBr): 3600-2400, 1690, 1605.
  Mass (m/e): 202 (M+).
  $[\alpha]_D^{MeOH} = +105$.

REFERENCE EXAMPLE 5

Preparation of
3a,8b-cis-dihydro-3H-5-dihydroxymethyl-cyclopenta[b]benzofuran

To a solution of 300 mg of 3a,8b-cis-dihydro-3H-5-carbomethoxy-cyclopenta[b]benzofuran in 7 ml of dry toluene at −78° C. was added 0.298 ml of diisobutylaluminum hydride. The mixture was stirred at −78° C. for 3 hours. To the reaction mixture was added methanol, and the resulting mixture was stirred at room temperature for 5 minutes, followed by addition of 50% aqueous sodium chloride and three extractions with ether. The combined ether extracts were washed with saturated aqueous sodium chloride, dried over magnesium sulfate and concentrated to give 300 mg of an oily material. The oil was purified by column chromatography [silica gel; ethyl acetate:cyclohexane (1:4)] to give 230 mg of the title compound (yield 88%).
  IR (liquid film)$\nu cm^{-1}$: 3245, 1598, 1000.

REFERENCE EXAMPLE 6

Preparation of
3a,8b-cis-dihydro-3H-5-formyl-cyclopenta[b]benzofuran

To a solution of 230 mg of 3a,8b-cis-dihydro-3H-5-hydroxymethyl-cyclopenta[b]benzofuran in 5 ml of methylene chloride was added 5 g of active manganese dioxide. The mixture was stirred under argon at room temperature for 2 hours. The reaction mixture was filtered through a short silica gel column to separate the manganese dioxide, thoroughly washed with methylene chloride and concentrated to obtain 210 mg of the aldehyde product in almost pure state (yield 91%). m.p. 59°-60° C.
  IR (liquid film)$\nu cm^{-1}$: 2730, 1680, 1605.
  NMRδ(CDCl$_3$): 2.90 (2H, m), 4.40 (1H, d, J=7.0 Hz) 5.70 (3H, m), 6.90 (1H, t, J=8.0 Hz) 7.41 (1H, dd, J=8.0 Hz, 1.2 Hz) 7.58 (1H, dd, J=8.0 Hz, 1.2 Hz) 10.10 (1H, s).
  Mass (m/e) 186 (M+)

REFERENCE EXAMPLE 7

Preparation of
3a,8b-cis-dihydro-3H-5-formyl-1,2-syn-epoxy-cyclopenta[b]benzofuran To an ice-cooled solution of 100 mg of 3a,8b-cis-dihydro-3H-5-formyl-cyclopenta[b]benzofuran in 2.8 ml of dimethylsulfoxide:water (18:1) was added 180 mg of N-bromosuccinimide. The mixture was stirred for 4 hours. To the reaction mixture were added 300 mg of potassium carbonate and 0.5 ml of water, and the mixture was stirred with cooling with ice for 2 hours. To the reaction mixture was added water, and the mixture was extracted five times with ether. The combined ether layers were washed with water, dried and concentrated to give 130 mg of an oily material. The oil was purified by column chromatography [silica gel; ethyl acetate:cyclohexane (1:1)] to obtain 105 mg of crude crystals. Recrystallization from benzene-hexane yielded 90 mg of the pure compound, m.p. 100°-101° C.
  IR$\nu cm^{-1}$ (KBr): 2790, 1680, 1605, 845.
  NMRδ(CDCl$_3$): 2.30 (1H, dd, J=16.0 Hz, 7.0 Hz) 2.68 (1H, d, J=16.0 Hz) 3.82 (1H, d, J=8.0 Hz) 6.96 (1H, t, J=8.0 Hz) 7.50 (1H, dd, J=8.0 Hz, 1.2 Hz) 7.64 (1H, dd, J=8.0 Hz, 1.2 Hz) 10.18 (1H, s).
  Mass (m/e): 202 (M+).

REFERENCE EXAMPLE 8

Preparation of
3a,8b-cis-dihydro-3H-5-(4-tetrahydropyranyloxy-1-hydroxy-n-butyl)-1,2-syn-epoxy-cyclopenta[b]benzofuran To a stirred solution of 10 mg of 3a,8b-cis-dihydro-3H-5-formyl-1,2-syn-epoxy-cyclopenta[b]benzofuran dissolved in dry THF at −60° C. was added a large excess of a THF solution of Grignard reagent prepared from 3-bromo-n-propyl-tetrahydropyranyl ether. The mixture was stirred at −30°-−40° C. for 1.5 hours. To the reaction mixture was added solid ammonium chloride, followed by stirring at −40° C. for 20 minutes. The resulting mixture was extracted three times with ether, washed with saturated aqueous sodium chloride, dried and concentrated. The oily material thus obtained was purified by column chromatography [silica gel; ethyl acetate:cyclohexane (1:1)] to give 13 mg of the pure product.
  IR (liquid film)$\nu cm^{-1}$: 3430, 1595, 1025, 845.

REFERENCE EXAMPLE 9

Preparation of
3a,8b-cis-diyydro-3H-5-(4-tetrahydropyranyloxy-1-acetoxy-n-butyl)-1,2-syn-epoxy-cyclopenta[b]benzofuran A solution of 13 mg of 3a,8b-cis-3H-5-(4-tetrahydropyranyloxy-1-hydroxy-n-butyl)-1,2-syn-epoxy-cyclopenta[b]benzofuran in 1 ml of acetic anhydride and 0.5 ml of dry pyridine was stirred at room temperature for 14 hours. The reaction solution was concentrated to dryness, and the residue was dissolved in toluene. The azeotropic separation was twice repeated. The oily material thus obtained was purified by column chromatography [silica gel; ethyl acetate:cyclohexane (1:1)] to give 13 mg of the pure product.

IR (liquid film)$\nu$cm$^{-1}$: 1738, 1595, 1230, 1030, 845.

NMR $\delta$(CDCl$_3$): 2.05 (3H, s), 3.68 (2H, s) 3.20–3.90 (5H, m), 4.58 (1H, m) 5.37 (1H, t, J=7.2 Hz) 5.93 (1H, t, J=7.0 Hz) 6.86 (1H, t, J=8.0 Hz) 7.20 (2H, m).

Mass (m/e): 388 (M+).

REFERENCE EXAMPLE 10

Preparation of 3a,8b-cis-dihydro-3H-5-(4-tetrahydropyranyloxy-n-butyl-1,2-syn-epoxy-cyclopenta[b]benzofuran To a solution of 6 mg of 3a,8b-cis-dihydro-3H-5-(4-tetrahydropyranyloxy-1-acetoxy-n-butyl)-1,2-syn-epoxy-cyclopenta[b]benzofuran in 0.5 ml of ethyl acetate was added 15 mg of 10% palladium-carbon. The mixture was stirred under hydrogen at room temperature for 3 hours. The catalyst was filtered and the filtrate was concentrated to give 6 mg of an oily material. The oily material thus obtained was purified by column chromatography (silica gel; ethyl acetate:cyclohexane (1:2)] to give 3 mg of the pure product.

EXAMPLE 1

5,6,7-trinor-4,8-inter-mphenylene-16,17,18,19,20-pentanor-15-phenyl PGI$_2$ (1)

To a solution of 570 mg (1.47 mmol) of 3a,8b-cis-2,3,3a,8-tetrahydro-1H-5-(4-tetrahydropyranyl-oxybutyl)-1$\beta$-(2-formylethenyl)-2$\alpha$-hydroxycyclopenta[b]benzofuran in 15 ml of THF $-78°$ C. was slowly added 5 ml of 1.5 N ether solution of phenyllithium. After completion of the addition, 1 ml of methanol was added, then 4 ml of saturated aqueous ammonium chloride and 3 ml of saturated sodium chloride were added, followed by extraction with 50 ml of ether. The extract was washed with saturated aqueous sodium chloride, dried, concentrated and purified by column chromatography (Merck's Rober B, ethyl acetate:cyclohexane=6:1) to give 314 mg (46%) of the diol 15$\alpha$ isomer and 183 mg (27%) of the diol 15$\beta$ isomer. The diol 15$\alpha$ isomer was dissolved in 5 ml of pyridine and 6.7 ml of acetic anhydride, and the solution was stirred at room temperature for 3 hours. The solvent was distilled off from the resulting solution under reduced pressure, and the residue was dissolved in 50 ml of ether. The ether solution was washed with 3 ml of saturated aqueous sodium bicarbonate and 5 ml of aqueous copper sulfate, dried and concentrated to give 403.5 mg of crude diacetate product. The crude product was dissolved in 12 ml of acetonitrile, 6 ml of THF, 8 ml of 1/10 N hydrochloric acid and 4 ml of 1/4 N hydrochloric acid. The solution was stirred at room temperature for 4 hours and then allowed to stand overnight at $-15°$ C. To the resulting solution were added 0.1 ml of triethylamine, 3 ml of saturated aqueous sodium bicarbonate and 2 ml of saturated aqueous sodium chloride. The mixture was extracted with 100 ml of ether, and the extract was dried, concentrated and purified by column chromatography (Merck's Rober Column A, cyclohexane:ethyl acetate=1:1) to give 138 mg (43%) of the corresponding alcohol.

The alcohol was dissolved in 3 ml of dimethylformamide. To the solution was added 752 mg of pyridinium dichromate, and the mixture was stirred overnight. To the resulting mixture was added 6 ml of water, followed by extraction with 150 ml of ether. The ether extract was washed with 5 ml of saturated aqueous sodium chloride, dried and concentrated to give 132 mg (93%) of the carboxylic acid diacetate. The carboxylic diacetate was dissolved in 5 ml of methanol, followed by addition of 2 ml of 1 N aqueous sodium hydroxide. The mixture was stirred overnight, and the methanol was distilled off, followed by washing with 1 ml of cyclohexane:ether (1:1). The aqueous solution was acidified with 1 N hydrochloric acid at 0° C. to pH 2-3, extracted with 20 ml of ethyl acetate, evaporated and concentrated to afford 105 mg of 5,6,7-trinor-4,8-inter-m-phenylene-16,17,18,19,20-pentanor-15-phenyl PGI$_2$. The structure was confirmed by the following spectral data:

IR (Neat) $\nu$cm$^{-1}$: 3600–2500, 2920, 1705, 1595, 1445, 1250, 1190, 1065, 1025, 965, 860, 760, 740, 698.

NMR (CDCl$_3$) $\delta$ppm: 1.8–2.1 (m, 4H9 2.4 (5, 2H) 2.60 (t, 3H) 3.42 (t, 1H) 3.92 (q, 1H) 4.9–5.5 (b, 5H) 5.75 (m, 2H, C$_{13}$HC$_{14}$H) 6.6–7.0 (m, 3H) 7.33 (bs, 5H, C$_6$H$_5$).

Mass (m/e): 394.

EXAMPLE 2-10

The procedures of Example 1 were followed except the uses of m-trifluoro methyl phenyl lithium, p-chloro phenyl lithium, m-bromo phenyl lithium, p-bromo phenyl lithium, m-fluoro phenyl lithium, p-fluoro phenyl lithium, p-biphenyl lithium, $\alpha$-naphthyl lithium and $\beta$-naphthyl lithium in place of the phenyl lithium used therein give:

5,6,7-trinor-4,8-inter-m-phenylene-16,17,18,19,20-pentanor-15-(m-trifluoro methyl phenyl) PGI$_2$(2), 5,6,7-trinor-4,8-inter-m-phenylene-16,17,18,19,20-pentanor-15-(p-chloro phenyl) PGI$_2$ (3), 5,6,7-trinor-4,8-inter-m-phenylene-16,17,18,19,20-pentanor-15-(m-bromo phenyl) PGI$_2$ (4), 5,6,7-trinor-4,8-inter-m-phenylene-16,17,18,19,20-pentanor-15-(p-bromo phenyl) PGI$_2$ (5), 5,6,7-trinor-4,8-inter-m-phenylene-16,17,18,19,20-pentanor-15-(m-fluoro phenyl) PGI$_2$ (6), 5,6,7-trinor-4,8-inter-m-phenylene-16,17,18,19,20-pentanor-15-(p-fluoro phenyl) PGI$_2$ (7), 5,6,7-trinor-4,8-inter-m-phenylene-16,17,18,19,20-pentanor-15-(p-biphenyl) PGI$_2$ (8), 5,6,7-trinor-4,8-inter-m-phenylene-16,17,18,19,20-pentanor-15-($\alpha$-naphthyl) PGI$_2$ (9), and 5,6,7-trinor-4,8-inter-m-phenylene-16,17,18,19,20-pentanor-15-($\beta$-naphthyl) PGI$_2$ (10), respectively.

See Table 1.

TABLE 1

| Compound No. | IR ($\nu$cm$^{-1}$) | Mass (m/e) |
|---|---|---|
| (2) | 3500–2500, 2920, 2850 1700, 970, 740 | 462 |
| (3) | 3500–2500, 2920, 2850 965, 740, 1700 | 428, 430 |
| (4) | 3500–2500, 2920, 2850 1700, 970, 740 | 472, 474 |
| (5) | 3500–2500, 2920, 2850 1700, 965, 740 | 472, 474 |
| (6) | 3500–2500, 2920, 2850 1700, 965, 740 | 412 |
| (7) | 3500–2500, 2920, 2850 1700, 965, 740 | 412 |
| (8) | 3500–2500, 2920, 2850 1700, 970, 760, 740 697 | 470 |
| (9) | 3500–2500, 2920, 2850 1700, 970, 740 | 444 |
| (10) | 3500–2500, 2920, 2850 | 444 |

TABLE 1-continued

| Compound No. | IR (νcm$^{-1}$) | Mass (m/e) |
|---|---|---|
| | 1700, 970, 740 | |

EXAMPLE 11

5,6,7-trinor-4,8-inter-m-phenylene-16,17,18,19,20-pentanro-15-cyclohexyl PGI$_2$ (11)

To a solution 3 g. (7.7 mmol) of 3a,8b -cis-2,3,3a,8b-tetrahydro-1H-5-(4-tetrahydropyranyloxybutyl)-1β-(2-formylethenyl)-2α-hydroxycyclopenta[b]benzofuran in 40 ml of THF at −78° C. was added ca. 20 ml of 1 N THF solution of cyclohexylmagnesium bromide. To the mixture were added 2 ml of methanol and then 2 ml of saturated aqueous sodium chloride, followed by extraction with 200 ml of ether. The ether extract was washed with 5 ml of saturated aqueous sodium chloride, dried, concentrated and purified by column chromatography (Rober C, cyclohexane:ethyl acetate=1:7) to obtain 1.3 g (35.6%) of the diol 15α isomer and 1.6 g (43.7%) of the diol 15β iomer. The diol 15α isomer was dissolved in 20 ml of pyridine and 27 ml of acetic anhydride. The solution was stirred at room temperature for 3 hours, and the solvent was distilled off under reduced pressure, followed by extraction with ether. The ether extract was washed with 10 ml of saturated aqueous sodium bicarbonate and 10 ml of aqueous copper sulfate, dried and concentrated to give 1.35 g (90%) of the crude diacetate product. The diacetate was dissolved in 25 ml of acetonitrile, 12 ml of THF, 10 ml of 1/10 N hydrochloric acid and 2 ml of ¼ N hydrochloric acid. The solution was stirred at room temperature for 4 hours, and then allowed to stand overnight at −15° C. To the resulting mixture were added 0.6 ml of triethylamine, 3 ml of saturated aqueous sodium bicarbonate and 2 ml of saturated aqueous sodium chloride, followed by extraction with 100 ml of ether. The extract was dried, concentrated and purified by column chromatography (Merck's Rober Column B, cyclohexane:ethyl acetate=1:1) to obtain 800 mg (71%) of the alcohol product. The alcohol was dissolved in 18 ml of dimethylformamide, and to the solution was added 4.47 g of pyridinium dichromate. The mixture was stirred overnight, to which was then added 54 ml of water, followed by extraction with 500 ml of ether. The extract was washed with 15 ml of saturated aqueous sodium chloride to give 800 mg of the carboxylic acid diacetate. The carboxylic acid diacetate was dissolved in 25 ml of methanol, and to the solution was added 8 ml of 1 N aqueous solution of sodium hydroxide. The mixture was stirred overnight, and after the methanol was distilled off, washed with 1 ml of cyclohexane:ether (1:1). The aqueous solution was acidified with 9 ml of 1 N hydrochloric acid at 0° C. to pH 2-3, followed by extraction with 60 ml of ethyl acetate. The ether extract was dried and concentrated to give 420 mg of the desired product 5,6,7-trinor-4,8-inter-m-phenylene-16,17,18,19,20-pentanor-15-cyclohexyl PGI$_2$.

The structure was confirmed by the following spectral data:

IR (Neat) νcm$^{-1}$: 3600-2500, 2920, 2850, 1702, 1590, 1445, 1255, 1185, 1065, 1020, 965, 890, 860, 740.

NMR (CDCl$_3$) δ ppm: 0.9-1.5 (m, 8H) 1.6-2.1 (m, 8H) 2.35 (t, 2H) 2.63 (t, 2H) 3.40 (t, 1H) 3.85 (b, 2H) 5.1 (m, 1) 5.6 (m, 5H) 6.7-7.1 (m, 3H)

EXAMPLES 12-21

The procedures of Example 2 were followed except the uses of cyclo pentyl magnesium bromide, 2-methyl cyclo pentyl magnesium bromide, 3-methyl cyclo pentyl magnesium bromide, 3-ethyl cyclo pentyl magnesium bromide, cyclo heptyl magnesium bromide, cyclo octyl magnesium bromide, cyclo decyl magnesium bromide, 2-methyl cyclo hexyl magnesium bromide, 3-methyl cyclo hexyl magnesium bromide and 4-methyl cyclo hexyl magnesium bromide in place of the cyclo magnesium bromide used therein to give:

5,6,7-trinor-4,8-inter-m-phenylene-16,17,18,19,20-pentanor-15-cyclopentyl PGI$_2$ (12), 5,6,7-trinor-4,8-inter-m-phenylene-16,17,18,19,20-pentanor-15-(2-methyl cyclo pentyl) PGI$_2$ (13), 5,6,7-trinor-4,8-inter-m-phenylene-16,17,18,19,20-pentanor-15-(3-methyl cyclo pentyl) PGI$_2$ (14), 5,6,7-trinor-4,8-inter-m-phenylene-16,17,18,19,20-pentanor-15-(3-ethyl cyclo pentyl) PGI$_2$ (15), 5,6,7-trinor-4,8-inter-m-phenylene-16,17,18,19,20-pentanor-15-cycloheptyl PGI$_2$ (16), 5,6,7-trinor-4,8-inter-m-phenylene-16,17,18,19,20-pentanor-15-cyclooctyl PGI$_2$ (17), 5,6,7-trinor-4,8-inter-m-phenylene-16,17,18,19,20-pentanor-15-cyclododecyl PGI$_2$ (18), 5,6,7-trinor-4,8-inter-m-phenylene-16,17,18,19,20-pentanor-15-(2-methyl cyclo hexyl) PGI$_2$ (19), 5,6,7-trinor-4,8-inter-m-phenylene-16,17,18,19,20-pentanor-15-(3-methyl cyclo hexyl) PGI$_2$ (20), and 5,6,7-trinor-4,8-inter-m-phenylene-16,17,18,19,20-pentanor15-(4-methyl cyclo hexyl)PGI$_2$ (21), respectively, See Table 2.

TABLE 2

| Compound No. | IR (νcm$^{-1}$) | Mass (m/e) |
|---|---|---|
| (12) | 3500-2500, 2920, 2850 1700, 965, 740 | 386 |
| (13) | 3500-2500, 2920, 2850 1700, 1440, 965, 740 | 400 |
| (14) | 3500-2500, 2920, 2850 1700, 1445, 965, 740 | 400 |
| (15) | 3500-2500, 2920, 2850 1700, 1440, 965, 740 | 414 |
| (16) | 3500-2500, 2920, 2850 1700, 1440, 970, 742 | 414 |
| (17) | 3500-2500, 2920, 2850 1700, 970, 740 | 428 |
| (18) | 3500-2500, 2920, 2850 1700, 970, 740 | 484 |
| (19) | 3500-2500, 2920, 2850 1700, 1440, 970, 740 | 414 |
| (20) | 3500-2500, 2920, 2850 1700, 1440, 970, 740 | 414 |
| (21) | 3500-2500, 2920, 2850 1702, 1445, 970, 738 | 414 |

EXAMPLE 22

To a solution of 506 mg (1.03 mmol) of 3a,8b-cis-2,3,3a,8b-tetrahydro-1H-5-(4-tetrahydropyranyloxybutyl)-1/β-(2-formylethenyl)2α-hydroxycyclopenta[b-]benzofuran in 50 ml of THF at 78° C. was added 15 ml of 0.24 N THF solution of cyclohexylmethyllithium. After completion of the addition, 1 ml of methanol, 4 ml. of saturated aqueous ammonium chloride and 3 ml of saturated aqueous sodium chloride were added. The mixture was extracted with 100 ml of ether, and the extract was washed with saturated aqueous sodium chloride, dried, concentrated and purified by column chromatography (Merck's Rober Column C, cyclohexane: ethyl acetate=1:5) to give 329 mg (52.3%) of the diol 15α isomer and 176 mg (28%) of the diol 15β isomer.

The diol 15α isomer was dissolved in 5 ml of pyridine and 6.7 ml of acetic anhydride. The solution was stirred at room temperature for 3 hours, and then the solvent was distilled off under reduced pressure. The residue was dissolved in 50 ml of ether, and the solution was washed with 3 ml of saturated aqueous sodium bicarbonate and 5 ml of aqueous copper sulfate, dried and concentrated to obtain 400 mg of the crude diacetate product.

The crude product was dissolved in a solution of 12 ml of acetonitrile, 6 ml of THF and 8 ml of ¼ N hydrochloric acid. The solution was stirred at room temperature for 4 hours and then allowed to stand overnight at −15° C. To the resulting solution was added 0.3 ml of triethylamine, 3 ml of saturated aqueous sodium bicarbonate and 5 ml of saturated aqueous sodium chloride, followed by extraction with 100 ml of ether. The ether extract was dried, concentrated and purified by column chromatography (Merck's Rober Column B, cyclohexane: ethyl acetate=1:1) to obtain 179.5 mg (54.5%) of the alcohol.

The alcohol was dissolved in 4 ml of dimeythylformamide, and to the solution was added 970 mg of pyridinium dichromate. The mixture was stirred overnight, and to the following mixture was added 6 ml of water, followed by extraction with 150 ml of ether. The extract was washed with 5 ml of saturated aqueous sodium chloride, dried and concentrated to obtain 200 mg of the carboxylic acid diacetate. The carboxylic acid diacetate was dissolved in 8 ml of methanol and 3 ml of 1 N aqueous sodium hydroxide. The solution was stirred overnight, and after the methanol was distilled off, washed with 1 ml of cyclohexane: ether (1:1). The aqueous solution was acidified with 4 ml of 1 N hydrochloric acid at 0° C. to pH 2-3, followed by extraction with 40 ml of ethyl acetate. The extract was dried and concentrated to obtain 135 mg of 5,6,7-trinor-4,8-inter-m-phenylene-17,18,19,20-tetranor-16-cyclohexyl $PGI_2$. The structure was confirmed by the following spectral data:

IR (Neat)$v$ cm$^{-1}$: 3600-2500, 2940, 1705, 1595, 1422, 1250, 1185, 1060, 1020, 965, 860, 740.

NMR (CDCl$_3$)$_{67}$ ppm: 0.9—1.5 (m, 8H9 1,6-2.1(m, 10H) 2.34 (t, 2H) 2.63 (t, 2H) 3.38 (t, 1H) 3.88 (dd,1H) 4.1 (m, 1H) 5.08 (m, 1H) 5.6 (m, 1H, $C_{13}HC_{14}N$) 5.75 (b, 3H) 6.65-7.1 (m, 3H).

EXAMPLES 23-29

The procedures of Example 3 were followed except the uses of cyclo pentyl methyl lithium, (3-methyl)-cyclo pentyl methyl lithium, (3-ethyl)-cyclo pentyl methyl lithium, (3-n-propyl)-cyclo pentyl methyl lithium, (3-methyl)-cyclo hexyl methyl lithium, (4-methyl)-cyclo hexyl methyl lithium and (4-ethyl)-cyclo hexyl methyl lithium in place of the cyclo hexyl methyl lithium used therein give the compounds:

5,6,7-trinor-4,8-inter-m-phenylene-17,18,19,20-tetranor-16-cyclopentyl $PGI_2$ (23),
5,6,7-trinor-4,8-inter-m-phenylene-17,18,19,20-tetranor-16-(3-methyl cyclo pentyl) $PGI_2$ (24),
5,6,7-trinor-4,8-inter-m-phenylene-17,18,19,20-tetranor-16-(3-ethyl cyclo pentyl) $PGI_2$, (25),
5,6,7-trinor-4,8-inter-m-phenylene-17,18,19,20-tetranor-16-(3-n-protyl cyclo pentyl) $PGI_2$ (26),
5,6,7-trinor-4,8-inter-m-phenylene-17,18,19,20-tetranor-16-(3-methyl cyclo hexyl) $PGI_2$ (27),
5,6,7-trinor-4,8-inter-m-phenylene-17,18,19,20-tetranor-16-(4-methyl cyclo hexyl) $PGI_2$ (28), and
5,6,7-trinor-4,8-inter-m-phenylene-17,18,19,20-tetranor-16-)4-ethyl cyclo hexyl) $PGI_2$ (29), respectively.

See Table 3.

TABLE 3

| Compound No. | IR ($vcm^{-1}$) | Mass (m/e) |
| --- | --- | --- |
| (23) | 3500-2500, 2920, 2850 1700, 1180, 1020, 970 740 | 400 |
| (24) | 3500-2500, 2920, 2850 1700, 1440, 1180, 1020 970, 740 | 414 |
| (25) | 3500-2500, 2920, 2850 1700, 1445, 1180, 1017 970, 740 | 428 |
| (26) | 3500-2500, 2920, 2850 1700, 1445, 1180, 1020 970, 740 | 442 |
| (27) | 3500-2500, 2920, 2850 1700, 1445, 1180, 1020 970, 740 | 428 |
| (28) | 3500-2500, 2920, 2850 1700, 1445, 970, 740 1180, 1020 | 428 |
| (29) | 3500-2500, 2920, 2850 1700, 1445, 1180, 1020 970, 740 | 442 |

EXAMPLE 30

5,6,7-trinor-4,8-inter-m-phenylene-17,18,19,20-tetranor-16-phenyl $PGI_2$ (30)

To a solution of 140 mg (0.636 mmol) of 3a,8b-cis-2,3,8a,8b-tetrahydro-1-H-5-(4-tetrahydropyranyloxybutyl)-1β-(2-formylethenyl)2α-hydroxycyclopenta[b-]benzofuran in 2.5 ml of THF at −78° C. was added 7.2 ml of 0.3N THF solution of benzyllithium. After completion of the addition, 0.5 ml of methanol, then 1 ml of saturated aqueous ammonium chloride and 4 ml of saturated aqueous sodium chloride, followed by extraction with 25 ml of ether. The ether extract was dried, concentrated and purified by column chromatography (Merck's Rober Column A, cyclohexane: ethyl acetate=2:5) to obtain 62.4 mg (36%) of the diol 15α isomer and 47.5 mg (27%) of the diol 15/β isomer.

The diol 15α isomer was dissolved in 1.5 ml of pyridine and 2.0 ml of acetic anhydride, and the solution was stirred at room temperature for 3 hours. The solvent was distilled off, and the residue was extracted with 10 ml of ether. The ether extract was washed with 3 ml of saturated aqueous sodium bicarbonate and 5 ml of aqueous copper sulfate, dried and concentrated to give 75 mg of the crude diacetate product.

To the crude product were added 5 ml of acetonitrile, 3 ml of THF and 3 ml of 1/10 N hydrochloric acid. The mixture was stirred at room temperature for 4 hours, and to the resulting mixture were added 0.1 ml of triethylamine, 3 ml of saturated aqueous sodium bicarbonate and 2 ml of saturated aqueous sodium chloride, followed by extraction with 100 ml of ether. The extract was washed with saturated aqueous sodium chloride, dried, concentrated and purified by column chromatography (Merck's Rober Column A, cyclohexane: ethyl acetate=1:1) to obtain 46.1 mg of the alcohol.

The alcohol was dissolved in 1 ml of dimethylformamide, and to the solution was added 290 mg of pyridinium dichromate. The mixture was stirred overnight at room temperature, followed by addition of 3 ml of water and extraction with 100 ml of ether. The extract was washed with 5 ml of saturated aqueous sodium chloride, dried and concentrated to give 33.3 mg of the carboxylic acid diacetate. To the carboxylic acid diacetate were added 3 ml of methanol and 1 ml ml of 1 N aqueous solution of sodium hydroxide. The mixture was stirred overnight at room temperature. The methanol was distilled off. The aqueous solution was washed with 1 ml of cyclohexane:ether (1:1), acidified with 1 N hydrochloric acid at 0° C. to pH 2-3- and extracted with ethyl acetate. Drying following by concentration gave 26.7 mg of 5,6,7-trinor-4,8-inter-m-phenylene-17,18,19,20-tetranor-16-phenyl $PGI_2$.

The structure was confirmed by the following spectral data:

IT (Neat)$\nu$ cm$^{-1}$: 3600-2500, 1700, 1440, 1180, 1020, 960, 850, 740, 698.

NMR (CDCl$_3$)$_{67}$ ppm: 1.9 (m, 3H) 2.38 (t, 2H) 2.6 (t, 2H) 2.8 (b, 2H) 3.3 (1H) 3.8 (1H) 4.2 (1H) 5.05 (1H) 5.6 (b, 5H) 6.65-7.0 (m, 3H) 7.3 (bs, 5H, C$_6$H$_5$).

Mass (m/e): 480 (M+), 299, 281.

EXAMPLES 31-80

The procedures of Example 1 were followed except the uses of p-methyl benzyl lithium, m-methyl benzyl lithium, p-ethyl benzyl lithium, m-ethyl benzyl lightium, m-chloro benzyl lithium, p-chloro benzyl lithium, m-bromo benzyl magnesium bromide, p-bromo benzyl magnesium bromide, p-fluoro benzyl lithium, m-methoxy benzyl magnesium bromide, p-methoxy benzyl magnesium bromide, o-phenoxy benzyl magnesium bromide, p-biphenyl methyl lithium, p-phenoxy benzyl magnesium bromide, α-naphthyl methyl magnesium bromide, 62-naphthyl methyl magnesium bromide, β-phenethyl magnesium bromide, 2-(p-methyl phenyl) ethyl magnesium bromide, 2-(m-methyl phenyl) ethyl magnesium bromide, 2-(p-ethyl phenyl) ethyl magnesium bromide, 2(m-ethyl phenyl) ethyl magnesium bromide, 2-(p-chloro phenyl) ethyl magnesium bromide, 2-(m-chloro phenyl) ethyl magnesium bromide, 2-(p-bromo phenyl) ethyl magnesium bromide, 2-(m-bromo phenyl) ethyl magnesium bromide, 2-(m-fluoro phenyl) ethyl magnesium bromide, 2-(p-fluoro phenyl) ethyl magnesium bromide, 2-(p-methoxy phenyl) ethyl magnesium bromide, 2-(m-methoxy phenyl) ethyl magnesium bromide, 2-(o-methoxy phenyl) ethyl magnesium bromide, 2-(p-biphenyl) ethyl magnesium bromide, 2-(p-phenoxy phenyl) ethyl magnesium bromide, 2-(α-naphthyl) ethyl magnesium bromide, 2-(β-naphthyl) ethyl magnesium bromide, 3-phenyl propyl magnesium bromide, 3-(p-methyl phenyl) propyl magnesium bromide, 3-(p-chloro phenyl) propyl magnesium bromide, 3-(m-chloro phenyl) propyl magnesium bromide, 3-(p-ethyl phenyl) propyl magnesium bromide, 3-(p-bromo phenyl) propyl magnesium bromide, 3-(m-bromo phenyl) propyl magnesium bromide, 3-(p-fluoro phenyl) propyl magnesium bromide, 3-(m-fluoro phenyl) propyl magnesium bromide, 3-(o-methoxy phenyl) propyl magnesium bromide, 3-(m-methoxy phenyl) propyl magnesium bromide, 3-(p-biphenyl) propyl magnesium bromide, 3-(p-phenoxy phenyl) propyl magnesium bromide, 3-(β-naphthyl) propyl magnesium bromide and 3-(β-naphthyl) propyl magnesium bromide in place of the phenyl lithium used therein to give the compounds:

5,6,7-trinor-4,8-inter-m-phenylene-17,18,19,20-tetranor-16-p-tolyl $PGI_2$ (31)

5,6,7-trinor-4,8-inter-m-phenylene-17,18,19,20-tetranor-16-m-tolyl $PGI_2$ (32), 5,6,7-trinor-4,8-inter-m-phenylene-17,18,19,20-tetranor-16-(p-ethyl phenyl) $PGI_2$ (33), 5,6,7-trinor-4,8-inter-m-phenylene-17,18,19,20-tetranor-16-(m-ethyl phenyl) $PGI_2$ (34), 5,6,7-trinor-4,8-inter-m-phenylene-17,18,19,20-tetranor-16-(m-chloro phenyl) $PGI_2$ (35), 5,6,7-trinor-4,8-inter-m-phenylene-17,18,19,20-tetranor-16-(p-chloro phenyl) $PGI_2$ (36), 5,6,7-trinor-4,8-inter-m-phenylene-17,18,19,20-tetranor-16-(m-bromo phenyl) $PGI_2$ (37), 5,6,7-trinor-4,8-inter-m-phenylene-17,18,19,20-tetranor-16-(p-bromo phenyl) $PGI_2$ (38), 5,6,7-trinor-4,8-inter-m-phenylene-17,18,19,20-tetranor-16-(p-fluoro phenyl) $PGI_2$ (38), 5,6,7-trinor-4,8-inter-m-phenylene-17,18,19,20-tetranor-16-(m-methoxy phenyl) $PGI_2$ (40), 5,6,7-trinor-4,8-inter-m-phenylene-17,18,19,20-tetranor-16-(p-methoxy phenyl) $PGI_2$ (41), 5,6,7-trinor-4,8-inter-m-phenylene-17,18,19,20-tetranor-16-(o-methoxy phenyl) $PGI_2$ (42), 5,6,7-trinor-4,8-inter-m-phenylene-17,18,19,20-tetranor-16-(p-phenyl phenyl) $PGI_2$ (43), 5,6,7-trinor-4,8-inter-m-phenylene-17,18,19,20-tetranor-16-(p-phenoxy) $PGI_2$ (44), 5,6,7-trinor-4,8-inter-m-phenylene-17,18,19,20-tetranor-16-(α-naphthyl) $PGI_2$ (45), 5,6,7-trinor-4,8-inter-m-phenylene-17,18,19,20-tetranor-16-(β-naphthyl) $PGI_2$ (46), 5,6,7-trinor-4,8-inter-m-phenylene-18,19,20-trinor-17-phenyl $PGI_2$ (47), 5,6,7-trinor-4,8-inter-m-phenylene-18,19,20-trinor-17-(p-totyl) $PGI_2$ (48), 5,6,7-trinor-4,8-inter-m-phenylene-18,19,20-trinor-17-(m-tolyl) $PGI_2$ (49), 5,6,7-trinor-4,8-inter-m-phenylene-18,19,20-trinor-17-(p-ethyl phenyl) $PGI_2$ (50), 5,6,7-trinor-4,8-inter-m-phenylene-18,19,20 -trinor-17-(m-ethyl phenyl) $PGI_2$ (51), 5,6,7-trinor-4,8-inter-m-phenylen-18,19,20-trinor-17-(p-chloro phenyl) $PGI_2$ (52), 5,6,7-trinor-4,8-inter-m-phenylene-18,19,20-trinor-17-(m-chloro phenyl) $PGI_2$ (53), 5,6,7-trinor-4,8-inter-m-phenylene-18,19,20-trinor-17-(p-bromo phenyl) $PGI_2$ (43), 5,6,7-trinor-4,8-inter-m-phenylene-18,19,20-trinor-17-(m-bromo phenyl) $PGI_2$ (55), 5,6,7-trinor-4,8-inter-m-phenylene-18,19,20-trinor-17-(m-fluoro phenyl) $PGI_2$ (56), 5,6,7-trinor-4,8-inter-m-phenylene-18,19,20-trinor-17-(p-fluoro phenyl) $PGI_2$ (57), 5,6,7-trinor-4,8-inter-m-phenylene-18,19,20-trinor-17-(p-methoxy phenyl) $PGI_2$ (58), 5,6,7-trinor-4,8-inter-m-phenylene-18,19,20-trinor-17-(m-methoxy phenyl) $PGI_2$ (59), 5,6,7-trinor-4,8-inter-m-phenylene-18,19,20-trinor-17-(o-methoxy phenyl) $PGI_2$ (60), 5,6,7-trinor-4,8-inter-m-phenylene-18,19,20-trinor-17-(p-phenyl phenyl) $PGI_2$ (61), 5,6,7-trinor-4,8-inter-m-phenylene-18,19,20-trinor-17-(p-phenoxy phenyl) $PGI_2$ (62), 5,6,7-trinor-4,8-inter-m-phenylene-18,19,20-trinor-17-(α-naphthyl) $PGI_2$ (63), 5,6,7-trinor-4,8-inter-n-phenylene-18,19,20-trinor-17-(β-napthyl) $PGI_2$ (64), 5,6,7-trinor-4,8-inter-m-phenylene-19,20-dinor-18-phenyl $PGI_2$ (65), 5,6,7-trinor-4,8-inter-m-phenylene-19,20-dinor-18-(p-chloro phenyl) PGI$_2$ (66),
5,6,7-trinor-4,8-inter-m-phenylene-19,20-dinor-18-(m-chloro phenyl) PGI$_2$ (67),
5,6,7-trinor-4,8-inter-m-phenylene-18,20-dinor-18-(p-ethyl phenyl) PGI$_2$ (68),
5,6,7-trinor-4,8-inter-mphenylene-19,20-dinor-18-(m-ethyl phenyl) PGI$_2$ (69),
5,6,7-trinor-4,8-inter-m-phenylene-19,20-dinor-18-(p-bromo phenhy) PGI$_2$ (70),
5,6,7-trinor-4,8-inter-m-phenylene-19,20-dinor-18-(m-bromo phenyl) PGI$_2$ (71(,
5,6,7-trino-4,8-inter-m-phenylene-19,20-dinor-18-(p-fluoro phenyl) PGI$_2$ (72),
5,6,7-trinor-4,8-inter-m-phenylene-19,20-dinor-18-(m-fluoro phenyl) PGI$_2$ (73),
5,6,7-trinor-b 4,8-inter-m-phenylene-19,20-dinor-18-(o-methoxy phenyl) PGI$_2$ (74),
5,6,7-trinor-4,8-inter-m-phenylene-19,20-dinor-18-(m-methoxy phenyl) PGI$_2$ (75),
5,6,7-trinor-4,8-inter-m-phenylene-19,20-dinor-18-(p-methoxy phenyl) PGI$_2$ (76),
5,6,7-trinor-4,8-inter-m-phenylene-19,20-dinor-18-(p-phenyl phenyl) PGI$_2$ (77),
5,6,7-trinor-4,8-inter-m-phenylene-19,20-dinor-18-(p-phenoxy phenyl) PGI$_2$ (78),
5,6,7-trinor-4,8-inter-m-phenylene-19,20-dinor-18-($\alpha$-naphthyl) PGI$_2$ (79), and
5,6,7-trinor-4,8-inter-m-phenylene-19,20-dinor-18-($\beta$-naphthyl) PGI$_2$ (80), respectively. See Table 4.

TABLE 4

| Compound No. | IR ($\nu$ cm$^{-1}$) | Mass (m/e) |
| --- | --- | --- |
| (31) | 3600–2500, 1700, 1440 1180, 1020, 960, 850 740, 698 | 422 |
| (32) | 3600–2500, 1700, 1440 1180, 1020, 960, 850 740, 698 | 422 |
| (33) | 3600–2500, 1700 1440 1180, 1020, 960, 850 740, 698 | 436 |
| (34) | 3600–2500, 1700, 1440 1180, 1020, 960, 850 740, 698 | 436 |
| (35) | 3600–2500, 1700, 1440 1180, 1020, 960, 850 740, 698 | 444, 442 |
| (36) | 3600–2500, 1700, 1440 1180, 1020, 960, 850 740, 698 | 444, 442 |
| (37) | 3600–2500, 1700, 1440 1180, 1020, 960, 850 740, 698 | 486, 488 |
| (38) | 3600–2500, 1700, 1440 1180, 1020, 960, 850 740, 698 | 486, 488 |
| (39) | 3600–2500, 1700, 1440 1180, 1020, 960, 850 740, 698 | 426 |
| (40) | 3600–2500, 1700, 1440 1180, 1020, 960, 850 740, 698 | 438 |
| (41) | 3600–2500, 1700, 1440 1180, 1020, 960, 850 740, 698 | 438 |
| (42) | 3600–2500, 1700, 1440 1180, 1020, 960, 850 740, 698 | 438 |
| (43) | 3600–2500, 1700, 1600 1440, 1180, 1020, 960 850, 740, 698 | 484 |
| (44) | 3600–2500, 1700, 1600 1440, 1180, 1020, 960 850, 740, 698 | 500 |

TABLE 4-continued

| Compound No. | IR ($\nu$ cm$^{-1}$) | Mass (m/e) |
| --- | --- | --- |
| (45) | 3600–2500, 1700, 1605 1440, 1180, 1020, 960 850, 740, 698 | 458 |
| (46) | 3600–2500, 1700, 1595 1440, 1180, 1020, 960 850, 740, 698 | 458 |
| (47) | 3600–2500, 1700, 1595 1440, 1180, 1020, 960 850, 740, 698 | 422 |
| (48) | 3600–2500, 1700, 1595 1440, 1180, 1020, 960 850, 740, 698 | 436 |
| (49) | 3600–2500, 1700, 1595 1440, 1180, 1020, 960 850, 740, 698 | 436 |
| (50) | 3600–2500, 1700, 1595 1440, 1180, 1020, 960 850, 740, 698 | 450 |
| (51) | 3600–2500, 1700, 1595 1440, 1180, 1020, 960 850, 740, 698 | 450 |
| (52) | 3600–2500, 1700, 1595 1440, 1180, 1020, 960 850, 740, 698 | 458, 456 |
| (53) | 3600–2500, 1700, 1595 1440, 1180, 1020, 960 850, 740, 698 | 458, 456 |
| (54) | 3600–2500, 1700, 1595 1440, 1180, 1020, 960 850, 740, 698 | 500, 502 |
| (55) | 3600–2500, 1700, 1595 1440, 1180, 1020, 960 850, 740, 698 | 500, 502 |
| (56) | 3600–2500, 1700, 1595 1440, 1180, 1020, 960 850, 740, 698 | 440 |
| (57) | 3600–2500, 1700, 1595 1440, 1180, 1020, 960 850, 740, 698 | 440 |
| (58) | 3600–2500, 1700, 1595 1440, 1180, 1020, 960 850, 740, 698 | 452 |
| (59) | 3600–2500, 1700, 1595 1440, 1180, 1020, 960 850, 740, 698 | 452 |
| (60) | 3600–2500, 1700, 1595 1440, 1180, 1020, 960 850, 740, 698 | 452 |
| (61) | 3600–2500, 1700, 1595 1440, 1180, 1020, 960 850, 740, 698 | 498 |
| (62) | 3600–2500, 1700, 1595 1440, 1180, 1020, 960 850, 740, 698 | 514 |
| (63) | 3600–2500, 1700, 1600 1590, 1440, 1180, 1020 960, 850, 740, 698 | 472 |
| (64) | 3600–2500, 1700, 1600 1590, 1440, 1180, 1020 960, 850, 740, 698 | 472 |
| (65) | 3600–2500, 1700, 1595 1440, 1180, 1020, 960 850, 740, 698 | 436 |
| (66) | 3600–2500, 1700, 1595 1440, 1180, 1020, 960 850, 740, 698 | 472, 470 |
| (67) | 3600–2500, 1700, 1595 1440, 1180, 1020, 960 850, 740, 698 | 472, 470 |
| (68) | 3600–2500, 1700, 1595 1440, 1180, 1020, 960 850, 740, 698 | 464 |
| (69) | 3600–2500, 1700, 1595 1440, 1180, 1020, 960 850, 740, 698 | 464 |
| (70) | 3600–2500, 1700, 1595 1440, 1180, 1020, 960 850, 740, 698 | 514, 516 |
| (71) | 3600–2500, 1700, 1595 1440, 1180, 1020, 960 850, 740, 698 | 514, 516 |

TABLE 4-continued

| Compound No. | IR ($\nu$ cm$^{-1}$) | Mass (m/e) |
|---|---|---|
| (72) | 1440, 1180, 1020, 960 850, 740, 698 3600–2500, 1700, 1595 | 454 |
| (73) | 1440, 1180, 1020, 960 850, 740, 698 3600–2500, 1700, 1595 | 454 |
| (74) | 1440, 1180, 1020, 960 850, 740, 698 3600–2500, 1700, 1595 | 466 |
| (75) | 1440, 1180, 1020, 960 850, 740, 698 3600–2500, 1700, 1595 | 466 |
| (76) | 1440, 1180, 1020, 960 850, 740, 698 3600–2500, 1700, 1595 | 466 |
| (77) | 1440, 1180, 1020, 960 850, 740, 698 3600–2500, 1700, 1595 | 512 |
| (78) | 1440, 1180, 1020, 960 850, 740, 698 3600–2500, 1700, 1600 | 528 |
| (79) | 1590, 1440, 1180, 1020 960, 850, 740, 698 3600–2500, 1700, 1600 | 486 |
| (80) | 1590, 1440, 1180, 1020 960, 850, 740, 698 | 486 |

EXAMPLE 81

5,6,7-trinor-4,8-inter-m-phenylene-13,14-dihydro-16,17,18,19,20-pentanor-15-cyclohexyl PGI$_2$ (81)

To a solution of 30 mg (0.075 mmol) of 5,6,7-trinor-4,8-inter-m-phenylene-16,17,18,19,20-pentanor-15-cyclohexyl PGI$_2$ (2) in 1 ml of methanol was added ca. 5 mg palladium (10%)-carbon, and the mixture was stirred under hydrogen for 2 hours. The resulting mixture was filtered concentrated and purified by column chromatography (Merck's Rober Column A, cyclohexane:ethyl acetate=1:3) to obtain 13.5 mg. of the desired product.

The structure was confirmed by the following spectral data after converting the product with diazomethane to its methyl ester:

IR (Neat) $\nu$cm$^{-1}$: 3600–3300, 2920, 2840, 1735, 1590, 1440, 745.

NMR (CDCl$_3$) $\delta$ppm: 0.9–1.5 (m, 8H) 1.6–2.1 (m, 10H) 2.35 (t, 2H) 2.62 (t, 2H) 3.4 (m, 1H) 3.65 (s, 3H) 4.02 (q, 1H) 5.16 (m, 1H) 6.7–7.1 (m, 3H)

Mass (m/e): 416 (M+).

EXAMPLES 82–89

The procedures of Example 81 were followed except that the starting material (2) was replaced by 12, 15, 22, 25, 30, 31, 45 and 63 to give the compounds:

5,6,7-trinor-4,8-inter-m-phenylene-13,14-dihydro-16,17,18,19,20-pentanor-15-cyclopentyl PGI$_2$ (82), 5,6,7-trinor-4,8-inter-m-phenylene-13,14-dihdyro-16,17,18,19,20-pentanor-15-(3-ethyl cyclopentyl) PGI$_2$ (83), 5,6,7-trinor-4,8-inter-m-phenylene-13,14-dihydro-17,18,19,20-tetranor-16-cyclohexyl PGI$_2$ (84), 5,6,7-trinor-4,8-inter-m-phenylene-13,14-dihydro-17,18,19,20-tetranor-16-(3-ethyl cyclopentyl) PGI$_2$ (85), 5,6,7-trinor-4,8-inter-m-phenylene-13,14-dihydro-17,18,19,20-tetranor-16-phenyl PGI$_2$ (86), 5,6,7-trinor-4,8-inter-m-phenylene-13,14-dihydro-17,18,19,20-tetranor-16-(p-tolyl) PGI$_2$ (87), 5,6,7-trinor-4,8-inter-m-phenylene-13,14-dihydro-17,18,19,20-tetranor-16-($\alpha$-naphthyl) PGI$_2$ (88), and 5,6,7-trinor-4,8-inter-m-phenylene-13,14-dihydro-18,19,20-trinor-17-($\alpha$-naphthyl) PGI$_2$ (89), respectively. See Table 5.

TABLE 5

| Compound No. | IR ($\nu$cm$^{-1}$) | Mass (m/e) |
|---|---|---|
| (82) | 3600–2500, 1710, 745 | 388 |
| (83) | 3600–2500, 1710, 745 | 416 |
| (84) | 3600–2500, 1710, 745 | 416 |
| (85) | 3600–2500, 1710, 745 | 430 |
| (86) | 3600–2500, 1710, 740 700 | 410 |
| (87) | 3600–2500, 1710, 810 740 | 424 |
| (88) | 3600–2500, 1710, 795 745 | 460 |
| (89) | 3600–2500, 1710, 795 745 | 474 |

EXAMPLE 90

2-decarboxy-2-tetrahydropyranyloxymethyl-5,6,7-trinor-4,8-inter-m-phenylene-16,17,18,19,20-pentanor-15-p-tolyl PGI$_2$ To a solution of 195 mg (0.506 mmol) of 3a,8b-cis-2,3,3a,8b-tetrahydro-1H-5-(4-tetrahydro-pyranyloxy-n-butyl)-1$\beta$-(2-formyl-ethenyl)-2$\alpha$-hydrocycyclopenta[b-]benzofuran in 5 ml of THF cooled to $-78°$ C. was added 1.5 ml (1.98 mmol) of 1.32 M ether solution of p-tolyl lithium. The mixture was stirred at $-78°$ C. for 1.5 hours, followed by addition of 0.5 ml of methanol and 1.0 ml of saturated aqueous ammonium chloride. The reaction mixture was then extracted with ether, and the ether extract was dried over anhydrous sodium sulfate and concentrated. The residue was purified by column chromatography (Merck's Robet Column B, cyclohexane:ethyl acetate:isopropyl alcohol=1:4:0.2) to give 167 mg of an epimer mixture of the title compound (69%, $\alpha$:$\beta$=2:1).

TLC: Rf: $\alpha$0.38 (cyclohexane:ethyl acetate 1:4). $\beta$0.43 (cyclohexane:ethyl acetate 1:4).

EXAMPLE 91

2-decarboxy-2-tetrahydropyranyloxymethyl-15-dehydroxy-15-oxo-5,6,7-trinor-4,8-inter-m-phenylene-16,17,18,19,20-pentanor-15-p-tolyl PGI$_2$ To a solution of 240 mg (0.503 mmol) of 2-decarboxy-2-tetrahydropyranyloxymethyl-5,6,7-trinor-4,8-inter-m-phenylene-16,17,18,19,20-pentanor-15-p-tolyl PGI$_2$ in 20 ml of CH$_2$Cl$_2$ was added 7 g of manganese dioxide. The mixture was stirred at room temperature for 2 hours. The manganese dioxide was separated by filtration using a glass column filled with 30 g of silica gel and thoroughly washed with ethyl acetate. The combined filtrate and washings were concentrated to give 175 mg of the title compound (0.368 mmol, 73%).

TLC Rf=0.60 (cyclohexane:ethyl acetate=1:2).

IR (liquid film) $\nu$cm$^{-1}$: 3600–3200, 3020, 2930, 2850, 1670, 1620, 1570, 1450, 1250, 980, 865, 815, 745.

EXAMPLE 92

2-decarboxy-2-tetrahydroxypyranyloxymethyl-11-acetyl-15-dehydro-15-oxo-5,6,7-trinor-4,8-inter-m-phenylene-16,17,18,19,20-pentanor-15-p-tolyl PGI$_2$ To a solution of 175 mg (0.368 mmol) of 2-decarboxy-2-tetrahydropyranyloxymethyl-15-dehydroxy-15-oxo- 5,6,7-trinor-4,8-inter-m-phenylene-16,17,18,19,20-pentanor-15-(p-tolyl) $PGI_2$ in 2 ml of pyridine added 2 ml of acetic anhydride and the solution was stirred at room temperature for 1 hour. The solvent was distilled off, and the residue was dissolved in 50 ml of ether. The solution was washed successively with 5 ml of saturated aqueous sodium hydrogen carbonate, 5 ml of saturated aqueous copper sulfate and 5 ml of saturated aqueous sodium chloride, dried over anhydrous magnesium sulfate and concentrated to give 171 mg (0.331 mmol, 90%) of the title compound.

TLC Rf=0.51 (cyclohexane:ethyl acetate=1:1).

EXAMPLE 93

2-decarboxy-2-hydroxymethyl-11-acetyl-15-dehydroxy-15-oxo-5,6,7-trinor-4,8-inter-m-phenylene-16,17,18,19,20-pentanor-15-p-tolyl $PGI_2$ To 171 mg of 2-decarboxy-2-tetrahydro-pyranyloxymethyl-11-acdtyl-15-dihydroxy-15-oxo-5,6,7-trinor-4,8-inter-m-phenylene-16,17,18,19,20-pentanor-15-p-tolyl $PGI_2$ was added 7.5 ml of acetic acid:water (2:1). The mixture was stirred with warming at 40° C. for 3 hours. The solvent was distilled off, and the residue was purified by column chromatography (10 g of silica gel, cyclohexane:ethyl acetate=3:2) to give 69 mg. of the title compound.

TLC Rf=0.43 (cyclohexane:ethyl acetate=1:1).

IR (liquid film) $vcm^{-1}$: 3600-3200, 3030, 2920, 2850, 1735, 1665, 1615, 1605, 1445, 1230, 1050, 970, 815, 740.

NMR ($CDCl_3$)δppm, (TMS): 1.2-2.0 (m, 8H) 1.79 (s, 3H) 2.43 (s, 3H) 2.63 (m, 2H) 3.10 (m, 1H) 3.70 (t, 2H) 5.1 (m, 1H) 5.3 (m, 1H) 6.8-8.0 (m, 9H).

EXAMPLE 94

11-acetyl-15-dehydroxy-15-oxo-5,6,7-trinor-4,8-inter-m-phenylene-16,17,18,19,20-pentanor-15-p-tolyl $PGI_2$ To a solution of 61 mg (0.141 mmol) of 2-decarboxy-2-hydroxymethyl-11-acetyl-15-acetyl-15-dehydroxy-15-oxo-5,6,7-trinor-4,8-inter-m-phenylene-16,17,18,19,20-pentanor-15-(p-tolyl) $PGI_2$ in 1 ml of dimethylformamide was added 420 mg of pyridinium dichromate. The mixture was stirred overnight at room temperature, followed by addition of 3 ml of water. The resulting mixture was extracted with ether (7×10 ml), and the ether layer was washed with saturated aqueous sodium chloride (3×3 ml), dried over anhydrous sodium sulfate and concentrated to give 39 mg of the title compound (0.0864 mmol, 62%).

TLC Rf=0.40 (cyclohexane:ethyl acetate=1:2).

EXAMPLE 95

11-acetyl-15-dehydroxy-15-oxo-5,6,7-trinor-4,8-inter-m-phenylene-16,17,18,19,20-pentanor-15-p-tolyl $PGI_2$ benzyl ester To a solution of 35 mg (0.0781 mmol) of 11-acetyl-15-dehydroxy-15-oxo-5,6,7-trinor-4,8-inter-m-phenylene-16,17,18,19,20-pentanor-15-(p-tolyl) $PGI_2$ in 1 ml of dimethylformamide were added 100 μl of triethylamine and 100 μl of benzyl brmoide. The mixture was stirred at room temperature for 5 hours, followed by addition of 3 ml of water. The resulting mixture was extracted with ether, and the ether layer was washed successively with 1 N hydrochloric acid and saturated aqueous sodium chloride, dried over anhydrous sodium sulfate and concentrated. The residue was purified by column chromatography (Merck's Rober Column, Size A: cyclohexane:ethyl acetate=3:2) to afford 15 mg (0.0279 mmol, 36%) of the title compound.

TLC: Rf=0.58 (cyclohexane:ethyl acetate=1:1).

IR (liquid film) $vcm^{-1}$: 3030, 2930, 2850, 1740, 1670, 1620, 1605, 1450, 1230, 1030, 980, 820, 750, 700.

NMR ($CDCl_3$) δppm (TMS): 1.76 (s, 3H) 1.9-2.1 (m, 3H) 2.3-2.8 (m, 6H) 2.43 (s, 3H) 3.75 (m, 1H). 5.1-5.4 (m, 2H) 5.11 (s, 2H) 6.7-7.9 (m, 14H).

EXAMPLE 96

11-acetyl-5,6,7-trinor-4,8-inter-m-phenylene-16,17,18,19,20-pentanor-15-(p-tolyl) $PGI_2$ benzyl ester (90)

To a solution of 6 mg (0.0112 mmol) of 11-acetyl-15-dehydroxy-15-oxo-5,6,7-trinor-4,8-inter-m-phenylene-16,17,18,19,20-pentanor-15-(p-tolyl) $PGI_2$ benzyl ester in 0.8 ml of methanol was added 8 mg (0.0215 mmol) of cerium trichloride ($CeCl_3.7H_2O$) to a complete solution. To the solution was added 2 mg (0.0528 mmol) of sodium borohydride, and the mixture was stirred at room temperature for 15 minutes, followed by addition of 5 ml of saturated aqueous sodium hydrogen carbonate. The resulting mixture was extracted with ether, and the ether layer was washed with water, dried over anhydrous sodium sulfate and concentrated. There was obtained 6 mg (0.0111 mmol, ca. 100%) of an epimer mixture of the title compound.

TLC: Rf=0.52 (cyclohexane:ethyl acetate=1:1).

IR (liquid film) $vcm^{-1}$: 3600-3200, 3030, 2920, 2850, 1730, 1590, 1450, 1250, 1020, 970, 815, 740, 700.

EXAMPLE 97

5,6,7-trinor-4,8-inter-m-phenylene-16,17,18,19,20-pentanor-15-(p-tolyl) $PGI_2$ methyl ester (91)

To a solution of 6 mg (0.0111 mmol) of the compound 90 in dry methanol was added 50 μl of 0.5 M aqueous solution of sodium methoxide. The mixture was stirred at room temperature for 1 hour. To the resulting mixture was added a carboxylic ion exchange resin (IRC-50). The mixture was stirred for 20 minutes, and then filtered to separate the ion exchange resin. The filtrate was concentrated, and the residue was purified by thin layer chromatography for separative use to afford 1.5 mg (0.0036 mmol, 32%) of the 15α isomer (more molar) and 2.0 mg (0.0047 mmol, 43%) of the 15β isomer (less polar) of the title compound.

15α isomer: TLC: Rf=0.27 (cyclohexane:ethyl acetate=1:3).

IR (liquid film) $vcm^{-1}$: 3600-3100, 3030, 2930, 2850, 1730, 1600, 1510, 1450, 1260, 1190, 1030, 970, 865, 810, 750, 705.

Mass (m/e): 422 ($M^+$), 404 ($M^+$-18), 350, 328, 273, 232, 218, 171, 158, 144, 131, 129.

15β isomer: TLC Rf=0.33 (cyclohexane:ethyl acetate=1:3).

IR (liquid film) $vcm^{-1}$: 3600-3100, 3030, 2930, 2850, 1730, 1600, 1510, 1450, 1260, 1190, 1030, 970, 860, 825, 750, 705.

Mass (m/e): 404($M^+$-18), 386, 350, 328, 273, 232, 171, 158, 144, 131, 129.

EXAMPLE 98-101

The procedures of Examples 90-97 were followed except that in place of the p-tolyllithium used in Example 87 was used 3.4-dimethylphenyl lithium, 3,5-dimethyl phenyl lithium, o-methoxy phenyl lithium and p-methoxy phenyl lithium to give the compounds:

5,6,7-trinor-4,8-inter-m-phenylene-16,17,18,19,20-pentanor-15-(3,4-dimethyl phenyl) PGI$_2$ methyl ester (92),
5,6,7-trinor-4,8-inter-m-phenylene-16,17,18,19,20-pentanor-15-(3,5-dimethyl phenyl) PGI$_2$ methyl ester (93),
5,6,7-trinor-4,8-inter-m-phenylene-16,17,18,19,20-pentanor-15-(o-methoxy phenyl) PGI$_2$ methyl ester (94), and
5,6,7-trinor-4,8-inter-m-phenylene-16,17,18,19,20-pentanor-15-(p-methoxy phenyl) PGI$_2$ methyl ester (95), respectively.
See Table 6.

TABLE 6

| Compound No. | IR ($v$cm$^{-1}$) | Mass (m/e) |
|---|---|---|
| (92) | 3600–3100, 1735, 970 880, 855, 750 | 436 |
| (93) | 3600–3100, 1735, 970 845, 750, 690 | 436 |
| (94) | 3600–3100, 1735, 970 750 | 438 |
| (95) | 3600–3100, 1735, 970 820, 750 | 438 |

EXAMPLE 102

5,6,7-trinor-4,8-inter-m-phenylene-16,17,18,19,20-pentanor-15-(p-tolyl) PGI$_2$ (96)

To a solution of 1.5 mg of the compound 91 in 0.2 ml of methanol was added 0.1 ml of 1 N aqueous solution of sodium hydroxide. The mixture was stirred overnight at room temperature. The methanol was removed under reduced pressure from the reaction mixture, which was then cooled to 0° C., acidified with 1 N hydrochloric acid to pH 3.5 and extracted with ethyl acetate (3×0.2 ml). The combined ethyl acetate extracts were dried over anhydrous sodium sulfate and concentrated to give as a pale yellow oily material 1.1 mg of the title compound.

IR(liquid film) $v$ cm$^{-1}$. 3350, 2920, 2840, 1705, 1445, 860, 815, 730.

NMR (CDCl$_3$) $\delta$ ppm: 1.8–2.8 (12H) 6.60–7.00 (3H) 3.44 (1H, t) 7.22 (4H) 3.80–4.35 (4H) 5.16 (2H) 5.76 (2H).

Mass (m/e): 408.

EXAMPLES 103–106

The procedures of Example 102 were followed except that in place of the starting material 90 used therein was used the compounds 92, 93, 94, and 95 to give the compounds:
5,6,7-trinor-4,8-inter-m-phenylene-16,17,18,19,20-pentanor-15-(3,4-dimethyl phenyl) PGI$_2$ (97),
5,6,7-trinor-4,8-inter-m-phenylene-16,17,18,19,20-pentanor-15-(3,4-dimethyl phenyl) PGI$_2$ (98),
5,6,7-trinor-4,8-inter-m-phenylene-16,17,18,19,20-pentanor-15-(o-methoxy phenyl) PGI$_2$ (99), and
5,6,7-trinor-4,8-inter-m-phenylene-16,17,18,19,20-pentanor-15-(p-methoxy phenyl) PGI$_2$ (100), respectively.
See Table 7.

TABLE 7

| Compound No. | IR ($v$cm$^{-1}$) | Mass (m/e) |
|---|---|---|
| (97) | 3600–2500, 1710, 965 880, 855, 750 | 422 |
| (98) | 3600–2500, 1710, 965 845, 750, 590 | 422 |
| (99) | 3600–2500, 1710, 965 750 | 424 |
| (100) | 3600–2500, 1710, 965 820, 750 | 424 |

EXAMPLE 107

5,6,7-trinor-4,8-inter-m-phenylene-16,17,18,19,20-pentanor-15-cyclohexyl PGI$_2$ methyl ester (101)

To a solution of 500 mg (1.25 mmol) of 5,6,7-trinor-4,8-inter-m-phenylene-16,17,18,19,20-pentanor-15-cyclohexyl PGI$_2$ (2) in methanol was slowly added an ether solution of diazomethane. The mixture was concentrated and purified by column chromatography (Merck's Rober Column B, ethyl acetate) to afford 467 mg (90%) of the desired product. The structure was confirmed by the following spectral data:

IR (Neat $v$ cm$^{-1}$: 3600–3300, 2920, 2840, 1740, 965.

NMR (CDCl$_3$) $\delta$ ppm: 0.9–1.5 (m, 8H) 1.6–2.1 (m, 8H) 2.35 (t, 2H) 2.64 (t, 2H) 3.40 (t, 1H) 3.65 (s, 3H) 5.1 (m, 1H) 5.6 (m, 2H) 6.7–7.1 (m, 3H).

Mass (m/e): 414 (M$^+$).

EXAMPLES 108–111

The procedures of Example 107 were followed except that in place of the starting compound 2 used therein were used the compounds 1, 22, 30 and 47 to give the compounds:
5,6,7-trinor-4,8-inter-m-phenylene-16,17,18,19,20-pentanor-15-phenyl PGI$_2$ methyl ester (102),
5,6,7-trinor-4,8-inter-m-phenylene-17,18,19,20-tetranor-16-cyclohexyl PGI$_2$ methyl ester (103),
5,6,7-trinor-4,8-inter-m-phenylene-17,18,19,20-tetranor-16-phenyl PGI$_2$ methyl ester (104), and
5,6,7-trinor-4,8-inter-m-phenylene-18,19,20-trinor-17-phenyl PGI$_2$ methyl ester (105), respectively.
See Table 8.

TABLE 8

| Compound No. | IR ($v$ cm$^{-1}$) | Mass (m/e) |
|---|---|---|
| (102) | 3600–3300, 1735, 965 750, 705 | 408 |
| (103) | 3600–3300, 1040, 965 745 | 428 |
| (104) | 3600–3300, 1735, 965 750, 700 | 422 |
| (105) | 3600–3300, 1735, 965 750, 700 | 436 |

EXAMPLE 112

5,6,7-trinor-4,8-inter-m-phenylene-16,17,18,19,20-pentanor-15-cyclohexyl PGI$_2$ benzyl ester (106)

To a solution of 35 mg of 5,6,7-trinor-4,8-inter-m-phenylene-16,17,18,19,20-pentanor-15-cyclohexyl PGI$_2$ (2) in 1 ml of dimethylformamide were added 100 μl of triethylamine and 100 μl of benzyl bromide. The mixture was stirred at room temperature for 5 hours. After completion of the reaction, 3 ml of water was added, and the mixture was extracted with ether. The ether layer was dried (Na$_2$SO$_4$) and concentrated to afford a crude product of 106. Purification by column chromatography (silica gel: developing solvent, ethyl acetate) gave 30 mg of a pure title compound (106).

IR (liquid film) $v$ cm$^{-1}$: 3350, 1735, 965, 760, 695.

Mass m/e: 490.

EXAMPLES 113-116

The procedures of Example 112 were followed except that in place of the starting compound used therein were used the compounds 1, 22, 30 and 47 to give the compounds:

5,6,7-trinor-4,8-inter-m-phenylene-16,17,18,19,20-pentanor-15-phenyl $PGI_2$ benzyl ester (107), 5,6,7-trinor-4,8-inter-m-phenylene-17,18,19,20-tetranor-cyclohexyl $PGI_2$ benzyl ester (108), 5,6,7-trinor-4,8-inter-m-phenylene-17,18,19,20-tetranor-16-phenyl $PGI_2$ benzyl ester (109), and 5,6,7-trinor-4,8-inter-m-phenylene-18,19,20-trinor-17-phenyl $PGI_2$ benzyl ester (110), respectively.

See Table 9.

TABLE 9

| Compound No. | IR ($\nu$ cm$^{-1}$) | Mass (m/e) |
|---|---|---|
| (107) | 3600-3200, 1730, 970, 740, 700 | 484 |
| (108) | 3600-3200, 1730, 970, 740, 700 | 504 |
| (109) | 3600-3200, 1730, 970, 745, 700 | 498 |
| (110) | 3600-3200, 1730, 970, 745, 700 | 512 |

EXAMPLE 117

5,6,7-trinor-4,8-inter-m-phenylene-16,17,18,19,20-pentanor-15-cyclohexyl $PGI_2$ (2-pyridyl methyl) ester (111)

To a solution of 350 mg of 5,6,7-trinor-4,8-inter-m-phenylene-16,17,18,19,20-pentanor-15-cyclohexyl $PGI_2$ (2) in 4 ml of dry tetrahydrofuran cooled with ice were added 0.16 ml of triethylamine and 0.09 ml of ethyl chloroformate. The mixture was stirred at room temperature for 20 minutes. To the reaction mixture was added 0.4 ml of 2-pyridylmethanol. The mixture was stirred under argon at 60° C. for 14 hours. After cooled, ethyl acetate was added, and the mixture was washed with water and then with saturated aqueous solution of sodium hydrogen carbonate, dried ($Na_2SO_4$) and concentrated to give 700 mg of an oily material. The oil was separated by column chromatography (silica gel; ethyl acetate: isopropanol: methanol=97:3:0.5) to afford as a pale yellow oily material 300 mg of the title compound 111.

IR(liquid film) $\nu$ cm$^{-1}$: 3350, 1735, 1590, 965.
Mass m/e: 491.

EXAMPLES 118-121

The procedures of Example 117 were followed except that in place of the starting compound (2) used therein were used the compounds 1, 22, 30 and 47 to give the compounds:

5,6,7-trinor-4,8-inter-m-phenylene-16,17,18,19,20-pentanor-15-phenyl $PGI_2$ (2-pyridyl methyl) ester (112), 5,6,7-trinor-4,8-inter-m-phenylene-17,18,19,20-tetranor-16-cyclohexyl $PGI_2$ (2pyridyl methyl) ester (113), 5,6,7-trinor-4,8-inter-m-phenylene-17,18,19,20-tetranor-16-phenyl $PGI_2$ (2-pyridyl methyl) ester (114), and 5,6,7-trinor-4,8-inter-m-phenylene-18,19,20-trinor-17-phenyl $PGI_2$ (2-pyridyl methyl) ester (115), respectively.

See Table 10.

TABLE 10

| Compound No. | IR ($\nu$ cm$^{-1}$) | Mass (m/e) |
|---|---|---|
| (112) | 3300, 1740, 1595, 1575, 965 | 485 |
| (113) | 3300, 1740, 1595, 1575, 965 | 505 |
| (114) | 3300, 1740, 1595, 1575, 965 | 499 |
| (115) | 3300, 1740, 1595, 1575, 965 | 513 |

EXAMPLES 122-132

The procedures of Example 117 were followed except that in place of the 2-pyridyl methanol used therein were used butanol, octanol, cyclo hexyl methanol, cyclo pentyl methanol, 2-methoxy ethanol, methyl glycolate, methyl lacetate, 2-butyn-1-ol, 1,3-di-(O)-acetyl glycerin, phenol and p-acetamino phenol to give the compounds:

5,6,7-trinor-4,8-inter-m-phenylene-16,17,18,19,20-pentanor-15-cyclohexyl $PGI_2$ butyl ester (116), 5,6,7-trinor-4,8-inter-m-phenylene-16,17,18,19,20-pentanor-15-cyclohexyl $PGI_2$ octyl ester (117), 5,6,7-trinor-4,8-inter-m-phenylene-16,17,18,19,20-pentanor-15-cyclohexyl $PGI_2$ cyclohexylmethyl ester (118), 5,6,7-trinor-4,8-inter-m-phenylene-16,17,18,19,20-pentanor-15-cyclohexyl $PGI_2$ cyclopentylmethyl ester (119), 5,6,7-trinor-4,8-inter-m-phenylene-16,17,18,19,20-pentanor-15-cyclohexyl $PGI_2$ (2methoxy ethyl) ester (120), 5,6,7-trinor-4,8-inter-m-phenylene-16,17,18,19,20-pentanor-15-cyclohexyl $PGI_2$ carbomethoxymethyl ester (121), 5,6,7-trinor-4,8-inter-m-phenylene-16,17,18,19,20-pentanor-15-cyclohexyl $PGI_2$ (1-carbomethoxy ethyl) ester (122), 5,6,7-trinor-4,8-inter-m-phenylene-16,17,18,19,20-pentanor-15-cyclohexyl $PGI_2$ (2-butynyl) ester (123), 5,6,7-trinor-4,8-inter-m-phenylene-16,17,18,19,20-pentanor-15-cyclohexyl $PGI_2$ (1,3-diacetoxy-2-propyl) ester (124), 5,6,7-trinor-4,8-inter-m-phenylene-16,17,18,19,20-pentanor-15-cyclohexyl $PGI_2$ phenyl ester (125), and 5,6,7-trinor-4,8-inter-m-phenylene-16,17,18,19,20-pentanor-15-cyclohexyl $PGI_2$ (p-acetoamino phenyl) ester (126), respectively.

See Table 11.

TABLE 11

| Compound No. | IR ($\nu$ cm$^{-1}$) | Mass (m/e) |
|---|---|---|
| (116) | 3300, 1740, 1595, 965 | 456 |
| (117) | 3300, 1740, 1595, 965 | 512 |
| (118) | 3300, 1740, 1595, 965 | 496 |
| (119) | 3300, 1740, 1595, 965 | 482 |
| (120) | 3300, 1740, 1595, 1100, 1050, 965 | 458 |
| (121) | 3300, 1740, 1595, 1120, 1050 | 472 |
| (122) | 3300, 1740, 1595, 1100, 1020, 965 | 486 |
| (123) | 3300, 2210, 1740, 1595, 965 | 452 |
| (124) | 3300, 1760, 1740, 1595, 1240, 965 | 558 |
| (125) | 3300, 1745, 1600, 965, 770 | 476 |
| (126) | 3400, 3300, 1745, 1680 | 533 |

TABLE 11-continued

| Compound No. | IR ($\nu$ cm$^{-1}$) | Mass (m/e) |
|---|---|---|
|  | 1600, 1500 |  |

EXAMPLES 133–143

Similarly, the procedures of Example 117 were followed except that the starting compound (1) was used, and as the alcohol component were used butanol, octanol, cyclo hexyl methanol, cyclo pentyl methanol, 2-methoxy ethanol, methyl glycolate, methyl lactate, 2-butyn-1-ol, 1,3-di-(O)-acetyl glycerin, phenol and p-acetamino phenol to give the compounds:

5,6,7-trinor-4,8-inter-m-phenylene-16,17,18,19,20-pentanor-15-phenyl PGI$_2$ butyl ester (127), 5,6,7-trinor-4,8-inter-m-phenylene-16,17,18,19,20-pentanor-15-phenyl PGI$_2$ octyl ester (128), 5,6,7-trinor-4,8-inter-m-phenylene-16,17,18,19,20-pentanor-15-phenyl PGI$_2$ cyclohexylmethyl ester (129), 5,6,7-trinor-4,8-inter-m-phenylene-16,17,18,19,20-pentanor-15-phenyl PGI$_2$ cyclopentyl methyl ester (130), 5,6,7-trinor-4,8-inter-m-phenylene-16,17,18,19,20-pentanor-15-phenyl PGI$_2$ (2-methoxy ethyl) ester (131), 5,6,7-trinor-4,8-inter-m-phenylene-16,17,18,19,20-pentanor-15-phenyl PGI$_2$ carbomethoxymethyl ester (132), 5,6,7-trinor-4,8-inter-m-phenylene-16,17,18,19,20-pentanor-15-phenyl PGI$_2$ (1-carbomethoxy ethyl) ester (133), 5,6,7-trinor-4,8-inter-m-phenylene-16,17,18,19,20-pentanor-15-phenyl PGI$_2$ (2-butynyl) ester (134), 5,6,7-trinor-4,8-inter-m-phenylene-16,17,18,19,20-pentanor-15-phenyl PGI$_2$ (1,3-diacetoxy-2-propyl) ester (135), 5,6,7-trinor-4,8-inter-m-phenylene-16,17,18,19,20-pentanor-15-phenyl PGI$_2$ phenyl ester (136), and 5,6,7-trinor-4,8-inter-m-phenylene-16,17,18,19,20-pentanor-15-phenyl PGI$_2$ (p-acetoamino phenyl) ester (137), respectively.

See Table 12.

TABLE 12

| Compound No. | IR ($\nu$ cm$^{-1}$) | Mass (m/e) |
|---|---|---|
| (127) | 3300, 1735, 1595, 965 | 450 |
| (128) | 3300, 1735, 1595, 965 | 506 |
| (129) | 3300, 1735, 1595, 965 | 490 |
| (130) | 3300, 1735, 1595, 965 | 476 |
| (131) | 3300, 1735, 1595, 1100, 1050, 965 | 452 |
| (132) | 3300, 1740, 1595, 1240 1100, 1050, 965 | 466 |
| (133) | 3300, 1740, 1595, 1240 1100, 1050, 965 | 480 |
| (134) | 3300, 2210, 1735, 1595 965 | 446 |
| (135) | 3300, 1760, 1735, 1595 1240, 1100, 965 | 552 |
| (136) | 3300, 1740, 1595, 965 | 470 |
| (137) | 3400, 3300, 1745, 1680 1600, 1500, 965 | 527 |

EXAMPLE 144

5,6,7-trinor-4,8-inter-m-phenylene-16,17,18,19,20-pentanor-15-cyclohexyl PGI$_2$ carboxamide To a solution of 11 mg of 5,6,7-trinor-4,8-inter-m-phenylene-16,17,18,19,20-pentanor-15-cyclohexyl PGI$_2$ (11) in 1 ml of dry THF, cooled with ice were added 0.3 ml of triethylamine and 0.02 ml of ethyl chloroformate. The mixture was stirred at room temperature for 1 hour. The reaction mixture was added dropwise into a flask containing 5 ml of liquid ammonia and adjusted to −33° C. The resulting mixture was stirred at −33° C. for 2 hours. The ammonia was removed, and saturated aqueous sodium chloride was added to the residue, which was then extracted three times with ether. The combined ether layers were washed with saturated aqueous sodium chloride, dried and concentrated to obtain 15 mg of an oily material. The oily material was purified by column chromatography (silica gel; 20% methanol-ethyl acetate) to give 7.6 mg of the amide product.

IR (liquid film) $\nu$ cm$^{-1}$: 3600–3000, 1660, 1600, 760.

NMR $\delta$ (CDCl$_3$): 3.5 (1H, t, J=8.0 Hz) 3.9 (2H, m) 5.10 (1H, m) 5.60 (2H, m) 5.40–5.80 (2H, br) 6.75 (1H, t, J=7.0 Hz) 6.98 (2H, m).

Mass (m/e): 399 (M$^+$), 381, 363.

EXAMPLES 145–147

The procedures of Example 144 were followed except that in place of the ammonia used therein were used methylamine, ethylamine and aniline to give the compounds:

5,6,7-trinor-4,8-trinor-m-phenylene-16,17,18,19,20-pentanor-15-cyclohexyl PGI$_2$ (N-methyl) carboxamide (139), 5,6,7-trinor-4,8-inter-m-phenylene-16,17,18,19,20-pentanor-15-cyclohexyl PGI$_2$ (N-ethyl) carboxamide (140) and 5,6,7-trinor-4,8-inter-m-phenylene-16,17,18,19,20-pentanor-15-cyclohexyl PGI$_2$ anilide (141), respectively.

See Table 13.

TABLE 13

| Compound No. | IR ($\nu$ cm$^{-1}$) | Mass (m/e) |
|---|---|---|
| (139) | 3600–3000, 1660, 1600 960 | 413 |
| (140) | 3600–3000, 1660, 1600 960 | 427 |
| (141) | 3600–3000, 1670, 1600 960 | 475 |

EXAMPLES 148–151

The procedures of Example 144 were followed except that in place of the starting compound 2 used therein were used the compounds 1, 22, 30 and 47 to give the compounds:

5,6,7-trinor-4,8-inter-m-phenylene-16,17,18,19,20-pentanor-15-phenyl PGI$_2$ carboxamide (142), 5,6,7-trinor-4,8-inter-m-phenylene-17,18,19,20-tetranor-16-cyclohexyl PGI$_2$ carboxamide (143), 5,6,7-trinor-4,8-inter-m-phenylene-17,18,19,20-tetranor-16-phenyl PGI$_2$ carboxamide (144) and 5,6,7-trinor-4,8-inter-m-phenylene-18,19,20-trinor-17-phenyl PGI$_2$ carboxamide (145), respectively.

See Table 14.

TABLE 14

| Compound No. | IR ($\nu$ cm$^{-1}$) | Mass (m/e) |
|---|---|---|
| (142) | 3600–3000, 1660, 1600 960 | 393 |
| (143) | 3600–3000, 1660, 1600 960 | 413 |
| (144) | 3600–3000, 1660, 1600 960 | 407 |
| (145) | 3600–3000, 1660, 1600 960 | 421 |

EXAMPLE 152

5,6,7-trinor-4,8-inter-m-phenylene-17,18,19,20-tetranor-16-cyclohexyl PGI$_2$ [N-(p-toluene sulfonyl)]-carboxamide (146)

To 50 mg of sodium hydride (55% mineral oil dispersion), washed three times with hexane and dried, was added 1 ml of dry 1,2-dimethoxy ethane. To the mixture, cooled with ice under stirring, was added dropwise a solution of 260 mg of p-toluene-sulfonamide in 2 ml of 1,2-dimethoxy ethane. The mixture was stirred at room temperature for 1 hour.

Separately, to a solution of 80 mg of 5,6,7-trinor-4,8-inter-m-phenylene-17,18,19,20-tetranor-16-cyclohexyl PGI$_2$ (22) in 2 ml of dry tetrahydrofuran, cooled with ice, were added 0.1 ml of triethylamine and 0.06 ml of ethyl chloroformate. The mixture was stirred at room temperature for 1 hour to prepare the acid anhydride.

To the acid anhydride, while stirred under cooling with ice, was added dropwise the above-prepared, 1,2-dimethoxy-ethane suspension of sodium salt of the sulfonamide. The reaction mixture was stirred at room temperature for 2 hours, followed by addition of water under cooling with ice. The mixture was washed with ether, and the aqueous layer was acidified under cooling with ice to pH 3-2 and extracted three times with ethyl acetate. The combined ethyl acetate layers were washed with water and saturated aqueous sodium chloride, dried and concentrated to give 300 mg of an oily material. The oil was purified by column chromatography (silica gel; eluted with ethyl acetate and subsequently with methanol) to give 79 mg of powders.

IR (CHCl$_3$) $\nu$ cm$^{-1}$: 3600–3000, 1720, 1600, 1450, 1340, 1165, 1085, 970.

NMR $\delta$ (CDCl$_3$): 2.42 (3H, s) 3.50 (1H, t, J=8.0 Hz) 4.18 (2H, m) 5.20 (1H,) 5.60 (2H, m) 6.75 (1H, t, J=8.0 Hz) 6.90 (1H, td, J=8.0 Hz, 2.0 Hz) 6.98 (1H, dd, J=8.0 Hz, 2.0 Hz) 7.32 (2H, d, J=8.0 Hz) 7.93 (2H, d, J=8.0 Hz).

EXAMPLES 153–156

The procedures of Example 152 were followed except that in place of the starting compound 22 therein used were used the compounds 1, 22, 30 and 47 to give the compounds:

5,6,7-trinor-4,8-inter-m-phenylene-16,17,18,19,20-pentanor-15-phenyl PGI$_2$ [N-(p-toluenesulfonyl)] carboxamide (147), 5,6,7-trinor-4,8-inter-m-phenylene-17,18,19,20-tetranor-16-cyclohexyl PGI$_2$ [N-(p-toluenesulfonyl)] carboxamide (148), 5,6,7-trinor-4,8-inter-m-phenylene-17,18,19,20-tetranor-16-phenyl PGI$_2$ [N-(p-toluenesulfonyl)] carboxamide (149), and 5,6,7-trinor-4,8-inter-m-phenylene-18,19,20-trinor-17-phenyl PGI$_2$ [N-(p-toluenesulfonyl)] carboxamide (150), respectively. See Table 15.

TABLE 15

| Compound No. | IR ($\nu$ cm$^{-1}$) | Mass (m/e) |
|---|---|---|
| (147) | 3600–3000, 1720, 1600 1450, 1340, 1165, 1085 970 | 547 |
| (148) | 3600–3000, 1720, 1600 1450, 1340, 1165, 1085 970 | 567 |
| (149) | 3600–3000, 1720, 1600 1450, 1340, 1165, 1085 970 | 561 |
| (150) | 3600–3000, 1720, 1600 1450, 1340, 1165, 1085 970 | 575 |

EXAMPLES 157–158

The procedures of Example 152 were followed except that in place of the p-toluenesulfonamide used therein were used phenylsulfonamide and methanesulfonamide and the compound 1 was used as the starting material to give the compounds:

5,6,7-trinor-4,8-inter-m-phenylene-16,17,18,19,20-pentanor-15-phenyl PGI$_2$ (N-phenylsulfonyl) carboxamide (151), and 5,6,7-trinor-4,8-inter-m-phenylene-16,17,18,19,20-pentanor-15-phenyl PGI$_2$ (N-methanesulfonyl) carboxamide (152), respectively. See Table 16.

TABLE 16

| Compound No. | IR ($\nu$ cm$^{-1}$) | Mass (m/e) |
|---|---|---|
| (151) | 3600–3000, 1720, 1600 1450, 1340, 1165, 1085 970 | — |
| (152) | 3600–3000, 1715, 1600 1450, 1340, 1165, 1085 970 | — |

EXAMPLE 159

2-decarboxy-2-hydroxymethyl-5,6,7-trinor-4,8-inter-m-phenylene-16,17,18,19,20-pentanor-15-cyclohexyl PGI$_2$ (153)

To a solution of 70 mg of 2-decarboxy-2-hydroxymethyl-5,6,7-trinor-4,8-inter-m-phenylene-11(0),15(0)-diacetyl-16,17,18,19,20-pentanor-15-cyclohexyl PGI$_2$ in 1.0 ml of methanol was added (0.5 mg) of 1 N aqueous solution of sodium hydroxide. The mixture was stirred overnight at room temperature. The methanol was removed under reduced pressure, and the residue was extracted with three 1-ml portions of ether. The ether layer was dried and concentrated to give 43 mg of the title compound 153 as an oily substance.

IR (liquid film) $\nu$ cm$^{-1}$: 3350, 2920, 2850, 970, 840.
Mass (m/e): 386.

EXAMPLES 160–161

The procedures of Example 159 were followed except that as the starting compound were used 2-decarboxy-2-hydroxymethyl-5,6,7-trinor-4,8-inter-m-phenylene-11(0),15(0)-diacetyl-16,17,18,19,20-pentanor-15-phenyl PGI$_2$ and 2-decarboxy-2-hydroxymethyl-5,6,7-trinor-4,8-inter-m-phenylene-11(0),15(0)-diacetyl-17,18,19,20-tetranor-16-cyclohexyl PGI$_2$ to give the compounds:

2-decarboxy-2-hydroxymethyl-5,6,7-trinor-4,8-inter-m-phenylene-16,17,18,19,20-pentanor-15-phenyl PGI$_2$ (154) and 2-decarboxy-2-hydroxymethyl-5,6,7-trinor-4,8-inter-m-phenylene-17,18,19,20-tetranor-16-cyclohexyl PGI$_2$ (155), respectively. See Table 17.

TABLE 17

| Compound No. | IR ($\nu$ cm$^{-1}$) | Mass (m/e) |
|---|---|---|
| (154) | 3350, 2920, 2850, 970 760, 740, 695 | — |
| (155) | 3350, 2920, 2850, 970 | — |

TABLE 17-continued

| Compound No. | IR ($\nu$ cm$^{-1}$) | Mass (m/e) |
| --- | --- | --- |
| | 740 | |

EXAMPLE 162

3a,8b-cis-2,3,3a,8b-tetrahydro-1H-5-(4-tetrahydropyranyloxybutyl)-1β-(2-formylethyl)-2α-hydroxycyclopenta[b]benzofuran To a solution of 2 g of 3a,8b-cis-2,3,3a,8b-tetrahydropyranyloxybutyl)-1β-(2-formylethyl)-2α-hydroxycyclopenta[b]benzofuran in 20 ml of ethyl acetate was added 1 g of 5% palladium-carbon catalyst. The mixture was subjected to hydrogenation at ordinary pressure. When ca. 125 ml of hydrogen was absorbed, the reaction was discontinued. After filtration, the ethyl acetate solution was concentrated to afford 1.98 g. of an oily material. The oil was purified by column chromatography (silica gel; developing solvent, cyclohexane:isopropanol:ethyl acetate=1:02:4) to give 1.21 g of the title compound as an oily substance.

IR (liquid film)$\nu$ cm$^{-1}$: 3350, 1715, 840.

Mass (m/e): 388.

EXAMPLE 163

2-decarboxy-2-tetrahydropyranyloxymethyl-5,6,7-trinor-4,8-inter-m-phenylene-13,14-dihydro-16,17,18,19,20-pentanor-15-phenyl PGI$_2$ In 10 ml of THF was dissolved 776 mg of 3a,8b-cis-2,3,3a,8b-tetrahydro-1H-5-(4-tetrahydropyranyloxybutyl)-1β-(2-formylethyl)-2α-hydroxy-cyclopenta[b]benzofuran, and the solution was cooled to −78° C. To the cooled solution was added 3.2 ml of 1.32 M ether solution of phenyllithium. The mixture was stirred at −78° C. for 1.5 hours, followed by 0.5 ml of methanol and 2 ml of saturated aqueous solution of ammonium chloride. The tetrahydrofuran was removed under reduced pressure, followed by addition of 20 ml of water. The aqueous layer was separated, and the ether layer was dried and concentrated. The residue was purified by column chromatography (Merck's Rober Column B; cyclohexane:ethyl acetate:isopropanol=1:4:0.2) to give 342 mg of a 15-epimer mixture of the title compound.

IR (liquid film)$\nu$ cm$^{-1}$: 3350, 2920, 2850, 760, 695.

Mass (m/e): 466.

EXAMPLE 164

2-decarboxy-2-tetrahydropyranyloxymethyl-5,6,7-trinor-4,8-inter-m-phenylene-11(0),15(0)-diacetyl-13,14-dihydro-16,17,18,19,20-pentanor-15-phenyl PGI$_2$ To a solution of 466 mg (1 mmol) of 2-decarboxyl-2-tetrahydropyranyloxymethyl-5,6,7-trinor-4,8-inter-m-phenulene-13,14-dihydro-16,17,18,19,20-pentanor-15-phenyl PGI$_2$ in 4 ml of pyridine was added 4 ml of acetic anhydride. The mixture was stirred at room temperature for 5 hours. The solvent was removed under reduced pressure, and the residue was dissolved in 50 ml of ether. The solution was washed successively with 5 ml of saturated aqueous sodium hydrogen carbonate, 5 ml of saturated aqueous copper sulfate and 5 ml of saturated aqueous sodium chloride, dried over anhydrous magnesium sulfate and concentrated to give 467 mg of the title compound as a pale yellow oily substance.

IR (liquid film)$\nu$ cm$^{-1}$: 2920, 2850, 1740, 770, 690.

Mass (m/e): 550.

EXAMPLE 165

2-decarboxy-2-hydroxymethyl-5,6,7-trinor-4,8-inter-m-phenylene-11(0),15(0)-diacetyl-13,14-dihydro-16,17,18,19,20-pentanor-15-phenyl PGI$_2$ (156)

In 10 ml of a 2:1 mixed solvent of acetic acid and water was dissolved 233 mg of 2-decarboxy-2-tetrahydropyranyloxymethyl-5,6,7-trinor-4,8-inter-m-phenylene-11(0),15(0)-diacetyl-13,14-dihydro-16,17,18,19,20-pentanor-15-phenyl PGI$_2$, and the solution was heated at 40° C. for 3 hours. The solvent was removed under reduced pressure, and the residue was purified by column chromatography (silica gel:ethyl acetate:cyclohexane=1:1) to give 101 mg of a mixture of the title compound and its 15-epimer as an oily substance.

IR (liquid film)$\nu$ cm$^{-1}$: 3350, 2920, 2850, 1740, 970, 760, 740, 695.

Mass (m/e): 466.

EXAMPLE 166

5,6,7-trinor-4,8-inter-m-phenylene-11(0),15(0)-diacetyl-13,14-dihydro-16,17,18,19,20-pentanor-15-phenyl PGI$_2$ (157)

To a solution of 101 mg of 2-decarboxy-2-hydroxymethyl-5,6,7-trinor-4,8-inter-m-phenylene-11(0),15(0)-diacetyl-13,14-dihydro-16,17,18,19,20-pentanor-15-phenyl PGI$_2$ in 2 ml of dimethylformamide was added 840 mg of pyridinium chlomate. The mixture was stirred overnight at room temperature, followed by addition of 6 ml of water. The resulting mixture was extracted with ether (7×15 ml), and the ether layer was washed with saturated aqueous sodium chloride, dried and concentrated to obtain 60 mg of a mixture of the title compound and its 15-epimer.

IR (liquid film)$\nu$ cm$^{-1}$: 1740, 1700, 970, 760, 740, 695.

Mass (m/e): 480.

EXAMPLE 167

5,6,7-trinor-4,8-inter-m-phenylene-13,14-dihydro-16,17,18,19,20-pentanor-15-phenyl PGI$_2$ (158)

To a solution of 60 mg of 5,6,7-trinor-4,8-inter-m-phenylene-11(0),15(0)-diacetyl-13,14-dihydro-16,17,18,19,20-pentanor-15-phenyl PGI$_2$ in 1 ml of methanol was added 0.5 ml of 1 N sodium hydroxide. The mixture was stirred overnight at room temperature. The methanol was removed under reduced pressure from the reaction mixture, which was then acidified with 1 N hydrochloric acid to pH 3 and extracted with ethyl acetate (4×3 ml). The combined ethyl acetate layers was dried and concentrated to obtain 40 mg of a mixture of the title compound and its 15-epimer as an oily substance. The oily substance was purified by column chromatography (ethyl acetate:acetic acid:water=100:2:1) to give 13 mg of 15-epimer (15β isomer) of the title compounds from the earlier eluted fractions (less polar isomer) and 10 mg of the title compound (158) from the later eluted fractions (more polar isomer).

IR (liquid film)$\nu$ cm$^{-1}$: 3500–2500, 1700, 970, 760, 740, 700.

Mass (m/e): 396.

EXAMPLE 168

The procedures of Examples 163–167 were followed except that in place of the phenyllithium used in Example 163 were used ptolyl lithium, m-chloro phenyl lithium, p-bromo phenyl lithium, α-naphthyl lithium, β-naphthyl lithium, m-chloro benzyl magnesium bromide and phenethyl magnesium bromide to give the compounds:

5,6,7-trinor-4,8-inter-m-phenylene-13,14-dihydro-16,17,18,19,20-pentanor-15-(p-tolyl) PGI$_2$ (159),
5,6,7-trinor-4,8-inter-m-phenylene-13,14-dihydro-16,17,18,19,20-pentanor-15-(m-chloro phenyl) PGI$_2$ (160),
5,6,7-trinor-4,8-inter-m-phenylene-13,14-dihydro-16,17,18,19,20-pentanor-15-(p-bromo phenyl) PGI$_2$ (161),
5,6,7-trinor-4,8-inter-m-phenylene-13,14-dihydro-16,17,18,19,20-pentanor-15-(α-naphthyl) PGI$_2$ (162),
5,6,7-trinor-4,8-inter-m-phenylene-13,14-dihydro-16,17,18,19,20-pentanor-15-(β-naphthyl) PGI$_2$ (163),
5,6,7-trinor-4,8-inter-mpphenylene-13,14-dihydro-17,18,19,20-tetranor-16-(m-chloro phenyl) PGI$_2$ (164), and
5,6,7-trinor-4,8-inter-m-phenylene-13,14-dihydro-18,19,20-trinor-17-phenyl PGI$_2$ (165), respectively.
See Table 18.

TABLE 18

| Compound No. | IR ($\nu$ cm$^{-1}$) | Mass (m/e) |
|---|---|---|
| (159) | 3500–2500, 2920, 2850 1700, 810, 740 | 424 |
| (160) | 3500–2500, 2920, 2850 1700, 740 | 432, 430 |
| (161) | 3500–2500, 2920, 2850 1700, 1180, 1020, 740 | 474, 476 |
| (162) | 3500–2500, 2920, 2850 1700, 1180, 1020, 740 | 446 |
| (163) | 3500–2500, 2920, 2850 1700, 1180, 1020, 740 | 446 |
| (164) | 3500–2500, 2920, 2850 1700, 1180, 1020, 740 | 446, 444 |
| (165) | 3500–2500, 2920, 2850 1700, 1180, 1020, 760 740, 695 | 424 |

EXAMPLE 169

2-decarboxy-2-hydroxymethyl-5,6,7-trinor-4,8-inter-m-phenylene-13,14-dihydro-16,17,18,19,20-pentanor-15-phenyl PGI$_2$ (166)

To a solution of 20 mg of 2-decarboxy-2-hydroxymethyl-5,6,7-trinor-4,8-inter-m-phenylene-11(0),15(0)-diacetyl-13,14-dihydro-16,17,18,19,20-pentanor-15-phenyl PGI$_2$ in 1 ml of methanol was added 0.5 ml of 1 N sodium hydroxide. The mixture was stirred overnight at room temperature. The methanol was removed under reduced pressure, which was then acidified with 1 N hydrochloric acid to pH 3.5 and extracted with ethyl acetate (4×3 ml). The ethyl acetate layer was dried and concentrated to obtain a mixture of the title compound and its 15-epimer as an oily substance. The oil was purified by silica gel thin layer chromatography to give 2.5 mg of the title compound from polar fractions.

IR (liquid film)$\nu$ cm$^{-1}$: 3350, 1600, 760, 740, 695. Mass (m/e): 382.

EXAMPLES 170-176

The procedures of Example 144 were followed except that in place of the starting material 11 used therein were used the compound 158, 160, 161, 162, 163, 164 and 165 to give the compounds:
5,6,7-trinor-4,8-inter-m-phenylene-13,14-dihydro-16,17,18,19,20-pentanor-15-phenyl PGI$_2$ carboxamide (167),
5,6,7-trinor-4,8-inter-m-phenylene-13,14-dihydro-16,17,18,19,20-pentanor-15-(m-chloro phenyl) PGI$_2$ carboxamide (168),
5,6,7-trinor-4,8-inter-m-phenylene-13,14-dihydro-16,17,18,19,20-pentanor-15-(p-bromo phenyl) PGI$_2$ carboxamide (169),
5,6,7-trinor-4,8-inter-m-phenylene-13,14-dihydro-16,17,18,19,20-pentanor-15-(α-naphthyl) PGI$_2$ carboxamide (170),
5,6,7-trinor-4,8-inter-m-phenylene-13,14-dihydro-16,17,18,19,20-pentanor-15-(β-naphthyl) PGI$_2$ carboxamide (171),
5,6,7-trinor-4,8-inter-m-phenylene-13,14-dihydro-17,18,19,20-tetranor-16-(m-chloro phenyl) PGI$_2$ carboxamide (172), and
5,6,7-trinor-4,8-inter-m-phenylene-13,14-dihydro-18,19,20-trinor-17-phenyl PGI$_2$ carboxamide (173), respectively.
See Table 19.

TABLE 19

| Compound No. | IR ($\nu$ cm$^{-1}$) | Mass (m/e) |
|---|---|---|
| (167) | 3600–3000, 1660, 1600 760, 740, 695 | 395 |
| (168) | 3600–3000, 1660, 1600 740 | — |
| (169) | 3600–3000, 1660, 1600 740 | — |
| (170) | 3600–3000, 1660, 1600 740 | — |
| (171) | 3600–3000, 1660, 1600 740 | — |
| (172) | 3600–3000, 1660, 1600 740 | — |
| (173) | 3600–3000, 1660, 1600 760, 740, 695 | 423 |

EXAMPLE 177

5,6,7-trinor-4,8-inter-m-phenylene-16,17,18,19,20-pentanor-15-cyclohexyl-15-methyl PGI$_2$ (174)

To a solution of 824 mg (2 mmol) of 5,6,7-trinor-4,8-inter-m-phenylene-16,17,18,19,20-pentanor-15-cyclohexyl PGI$_2$ methyl ester (101) in 80 ml of 80 ml of methylene chloride was added 28 g of active manganese dioxide. The mixture was stirred for 2 hours. The active manganese dioxide was removed by filtration, and the resulting methylene chloride solution was concentrated to give 702 mg of the corresponding 15-oxo compound. To a solution of the 15-oxo compound in 30 ml of tetrahydrofuran were added 5 ml of hexamethylsilazane and 1 ml of trimethylchlorosilane. The mixture was allowed to stand overnight at room temperature. The resulting mixture was filtered, and the filtrate was concentrated under reduced pressure. To the residue was added 10 ml of xylene, and the mixture was again concentrated. The residue from the concentration was dissolved in ether, and to the ether solution was added 1.5 M solution of methylmagnesium bromide in an amount 1.05 times as much as the theoretical. The mixture was allowed to stand at room temperature for 30 minutes and then poured onto 100 ml of saturated aqueous solution of ammonium chloride. The ether layer was separated, and the aqueous layer was extracted with two 20-ml portions of ether. The combined ether layers were washed with brine, then dried and concentrated. The residue was dissolved in 300 ml of ethanol and 10 ml of water containing a few drops of acetic acid, and the solution was stirred at room temperature for 2 hours. The mixture was concentrated under reduced pressure to an aqueous residue, which was extracted with dichloromethane. The dichloromethane was concentrated, and the residue was purified by silica gel chromatography (developing solvent, water-saturated ethyl acetate) to give 117 mg of methyl ester of the title compound. To a solution of the methyl ester in 2 ml of ethanol was added 1 ml of 1 N aqueous solution of potassium hydroxide. The mixture was stirred at room temperature for 20 hours, and then the ethanol was removed under reduced pressure. The residue was cooled to 0° C. and acidified to pH 3.5–4.0 and extracted with ethyl acetate. The ethyl acetate layer was dried and concentrated to give 81 mg of the title compound.

IR (liquid film)$\nu$ cm$^{-1}$: 3500–2800, 1700, 970, 840.
Mass (m/e): 414.

EXAMPLES 178-180

The procedures of Example 177 were followed except that in place of the starting compound 101 used therein were used 103, 104 and 105 to give the compounds:

5,6,7-trinor-4,8-inter-m-phenylene-17,18,19,20-tetranor-15-methyl-16-cyclohexyl PGI$_2$ (175), 5,6,7-trinor-4,8-inter-m-phenylene-17,18,19,20-tetranor-15-methyl-16-phenyl PGI$_2$ (176), and 5,6,7-trinor-4,8-inter-m-phenylene-18,19,20-trinor-15-methyl-17-phenyl PGI$_2$ (177), respectively.

See Table 20.

TABLE 20

| Compound No. | IR ($\nu$ cm$^{-1}$) | Mass (m/e) |
|---|---|---|
| (175) | 3500–2500, 2920, 2850 1700, 1180, 1020, 965 740 | 428 |
| (176) | 3500–2500, 2920, 2850 1700, 1180, 1020, 965 760, 740, 695 | 422 |
| (177) | 3500–2500, 2920, 2850 1700, 1180, 1020, 965 760, 740, 695 | 436 |

REFERENCE EXAMPLE 11

3,5-cis-is(2,6-dibromophenoxy)cyclopentene (A)

In a 500-ml flask flushed with unitrogen was placed 5.6 g (0.117 mol) of sodium hydride, which was washed with n-hexane to remove mineral oil. To the flask was added 100 ml of 1,2-dimethoxyethane. While stirring at 0° C., 29.4 g (0.117 mol) of 2,6-dibromophenol was slowly added. When bubbling was standstill, 280 mg of 18-crown-6 (1.06 18-crown-6 (1.06 mmol., 2 mol% of the 3,5-dibromocyclopentene) and 12 g. (0.053 mmol.) of 3,5-dibromocyclopentene in solid were added.

The mixture was stirred at room temperature for 3 days. After completion of the reaction, the resulting mixture was filtered to obtain a solid material, which was washed with water (3×20 ml) and dissolved in 1.5 l of chloroform. The solution was dried over magnesium sulfate and concentrated to obtain 22.6 g (75%) of as white solid nearly pure 3,5-bis(2,6-dibromophenoxy)-cyclopentene: white needles, m.p. 205.0°–206.0° C.

Elemental Analysis, Calcd: C:35.95, H:2.13. Found: C:35.86, H:2.19.

(C$_{17}$H$_{12}$Br$_4$O$_2$, m.w. 567.93)
Mass (m/e): 571–563 (M+).
IR (KBr disk)$\nu$ cm$^{-1}$:1550, 960, 740.
NMR (CDCl$_3$)$\nu$ ppm: 2.90 (dt, 1H) 3.12 (dt, 1H) 5.10 (dd, 1H) 6.31 (s, 2H) 6.83 (t, 1H) 7.52 (d, 2H).

REFERENCE EXAMPLE 12

3a,8b-cis-dihydro-3H-5-bromocyclopenta[b]benzofuran (B)

In a 50-ml flask flushed with argon was placed 515 mg (0.906 mmol) of 3,5-cis-bis(2,6-dibromophenoxy)cyclopentene (A), which was dissolved in 11 ml of tetrahydrofuran. To the solution cooled to −78° C. was added dropwise 0.72 ml (1.44 mmol) of n-butyllithium (ca. 2.0 M) over a period of 15 minutes. The mixture was stirred at −10° C. for about 3 hours, followed by addition of 5 ml of saturated aqueous ammonium chloride. The resulting mixture was extracted with ether (3×30 ml), and the organic layer was dried over anhydrous magnesium sulfate, concentrated and purified by column chromatography (7 g of silica gel: developing solvent, cyclohexane:ethyl acetate=97:3) to obtain 98.6 mg (0.416 mmol, 45.9%) as a colorless oily substance.

TLC: Rf=0.6 (cyclohexane:ethyl acetate=97:3).
IR (liquid film)$\nu$ cm$^{-1}$: 3060, 2950, 1600, 1585, 945, 750.
NMR (CDCl$_3$)$\delta$ ppm: 2.9 (m, 2H) 4.8 (d, 1H) 5.54 (q, 1H) 5.66 (m, 2H) 6.70 (t, 1H) 7.2 (m, 2H).
Mass (m/e): 238, 236 (M+), 209, 211, 128.

REFERENCE EXAMPLE 13

3a,8b-cis-dihydro-3H-5-(4-tetrahydropyranyloxy-n-butyl)cyclopenta[b]benzofuran (C)

To a solution of 150 mg (0.632 mmol) of 3a,8b-cis-dihydro-3H-5-bromocyclopenta[b]benzofuran (B) in 7 ml of THF at −78° C. was added dropwise 0.32 ml of n-butyllithium (2.0 M). The mixture was stirred for 15 minutes, followed by addition of 216 mg (0.758 mmol, 1.2 equivalents) of 4-iodobutyl-tetrahydropyranylether. The resulting mixture was stirred at −78° C. for 2 hours and at −12° C. for 2 hours, followed by addition of 5 ml of saturated aqueous sodium chloride and extraction with 50 ml of ether. Drying and concentration gave 230 mg of an oily crude product. Purification by high-speed liquid chromatography afforded 171 mg of an oily substance (86.2%).

IR (liquid film)$\nu$ cm$^{-1}$: 3040, 2920, 1590, 748.
NMR (CDCl$_3$)$\delta$ ppm: 1.3–2.0 (m, 10H) 2.58 (t, 2H) 2.84 (m, 2H) 3.4 (m, 2H) 3.8 (m, 2H) 4.37 (d, 1H) 4.56 (s, 1H) 5.44 (m, 1H) 5.74 (s, 2H) 6.7–7.1 (m, 3H).
Mass (m/e): 314 (M+), 230, 214, 171.

REFERENCE EXAMPLE 14

3a,8b-cis-dihydro-3H-5-(4-tetrahydropyranyloxy-n-butyl)-1-exobromo-2-endo-hydroxycyclopenta[b]benzofuran (D)

To a solution of 720 mg (23 mmol) of 3a,8b-cis-dihydro-3H-5-(4-tetrahydropyranyloxy-n-butyl)cyclopenta[b]benzofuran (C) in 20 ml of dimethylsulfoxide:water (18:1) and 3 ml of THF was added 573 mg (3.2 mmol, 1.4 equivalents) of N-bromosuccinimide. The mixture was stirred at 0°–5° C. for 1.5 hours, followed by addition of 5 ml of saturated aqueous sodium hydrogen carbonate and extraction with 200 ml of ether. The extract was dried and concentrated, and the crude product thus obtained was purified by column chromatography to give 450 mg of D.

REFERENCE EXAMPLE 15

3a,8b-cis-dihydro-3H-5-(4-tetrahydropyranyloxy-n-butyl)-1,2-synepoxy-cyclopenta[b]benzofuran (E)

To a solution of 450 mg (1.09 mmol) of 3a,8b-cis-dihydro-3H-5-(4-tetrahydropyranyloxy-n-butyl)-1-exo-bromo-2-endo-hydroxy-cyclopenta[b]benzofuran (D) in 5 ml of methanol was added 322 mg (2.3 mmol) of potassium carbonate. The mixture was stirred at 0° C. for 1.5 hours. The methanol was distilled off under reduced pressure, and the residue was extracted with 20 ml of ether. The extract was dried and concentrated. Column chromatography gave 320 mg (0.97 mmol, 89%) of E.

IR (liquid film) $\nu$ cm$^{-1}$: 3030, 2920, 1590, 1470, 1220, 1130, 965, 840, 745.

NMR (CDCl$_3$) $\delta$ ppm: 1.4–1.8 (m, 10H) 2.2 (dd, 1H) 2.5 (m, 3H) 3.5 (m, 2H) 3.64 (bs, 2H) 3.7 (m, 2H) 3.84 (d, 1H) 4.56 (bs, 1H) 5.3 (t, 1H) 6.7–7.3 (m, 3H).

Mass (m/e): 330 (M$^+$), 246, 227.

REFERENCE EXAMPLE 16

3a,8b-cis-dihydro-3H-5-(4-tetrahydropyranyloxy-n-butyl)-1-exo-(2-formylvinyl)-2-endo-hydroxy-cyclopenta[b]benzofuran (II)

To a solution of 315 mg (0.95 mmol) of 3a,8b-cis-dihydro-3H-5-(4-tetrahydropyranyloxy-n-butyl)-1,2-syn-epoxy-cyclopenta[b]benzofuran in 2 ml of THF cooled to −78° C. was added a THF solution of 1,3-bis-(methylthio)allyl anion (2.4 mmol.). After stirred for 2 hours, 1 ml of methanol and 3 ml of saturated aqueous ammonium chloride were added, and the mixture was extracted with 100 ml of ether. The extract was dried and concentrated.

To the oily material thus obtained were added 2.7 g (10 mmol) of mercuric chloride, 166 g of potassium carbonate, 12 ml of acetonitrile, 3 ml of water and 2 ml of THF. The mixture was heated under argon overnight at 40° C. The reaction mixture was filtered, washed with 50 ml of ether, and the ether layer was washed with 10 ml of saturated aqueous sodium chloride, dried and purified by column chromatography to give 151 mg (41%) of II and 187 mg (51%) of the geometroisomer.

IR (liquid film) $\nu$ cm$^{-1}$: 3600–3300, 2930, 1687, 1635, 1590, 750.

NMR (CDCl$_3$) $\delta$ ppm: 1.5–1.8 (m, 10H) 2.1 (m, 1H) 2.6 (m, 1H) 2.6 (t, 2H) 2.83 (q, 1H) 3.4 (m, 2H) 3.62 (t, 1H) 3.8 (m, 2H) 4.1 (m, 1H) 4.56 (bs, 1H) 5.2 (m, 1H) 6.24 (dd, 1H) 6.7–7.1 (m, 1H).

Mass (m/e): 386 (M$^+$), 302, 284.

REFERENCE EXAMPLE 17

2-decarboxy-2-tetrahydropyranyloxymethyl-5,6,7-trinor-4,8-inter-m-phenylene PGI$_2$ To a solution of 150 mg (0.388 mmol) of 3a,8b-cis-dihydro-3H-5-(4-tetrahydropyranyloxy-n-butyl)-1-exo-(2-formylvinyl)-2-endo-hydroxycyclopenta[b]benzofuran (II0 in 4 ml of THF cooled to −78° C. was added 1.1 ml (3 equivalents) of n-amyllithium (1.08 N), followed by addition of 0.5 ml of methanol and 0.5 ml of ammonium chloride. The mixture was extracted with 30 ml of ether. The extract was dried and concentrated to obtain 200 mg of the mixture. Column chromatography afforded 78.8 mg of the desired product (45%) and 53 mg of the 15-epimer (30%).

IR (liquid film) $\nu$ cm$^{-1}$: 3600–3300, 2920, 1590, 965, 750.

NMR (CDCl$_3$) $\delta$ ppm: 0.90 (t, 3H) 1.2–2.1 (m, 21H) 2.4–2.7 (m, 4H) 3.42 (t, 2H) 3.8 (m, 2H) 3.85 (m, 1H) 4.1 (m, 1H) 4.57 (bs, 1H) 5.1 (m, 1H) 5.62 (m, 2H) 6.7–7.2 (m, 3H).

Mass (m/e): 458 (M$^+$), 440, 422, 396, 374.

REFERENCE EXAMPLE 18

2-decarboxy-2-tetrahydropyranyloxy-5,6,7-trinor-4,8-inter-m-phenylene PGI$_2$ diacetate To 75 mg (0.163 mmol) of 2-decarboxy-2-tetrahydropyranyloxy-5,6,7-trinor-4,8-inter-m-phenylene PGI$_2$ were added 1.2 ml of pyridine and 1.6 ml of acetic anhydride. The mixture was stirred overnight at room temperature. The solvent was distilled off, and the residue was dissolved in 50 ml. of ether. Purificiation by column chromatography gave 82.7 mg (93%) of the diacetate.

IR (liquid film) $\nu$ cm$^{-1}$: 2930, 1735, 965, 800.

NMR (CDCl$_3$) $\delta$ ppm: 0.9 (t, 3H) 2.2–2.8 (m, 20H) 1.73 (s, 3H) 2.06 (s, 3H) 2.1 (m, 1H) 2.6 (m, 3H) 2.8 (m, 1H) 3.4–3.9 (m, 5H) 4.56 (bs, 1H) 4.92 (m, 1H) 5.2 (m, 2H) 5.6 (m, 2H) 6.7–7.1 (m, 3H).

EXAMPLE 181

2-decarboxy-2-hydroxymethyl-5,6,7-trinor-4,8-inter-m-phenylene PGI$_2$ diacetate (178)

To a solution of 82 mg (0.151 mmol) of 2-decarboxy-2-tetrahydropyranyloxymethyl-5,6,7-trinor-4,8-inter-m-phenylene PGI$_2$ diacetate in 5 ml of acetonitrile and 3 ml of THF was added 3 ml of 1/10 N hydrochloric acid. The mixture of stirred at room temperature for 7 hours. To the resulting mixture were added 50 mg of triethylamine and then 3 ml of saturated aqueous sodium hydrogen carbonate, followed by extraction with 30 ml of ether. The extract was concentrated, and the concentrate was purified by column chromatography to give 51.1 mg (73.9%) of the desired product.

IR (liquid film) $\nu$ cm$^{-1}$: 3600–3300, 2920, 2840, 1730, 1590, 960, 800, 740.

NMR (CDCl$_3$) $\delta$ ppm: 0.9 (t, 3H) 1.2–1.9 (m, 12H) 1.73 (s, 3H) 2.04 (s, 3H) 2.1 (m, 1H) 2.6 (m, 3H) 2.8 (m, 1H) 3.6 (m, 1H) 3.64 (t, 2H) 4.9 (m, 1H) 5.2 (m, 2H) 5.6 (m, 2H) 6.7–7 (m, 3H)

Mass (m/e): 458 (M$^+$), 398, 338, 267.

EXAMPLE 182

5,6,7-trinor-4,8-inter-m-phenylene PGI$_2$ diacetate (179)

To a solution of 51 mg (0.112 mmol) of 2-decarboxy-2-hydroxymethyl-5,6,7-trinor-4,8-inter-m-phenylene PGI$_2$ diacetate in 1 ml of dimethylformamide was added 336 mg (0.9 mmol) of pyridine dichromate. The mixture was stired overnight at room temperature, followed by addition of 3 ml of water. The resulting mixture was extracted with 100 ml of ether, and the extract was washed with saturated aqueous sodium chloride and concentrated. There was obtained 46.2 mg (88%) of the desired product.

IR (liquid film) $\nu$ cm$^{-1}$: 3600–2500, 1700, 965.

NMR (CDCl$_3$) $\delta$ ppm: 0.9 (t, 3H) 1.2–2.1 (m, 11H) 1.64 (s, 3H) 2.06 (s, 3H) 2.4 (t, 2H) 2.62 (t, 2H) 2.8 (m, 2H) 3.6 (dd, 1H) 4.92 (q, 1H) 5.2 (m, 2H) 5.6 (m, 2H) 6.7–7.1 (m, 3H).

Mass (m/e): 472 (M$^+$), 352, 281, 225, 211.

EXAMPLE 183

5,6,7-trinor-4,8-inter-m-phenylene $PGI_2$ (180)

To a solution of 46 mg (0.097 mmol) of 5,6,7-trinor-4,8-inter-m-phenylene $PGI_2$ diacetate in 3 ml of methanol was added 1 ml of 1 N aqueous solution of sodium hydroxide. The mixture was stirred overnight at room temperature. The methanol was distilled off, and the residue was neutralized slowly with 1 N hydrochloric acid at 0° C. and extracted with 30 ml of ethyl acetate. The extract was dried and concentrated to give 367 mg (97%) of pure desired product as an oil.

IR (liquid film) $\nu$ cm$^{-1}$: 3600–2500, 1700, 1590, 965, 740.

NMR (CDCl$_3$) $\delta$ ppm: 0.90 (t, 3H) 1.2–1.6 (m, 18H) 1.8–2.1 (m, 3H) 2.35 (t, 2H) 2.5 (m, 2H) 2.63 (t, 2H) 3.40 (t, 1H) 3.9 (m, 1H) 4.1 (m, 1H) 4.8 (b, 3H) 5.1 (m, 1H) 5.6 (m, 2H) 6.7–7.0 (m, 3H)

$^{13}$C.NMR: 157. 1540 (C$_6$).

Mass (m/e): 388 (M$^+$), 370, 352, 326, 308, 219, 204, 158.

EXAMPLE 184

5,6,7-trinor-4,8-inter-m-phenylene $PGI_2$ methyl ester (181)

To a solution of 36 mg (0.093 mmol) of 5,6,7-trinor-4,8-inter-m-phenylene $PGI_2$ in 1 ml of methanol was added the ether solution of diazomethan separately prepared. The solvent was distiled off to give 37 mg of the desired product.

IR (liquid film) $\nu$ cm$^{-1}$: 3600-14 3300, 1735, 1590, 965, 740.

NMR (CDCl$_3$) $\delta$ ppm: 0.90 (t, 3H) 1.2–1.6 (m, 18H) 1.8–2.1 (m, 3H) 2.35 (t, 2H) 2.5 (m, 2H) 2.63 (t, 2H) 3.40 (t, 1H) 3.68 (s, 3H) 3.9 (m, 1H) 4.1 (m, 1H) 4.8 (b, 2H) 5.1 (m, 1H) 5.6 (m, 2H) 6.7–7.0 (m, 3H).

Mass (m/e): 402 (M$^+$), 384, 366.

EXAMPLE 185

15-methyl-5,6,7-trinor-4,8-inter-m-phenylene $PGI_2$ (182)

To a solution of 30 mg (0.066 mmol) of 15-methyl-5,6,7-trinor-4,8-inter-m-phenylene $PGI_2$ diacetate in 2 ml of methanol was added 1 ml of 1 N aqueous solution of sodium hydroxide. The mixture was stirred overnight at room temperature. The methanol was distilled off, and the residue was neutralized with 1 N hydrochloric acid and extracted with ether. The extract was dried and concentrated to give 23 mg (95%) of pure desired product.

IR (liquid film) $\nu$ cm$^{-1}$: 3600–2500, 1700, 1590, 965, 740.

NMR (CDCl$_3$) $\delta$ ppm: 0.90 (t, 3H) 1.2–1.6 (m, 21H) 1.8–2.1 (m, 3H) 2.34 (t, 2H) 2.5 (m, 2H) 2.65 (t, 2H) 3.4 (t, 1H) 3.9 (m, 1H) 4.8 (b, 3H) 5.1 (m, 1H) 5.6 (m, 2H) 6.7–7.1 (m, 3H).

Mass (m/e): 402 (M$^+$), 384, 366, 340.

EXAMPLE 186

2-decarboxy-2-tetrahydropyranyloxymethyl-15-methyl-5,6,7-trinor-4,8-inter-m-phenylene $PGI_2$ To a solution of 82.5 mg (0.18 mmol) of 2decarboxy-2-tetrahydropyranyloxymethyl-5,6,7-trinor-4,8-inter-m-phenylene $PGI_2$ in 3 ml of methylene chloride was added 2 g of manganese dioxide. The mixture was vigorously stirred. After 10 hours, the resulting mixture was filtered, washed with methylene chloride and concentrated. The oily substance thus obtained was dissolved under argon in 2 ml of THF, followed by addition of 0.3 ml of methyllithium (1.5 N) at $-78°$ C., then 0.5 ml of methanol and 3 ml of aqueous ammonium chloride. The mixture was extracted with 30 ml of ether, and the extract was concentrated. Column chromatography of the concentrate afforded 40 mg (48%) of the desired product and 32 mg (38%) of the 15-epimer.

IR (liquid film) $\nu$ cm$^{-1}$: 3600–3300, 2920, 2850, 1590, 965, 820, 740.

Mass (m/e): 472 (M$^+$), 454, 436.

EXAMPLE 187

5,6,7-trinor-4,8-inter-m-phenylene-$\omega$-homo $PGI_2$ (183)

To a solution of 41 mg (0.085 mmol) of 5,6,7-trinor-4,8-inter-m-phenylene-w-homo $PGI_2$ diacetate in 3 ml of methanol was added 1 ml of 1 N aqueous solution of sodium hydroxide. The mixture was stirred overnight at room temperature. The methanol was distilled off, and the residue was neutralized with 1 N hydrochloric acid and extracted with 30 ml of ethyl acetate. The extract was dried and concentrated to give 32 mg (95%) of pure desired product.

IR (liquid film) $\nu$ cm$^{-1}$: 3600–2500, 1700, 1590, 965, 740.

NMR (CDCl$_3$) $\delta$ ppm: 0.90 (t, 3H) 1.2–1.6 (m, 21 H) 1.8–2.1 (m, 3H) 2.35 (t, 2H) 2.5 (m, 2H) 2.64 (t, 2H) 3.42 (t, 1H) 3.9 (m, 1H) 4.1 (m, 1H), 4.6 (s, 3H) 5.1 (m, 1H) 5.6 (m, 2H) 6.7–7.1 (m, 3H).

Mass (m/e): 402 (M$^+$), 384, 366.

EXAMPLE 188

13,14-dihydro-5,6,7-trinor-4,8-inter-m-phenylene $PGI_2$ (184)

To a solution of 25 mg (0.062 mmol) of 5,6,7-trinor-4,8-inter-m-phenylene $PGI_2$ in 1 ml of methanol was added 10 mg of Pd(10%)-carbon. The mixture was stirred under hydrogen at ordinary pressure for 2 hours. The reaction mixture was filtered and washed with methanol. Concentration of the filtrate and washing gave 25 mg (99%) of the desired product as an oil.

IR (liquid film) $\nu$ cm$^{-1}$: 3600–2500, 1700, 1590, 740.

NMR (CDCl$_3$) $\delta$ ppm: 0.90 (t, 3H) 1.2–1.6 (m, 22H) 1.8–2.1 (m, 1H) 2.38 (t, 2H) 2.5 (m, 2H) 2.65 (t, 2H) 3.45 (t, 1H) 3.9 (m, 1H) 4.1 (m, 1H) 5.3 (b, 4H) 6.7–7.2 (m, 3H)

Mass (m/e): 390 (M$^+$), 372, 354.

EXAMPLE 189

5,6,7-trinor-4,8-inter-m-phenylene-20-n-amyl $PGI_2$ (185)

To a solution of 45 mg (0.084 mmol) of 5,6,7-trinor-4,8-inter-m-phenylene-20-n-amyl $PGI_2$ diacetate in 4 ml of methanol was added 1 ml of 1 N aqueous solution of sodium hydroxide. The mixture was stirred overnight at room temperature. The methanol was distilled off, and the residue was neutralized with 1 N hydrochloric acid and extracted with 30 ml of ether. The extract was dried and concentrated to give 35 mg (94%) of pure desired product.

IR (liquid film) $\nu$ cm$^{-1}$ 3600–2500, 1700, 1590, 965, 740.

NMR (CDCl$_3$) $\delta$ppm: 0.90 (t, 3H) 1.2–1.6 (m, 29H) 1.8–2.1 (m, 3H) 2.35 (t, 2H) 2.5 (m, 2H) 2.64 (t, 2H) 3.42 (t, 1H) 3.9 (m, 1H) 4.0 (m, 1H) 4.6 (s, 3H) 5.1 (m, 1H) 5.6 (m, 2H) 6.7–7.1 (m, 3H).

Mass (m/e): 458 (M+), 440, 422.

EXAMPLE 190

5,6,7-trinor-4,8-inter-m-phenylene PGI$_2$ n-butyl ester (186)

From 32 mg (0.982 mmol) of 5,6,7-trinor-4,8-inter-m-phenylene PGI$_2$ was prepared the sodium salt with aqueous sodium hydroxide (1N, 82 μl), which was dried. To the dried salt were added 1 ml of dimethylformamide and then 13 mg of n-butyl bromide. The mixture was heated at 40° C. with stirring overnight. To the reaction mixture was added 3 ml of water, followed by extraction with 30 ml of ether. The extract was dried and concentrated to give 35 mg (97%) of pure desired product.

IR (liquid film) ν cm$^{-1}$: 3600–3300, 1740m 1590, 965, 740.

NMR (CDCl$_3$) δppm: 0.90 (t, 3H) 1.2–1.6 (m, 23H) 1.8–2.1 (m, 3H) 2.35 (t, 2H) 2.5 (m, 2H) 2.64 (t, 2H) 3.42 (t, 1H) 3.9 (m, 1H) 4.1 (m, 1H) 4.2 (t, 2H) 4.6 (s, 3H) 5.1 (m, 1H) 5.6 (m, 2H) 6.7–7.1 (m, 9H).

Mass (m/e): 444(M+), 426, 408.

We claim:

1. A compound of the formula

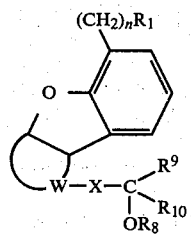

wherein R$_1$ is (a) carboxyl group, (b) its salt, (c) its ester, (d) its amide or (e) —CH$_2$OH, n is an integer of from 1 to 3, W is (a) —CH$_2$—CH=C$\langle$, (b) —CH$_2$—CH$_2$—CH$\langle$ or (c) —CH$_2$—CH—CH$\langle$
$\quad\quad\quad\quad\quad\quad\quad\quad\quad\quad\quad\quad$ |
$\quad\quad\quad\quad\quad\quad\quad\quad\quad\quad\quad\quad$ OR$_8$ wherein R$_8$ is hydrogen, acyl of 1 to 12 carbon atoms, tetrahydropyranyl, tetrahydrofuranyl or 1-ethoxyethyl, X is (a) —CH$_2$CH$_2$— or (b) 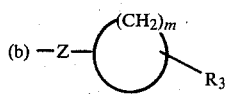, R$_9$ is (a) hydrogen or (b) alkyl of 1 to 4 carbon atoms, R$_{10}$ is (a) straight alkyl of 4 to 12 carbon atoms, (b) —Z—⟨(CH$_2$)$_m$⟩—R$_3$ wherein Z is a valence bond or alkylene of 1 to 5 carbon atoms, m is an integer of from 5 to 12, R$_3$ is hydrogen or alkyl of 1 to 5 carbon atoms, or (c) —Z—Ar$_2$ wherein Z is as defined above, Ar$_2$ is phenyl, α-naphthyl, β-naphthyl or phenyl substituted by at least one chloro, bromo, fluoro, trifluoromethyl, alkyl of 1 to 4 carbon atoms, nitro, methoxy, phenyl or phenoxy.

2. A compound as claimed in claim 1 wherein W is

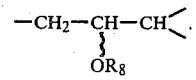

3. A compound as claimed in claim 2 wherein R$_8$ is hydrogen.

4. A compound of claim 1 wherein said salt in R$_1$ is a phermaceutically acceptable cation.

5. A compound as claimed in any of claims 1 to 3 wherein said ester in R$_1$ is —COOR$_2$, wherein R$_2$ is (a) straight alkyl of 1 to 12 carbon atoms or branched alkyl of 3 to 12 carbon atoms, (b) —Z—⟨(CH$_2$)$_m$⟩—R$_3$ wherein Z, m and R$_3$ are as defined in claim 1, (c) —(CH$_2$CH$_2$O)l CH$_3$ wherein l is an integer of 1 to 5, (d) —Z—Ar$_1$ wherein z is as defined in claim 1, Ar$_1$ is phenyl, α-naphthyl, β-naphthyl, 2-pyridyl, 3-pyridyl, 4-pyridyl, α-furyl, β-furyl, α-thienyl, β-thienyl or phenyl substituted by at least one chloro, bromo, fluoro, trifluoromethyl, alkyl of 1 to 4 carbon atoms, nitro, methoxy, phenyl, phenoxy,

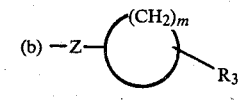

(e) —C$_l$H$_{2l}$COOR$_3$ wherein R$_3$ is as defined in claim 1 and l is as defined above, (f) —C$_l$H$_{2l}$N(R$_3$)$_2$ wherein R$_3$ is as defined in claim 1 and l is as defined above,

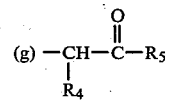

wherein R$_4$ is hydrogen or benzoyl, R$_5$ is phenyl, p-bromophenyl, p-biphenyl, p-nitrophenyl, p-benzamidophenyl, or 2-naphthyl, (h) —C$_l$H$_{2l}$—B, wherein l is as defined above, B is

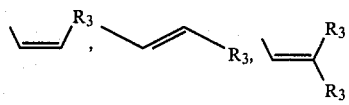

or —C≡C—R$_6$ wherein R$_3$ is as defined above, R$_6$ is alkyl of 1 to 30 carbon atoms or aralkyl of 7 to 30 carbon atoms, or

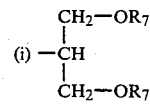

wherein R$_7$ is alkyl of 1 to 30 carbon atoms or acyl of 1 to 30 carbon atoms.

6. A compound as claimed in any of claims 1 to 3 wherein said amide in R$_1$ is

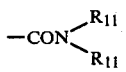

wherein R$_{11}$ is hydrogen, alkyl of 1 to 10 carbon atoms, cycloalkyl of 3 to 12 carbon atoms, phenyl, phenyl substituted by at least one chloro, bromo, fluoro, trifluoromethyl, alkyl of 1 to 4 carbon atoms, nitro, methoxy, phenyl, phenoxy,

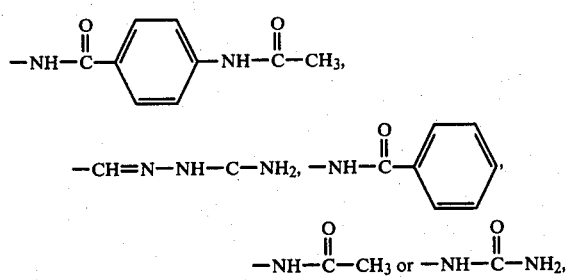

aralkyl of 7 to 12 carbon atoms or —SO$_2$R$_{12}$ wherein R$_{12}$ has the same definition as R$_{11}$ excepting —SO$_2$R$_{12}$, both of R$_{11}$ may be same or different with the proviso that both of R$_{11}$ are not —SO$_2$R$_{12}$ simultaneously.

7. A compound as claimed in any of claims 1 to 3 wherein R$_1$ is carboxyl group, its pharmaceutically acceptable cation or its methyl ester.

8. A compound of claim 1 wherein n is 3.

9. A compound of claim 1 wherein Z is a valence bond.

10. A compound of claim 1 wherein R$_{10}$ is cyclohexyl, cyclopentyl, phenyl, n-pentyl or n-hexyl.

11. 5,6,7-trinor-4,8-inter-m-phenylene-16,17,18,19,20-pentanor-15-phenyl PGI$_2$.

12. 5,6,7-trinor-4,8-inter-m-phenylene-16,17,18,19,20-pentanor-15-cyclohexyl PGI$_2$.

13. 5,6,7-trinor-4,8-inter-m-phenylene-16,17,18,19,20-pentanor-15-cyclopentyl PGI$_2$.

14. 5,6,7-trinor-4,8-inter-m-phenylene-17,18,19,20-tetranor-16-cyclohexyl PGI$_2$.

15. 5,6,7-trinor-4,8-inter-m-phenylene-17,18,19,20-tetranor-16-phenyl PGI$_2$.

16. 5,6,7-trinor-4,8-inter-m-phenylene-17,18,19,20-tetranor-16-p-tolyl PGI$_2$.

17. 5,6,7-trinor-4,8-inter-m-phenylene-13,14-dihydro-16,17,18,19,20-pentanor-15-phenyl PGI$_2$.

18. 5,6,7-trinor-4,8-inter-m-phenylene-13,14-dihydro-16,17,18,19,20-pentanor-15-cyclohexyl PGI$_2$.

19. 5,6,7-trinor-4,8-inter-m-phenylene-13,14-dihydro-16,17,18,19,20-pentanor-15-cyclopentyl PGI$_2$.

20. 11-acetyl-5,6,7-trinor-4,8-inter-m-phenylene-16,17,18,19,20-pentanor-15-(p-tolyl) PGI$_2$ benzyl ester.

21. 5,6,7-trinor-4,8-inter-m-phenylene-16,17,18,19,20-pentanor-15-(p-tolyl) PGI$_2$.

22. 5,6,7-trinor-4,8-inter-m-phenylene-16,17,18,19,20-pentanor-15-cyclohexyl PGI$_2$ methyl ester.

23. 5,6,7-trinor-4,8-inter-m-phenylene-16,17,18,19,20-pentanor-15-phenyl PGI$_2$ ethyl ester.

24. 5,6,7-trinor-4,8-inter-m-phenylene-17,18,19,20-tetranor-16-cyclohexyl PGI$_2$ methyl ester.

25. 5,6,7-trinor-4,8-inter-m-phenylene-17,18,19,20-tetranor-16-phenyl PGI$_2$ methyl ester.

26. 5,6,7-trinor-4,8-inter-m-phenylene-16,17,18,19,20-pentanor-15-cyclohexyl PGI$_2$ (N-ethyl) carboxamide.

27. 5,6,7-trinor-4,8-inter-m-phenylene PGI$_2$.

28. 5,6,7-trinor-4,8-inter-m-phenylene PGI$_2$ methyl ester.

29. 5,6,7-trinor-4,8-inter-m-phenylene-ω-homo PGI$_2$.

30. 13,14-dihydro-5,6,7-trinor-4,8-inter-m-phenylene PGI$_2$.

31. A pharmaceutical composition for use as an antiulceric drug comprising a compound of claim 1 in association with a pharmaceutically acceptable carrier in sufficient amount to provide from about 0.1 to about 100 mg of said compound per dose.

32. A pharmaceutical composition for use as a hypotensive agent comprising a compound of claim 1 in association with a pharmaceutically acceptable carrier in sufficient amount to provide from about 0.01 to 50 mg per dose.

33. A pharmaceutical composition for use as an antithrombosic agent comprising a compound of claim 1 in association with a pharmaceutically acceptable carrier in sufficient amount to provide from about 0.01 to about 50 mg per dose.

* * * * *